(12) United States Patent
Butler et al.

(10) Patent No.: US 7,524,860 B2
(45) Date of Patent: Apr. 28, 2009

(54) ANTIBACTERIAL AGENTS

(75) Inventors: David Charles Donnell Butler, Meford, MA (US); Huifen Chen, Plymouth, MI (US); Vishnumurthy Ramachandra Hegde, Chelmsford, MA (US); Chris Limberakis, Saline, MI (US); Ravindra Madhukar Rasne, Chelmsford, MA (US); Richard John Sciotti, Saline, MI (US); Jeremy Tyson Starr, Ann Arbor, MI (US)

(73) Assignee: Pfizer Inc., New York, NY (US)

( * ) Notice: Subject to any disclaimer, the term of this patent is extended or adjusted under 35 U.S.C. 154(b) by 171 days.

(21) Appl. No.: 11/576,538

(22) PCT Filed: Sep. 23, 2005

(86) PCT No.: PCT/IB2005/003112

§ 371 (c)(1),
(2), (4) Date: Apr. 30, 2007

(87) PCT Pub. No.: WO2006/038116

PCT Pub. Date: Apr. 13, 2006

(65) Prior Publication Data

US 2008/0021059 A1    Jan. 24, 2008

Related U.S. Application Data

(60) Provisional application No. 60/710,592, filed on Aug. 24, 2005, provisional application No. 60/616,931, filed on Oct. 7, 2004.

(51) Int. Cl.
| | |
|---|---|
| *A01N 43/42* | (2006.01) |
| *A61K 31/44* | (2006.01) |
| *C07D 471/02* | (2006.01) |
| *C07D 491/02* | (2006.01) |
| *C07D 498/02* | (2006.01) |
| *C07D 513/02* | (2006.01) |
| *C07D 515/02* | (2006.01) |

(52) U.S. Cl. .................. 514/303; 546/119; 546/121
(58) Field of Classification Search ................ 546/119, 546/121; 514/303
See application file for complete search history.

(56) References Cited

U.S. PATENT DOCUMENTS

| 4,105,767 A | 8/1978 | Bochis et al. |
| 6,518,222 B2 * | 2/2003 | Arndt et al. ................. 504/241 |
| 2004/0039012 A1 | 2/2004 | Wilson |

FOREIGN PATENT DOCUMENTS

WO    02060879 A    8/2002

OTHER PUBLICATIONS

Wermuth et al: "The Practise of Medicinal Chemistry" Practice of Medicinal Chemistry, 1996, pages.

* cited by examiner

*Primary Examiner*—D. Margaret Seaman
*Assistant Examiner*—Niloofar Rahmani
(74) *Attorney, Agent, or Firm*—Steve T. Zelson; Christian M. Smolizza

(57) ABSTRACT

The present invention is directed to a new class of triazolopyridine derivatives, to their use as antimicrobials, and to pharmaceuticals containing these compounds.

11 Claims, No Drawings

ANTIBACTERIAL AGENTS

CROSS REFERENCE TO RELATED APPLICATION

This application is a submission under 35 U.S.C. 371 of PCT/IB2005/003112 filed on Sep. 23, 2005, which claims priority to U.S. Provisional Application No. 60/616,931, filed Oct. 7, 2004 and U.S. Provisional Application No. 60/710,592 filed Aug. 24, 2005, the contents of each which are hereby incorporated by reference.

FIELD OF THE INVENTION

The present invention relates to a new class to triazolopyridine derivatives, to their use as antibacterial agents, to pharmaceutical compositions containing these compounds and to methods for their preparation.

BACKGROUND OF THE INVENTION

Antibacterial resistance is a global clinical and public health problem that has emerged with alarming rapidity in recent years and undoubtedly will increase in the near future. Resistance is a problem in the community as well as in health care settings, where transmission of bacteria is greatly amplified. Because multiple drug resistance is a growing problem, physicians are now confronted with infections for which there is no effective therapy. The morbidity, mortality, and financial costs of such infections pose an increasing burden for health care systems worldwide. Strategies to address these issues emphasize enhanced surveillance of drug resistance, increased monitoring and improved usage of antimicrobial drugs, professional and public education, development of new drugs, and assessment of alternative therapeutic modalities.

As a result, alternative and improved agents are needed for the treatment of bacterial infections, particularly for the treatment of infections caused by resistant strains of bacteria, e.g., penicillin-resistant, methicillin-resistant, ciprofloxacin-resistant, and/or vancomycin-resistant strains.

SUMMARY OF THE INVENTION

In accordance with the present invention, a new class of antibacterial agents has been discovered that may be represented by Formula I below:

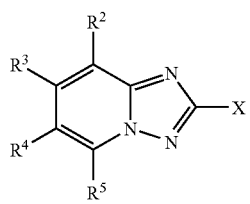

I or a salt thereof, wherein:
X is represented by NH—C(J)-T-$R^1$ or NH—$SO_2$—NH—$R^1$;
J is represented by O or S;
T is represented by NH or O;
$R^1$ is represented by a substituent selected from the group consisting of:
 i) hydrogen,
 ii) ($C_1$-$C_6$)alkyl, optionally substituted,
 iii) ($C_3$-$C_6$)cycloalkyl, optionally substituted,
 iv) ($C_3$-$C_6$) cycloalkyl($C_1$-$C_6$)alkyl, in which the alkyl and cycloalkyl moieties may each be optionally substituted,
 v) phenyl, optionally substituted, and,
 vi) phenyl ($C_1$-$C_6$)alkyl, in which the alkyl and phenyl moieties may each be optionally substituted;
$R^2$, $R^3$, $R^4$, and $R^5$ are each independently represented by a substituent selected from the group consisting of:
 i) hydrogen,
 ii) halogen,
 iii) cyano,
 iv) hydroxy,
 v) ($C_1$-$C_{12}$)alkyl, optionally substituted,
 vi) ($C_2$-$C_{12}$)alkenyl, optionally substituted,
 vii) ($C_2$-$C_{12}$)alkynyl, optionally substituted,
 viii) ($C_3$-$C_{10}$)cycloalkyl, optionally substituted,
 ix) ($C_3$-$C_{10}$) cycloalkyl($C_1$-$C_6$)alkyl, in which the alkyl and cycloalkyl moieties may each be optionally substituted,
 x) ($C_6$-$C_{10}$)aryl, optionally substituted,
 xi) ($C_6$-$C_{10}$)aryl ($C_1$-$C_6$)alkyl, in which the alkyl and aryl moieties may each be optionally substituted,
 xii) heteroaryl, optionally substituted,
 xiii) heteroaryl($C_1$-$C_{12}$)alkyl, in which the heteroaryl and alkyl moieties may each be optionally substituted,
 xiv) heterocyclic, optionally substituted,
 xv) heterocyclic($C_1$-$C_{12}$)alkyl, in which the alkyl and heterocyclic moieties may each be substituted,
 xvi) $(CH_2)_z$—$SR^6$,
 xvii) $(CH_2)_z$—$OR^6$,
 xviii) $(CH_2)_z$—$NR^7R^6$,
 xix) $(CH_2)_z$—$COOR^6$,
 xx) $(CH_2)_z$—$CONR^6R^7$,
 xxi) $(CH_2)_z$—$NR^7COR^6$,
 xxii) $(CH_2)_z$—$OCOR^6$,
 xxiii) $(CH_2)_z$—$C(O)R^6$,
 xxiv) $(CH_2)_z$—$C(O)C(O)NR^6R^7$,
 xxv) $(CH_2)_z$—$SO_xR^6$,
 xxvi) $(CH_2)_z$—$SO_2NR^6R^7$,
 xxvii) $(CH_2)_z$—$NR^7$—$SO_2R^6$
 xxviii) $C(R^6)$=$NOR^7$,
 xxix)

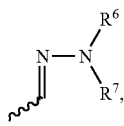

wherein "⌇" indicates the point of attachment, and,
 xxx)

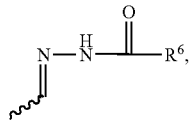

z is an integer selected from the group consisting of 0, 1, 2, 3, or 4;
x is an integer selected from the group consisting of 1 or 2;
$R^6$ is represented by a substituent selected from the group consisting of:

i) hydrogen
ii) $(C_1-C_{12})$alkyl, optionally substituted,
iii) $(C_2-C_{12})$alkenyl, optionally substituted,
iv) $(C_2-C_{12})$alkynyl, optionally substituted,
v) $(C_3-C_{10})$cycloalkyl, optionally substituted,
vi) $(C_3-C_{10})$ cycloalkyl$(C_1-C_6)$alkyl, in which the alkyl and cycloalkyl moieties may each be optionally substituted,
vii) $(C_6-C_{10})$aryl, optionally substituted,
viii) $(C_6-C_{10})$aryl $(C_1-C_6)$alkyl, in which the alkyl and aryl moieties may each be optionally substituted,
ix) heteroaryl, optionally substituted,
x) heteroaryl$(C_1-C_{12})$alkyl, in which the heteroaryl and alkyl moieties may each be optionally substituted,
xi) heterocyclic, optionally substituted,
xii) heterocyclic$(C_1-C_{12})$alkyl, in which the alkyl and heterocyclic moieties may each be substituted;

$R^7$ is represented by a substituent selected from the group consisting of hydrogen and $(C_1-C_6)$ alkyl; with the proviso that one of $R^2$ or $R^5$ will be represented by hydrogen, halogen, methyl, cyano, hydroxy, trifluoromethyl, trifluoromethoxy, or methoxy.

The compounds of Formula I exhibit antibacterial activity. They may be used to treat bacterial infections in mammals, especially humans. The compounds may also be used for veterinary applications, such as treating infections in livestock and companion animals.

The compounds exhibit activity against selected strains of gram-positive bacteria, gram-negative bacteria, and anaerobic bacteria. They may be used to treat common infections such as otitis media, sinusitis, pharyngitis/tonsilitis, bronchitis, urinary tract infections, skin infections, pneumonia, septicemia, etc. In order to simplify administration, the compounds will typically be admixed with at least one excipient and formulated into pharmaceutical dosage forms. Examples of such dosage forms include tablets, capsules, solutions/suspensions for injection, and solutions/suspensions for oral ingestion.

DETAILED DESCRIPTION OF THE INVENTION

The headings within this document are only being utilized to expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.
b. "$C_1-C_6$ alkyl" refers to a branched or straight chained alkyl group containing from 1 to 6 carbon atoms, such as methyl, ethyl, n-propyl, isopropyl, n-butyl, isobutyl, pentyl, etc.
c. "$C_1-C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, haloalkyl, hydroxy, thiol, cyano, $OR^8$ and $NR^8R^9$ in which $R^8$ and $R^9$ are each independently represented by a substituent selected from the group consisting of hydrogen and $(C_1-C_6)$ alkyl.
d. "$C_1-C_{12}$ alkyl, optionally substituted" refers to a branched or straight chained alkyl group containing from 1 to 12 carbon atoms, such as methyl, ethyl, n-propyl, isopropyl, n-butyl, isobutyl, hexyl, octyl, decyl, etc. Such an alkyl group may be optionally substituted, in which up to 8 hydrogen atoms are replaced by a substituent selected from the group consisting of halogen, haloalkyl, hydroxy, thiol, cyano, $OR^8$ and $NR^8R^9$, in which $R^8$ and $R^9$ are as defined above.
e. "$C_2-C_{12}$ alkenyl optionally substituted" refers to a straight-chain or branched-chain hydrocarbon radical containing from 2 to 12 carbon atoms and 1, or more, carbon-carbon double bond. Examples of alkenyl radicals include ethenyl, propenyl, 1,4-butadienyl, 1-hexenyl, 1,3-octadienyl and the like. Such an alkenyl group may be optionally substituted, in which up to 8 hydrogen atoms are replaced by a substituent selected from the group consisting of halogen, haloalkyl, hydroxy, thiol, cyano, $OR^8$ and $NR^8R^9$, in which $R^8$ and $R^9$ are as defined above.
f. "$C_2-C_{12}$ alkynyl optionally substituted" refers to a straight-chain or branched-chain hydrocarbon radical containing from 2 to 12 carbon atoms and having 1, or more, carbon-carbon triple bonds. Examples of alkynyl radicals include ethynyl, propynyl, butynyl, octynyl, and the like. Such an alkynyl group may be optionally substituted, in which up to 8 hydrogen atoms are replaced by a substituent selected from the group consisting of halogen, hydroxy, haloalkyl, thiol, cyano, $OR^8$ and $—NR^8R^9$, in which $R^8$ and $R^9$ are as defined above.
g. "haloalkyl" refers to a branched or straight chained alkyl group containing from 1 to 6 carbon atoms, in which at least one hydrogen atom is replaced with a halogen (i.e. $C_1-C_6$ haloalkyl). Examples of suitable haloalkyl's include chloromethyl, difluoromethyl, trifluoromethyl, 1-fluoro-2-chloro-ethyl, 5-fluoro-hexyl, 3-difluoro-isopropyl, 3-chloro-isobutyl, etc.
h. "$(C_1-C_2)$alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluoromethyl, dichloromethyl, etc.).
i. "$(C_1-C_2)$alkoxy substituted with one or more halogen atoms" refers to a straight chained alkoxy group containing 1 or 2 carbon atoms, i.e., methoxy or ethoxy in which at least one hydrogen atom is replaced with a halogen (i.e. for example trifluoromethoxy, difluoromethoxy, etc.)
j. "$C_1-C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.
k. "haloalkoxy" refers to a branched or straight chained alkoxy group containing from 1 to 6 carbon atoms, in which at least one hydrogen atom is replaced with a halogen (i.e. $C_1-C_6$ haloalkoxy). Examples of suitable haloalkoxy's include chloromethoxy, difluoromethoxy, trifluoromethoxy, 1-fluoro-2-chloro-ethoxy, 5-fluoro-hexoxy, 3-difluoro-isopropoxy, 3-chloro-isobutoxy, etc.
l. "$(C_6-C_{10})$aryl" optionally substituted means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, cyano, hydroxy, $(C_1-C_6)$ alkyl, $(C_1-C_6)$alkoxy, $(C_1-C_2)$alkyl substituted with one or more halogens, $(C_1-C_2)$alkoxy substituted with one or more halogens, $SR^8$ and $NR^8R^9$, in which $R^8$ and $R^9$ are as defined above. These substituents may be the same or different and may be located at any position of the ring, that is chemically permissible.

m. "phenyl, optionally substituted" refers to a phenyl ring. This ring may be optionally substituted with up to 4 non-hydrogen substituents, each substituent is independently selected from the group consisting of halogen, cyano, hydroxy, $(C_1-C_6)$alkyl, $(C_1-C_6)$alkoxy, $(C_1-C_2)$alkyl substituted with one or more halogens, $(C_1-C_2)$alkoxy substituted with one or more halogens, $SR^8$ and $NR^8R^9$, in which $R^8$ and $R^9$ are as defined above. These substituents may be the same or different and may be located at any position of the ring, that is chemically permissible.

n. "$(C_3-C_{10})$ cycloalkyl" optionally substituted refers to a saturated or partially saturated monocyclic, bicyclic or tricyclic alkyl radical wherein each cyclic moiety has 3 to 10 carbon atoms. Examples of cycloalkyl radicals include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, hydroxy, $(C_1-C_6)$ alkyl, $(C_1-C_6)$alkoxy, $(C_1-C_2)$alkyl substituted with one or more halogens, $(C_1-C_2)$alkoxy substituted with one or more halogens, $SR^8$, and $NR^8R^9$, in which $R^8$ and $R^9$ are as defined above. Where possible, the cycloalkyl group may contain double bonds, for example, 3-cyclohexen-1-yl.

o. "$(C_3-C_6)$cycloalkyl" means a hydrocarbon ring containing from 3 to 6 carbon atoms, for example, cyclopropyl, cyclobutyl, cyclopentyl, or cyclohexyl. Where possible, the cycloalkyl group may contain double bonds, for example, 3-cyclohexen-1-yl. The cycloalkyl ring may be unsubstituted or optionally be substituted in the same manner as a "$(C_3-C_{10})$ cycloalkyl".

p. "heteroaryl" refers to an aromatic ring having one, or more, heteroatoms selected from oxygen, nitrogen and sulfur. More specifically, it refers to a 5- or 6-, membered ring containing 1, 2, 3, or 4 nitrogen atoms; 1 oxygen atom; 1 sulfur atom; 1 nitrogen and 1 sulfur atom; 1 nitrogen and 1 oxygen atom; 2 nitrogen atoms and 1 oxygen atom; or 2 nitrogen atoms and 1 sulfur atom. The 5-membered ring has 2 double bonds and the 6-membered ring has 3 double bonds. The term heteroaryl also includes bicyclic groups in which the heteroaryl ring is fused to a benzene ring, heterocyclic ring, a cycloalkyl ring, or another heteroaryl ring. Examples of such heteroaryl ring systems include, but are not limited to, pyrrolyl, furanyl, thienyl, imidazolyl, oxazolyl, indolyl, thiazolyl, pyrazolyl, pyridinyl, pyrimidinyl, purinyl, quinolinyl, benzofuran, tetrazole, isoquinolinyl, oxadiazolyl, thiadiazolyl, isothiazolyl, isoxazolyl, triazolyl, benzo[b]thienyl, 2-, 4-, 5-, 6-, or 7-benzoxazolyl, 7-benzimidazolyl, or benzothiazolyl.

q. "heteroaryl, optionally substituted," refers to a heteroaryl moiety as defined immediately above, in which up to 4 carbon atoms of the heteroaryl moiety may be substituted with a substituent, each substituent is independently selected from the group consisting of halogen, cyano, hydroxy, $(C_1-C_6)$alkyl, $(C_1-C_6)$alkoxy, $(C_1-C_2)$alkyl substituted with one or more halogens, $(C_1-C_2)$ alkoxy substituted with one or more halogens, $SR^8$, and $NR^8R^9$, in which $R^8$ and $R^9$ are as defined above.

r. "heterocycle" or "heterocyclic ring" refers to any 3- or 4-membered ring containing a heteroatom selected from oxygen, nitrogen and sulfur; or a 5-, 6-, 7-, 8-, 9-, or 10-membered ring containing 1, 2, or 3 nitrogen atoms; 1 oxygen atom; 1 sulfur atom; 1 nitrogen and 1 sulfur atom; 1 nitrogen and 1 oxygen atom; 2 oxygen atoms in non-adjacent positions; 1 oxygen and 1 sulfur atom in non-adjacent positions; or 2 sulfur atoms in non-adjacent positions. The 5-membered ring has 0 to 1 double bonds, the 6- and 7-membered rings have 0 to 2 double bonds, and the 8, 9, or 10 membered rings may have 0, 1, 2, or 3 double bonds. The term "heterocyclic" also includes bicyclic groups in which any of the above heterocyclic rings is fused to a benzene ring, a cyclohexane or cyclopentane ring or another heterocyclic ring (for example, indolyl, quinolyl, isoquinolyl, tetrahydroquinolyl, benzofuryl, dihydrobenzofuryl or benzothienyl and the like). Heterocyclics include: pyrrolidinyl, tetrahydrofuranyl, tetrahydrothiophenyl, piperidinyl, piperazinyl, azepane, azocane, morpholinyl, isochromyl, quinolinyl, tetrahydrotriazine, tetrahydropyrazole, dihydro-oxathiol-4-yl, dihydro-1H-isoindole, tetrahydro-oxazolyl, tetrahydro-oxazinyl, thiomorpholinyl, tetrahydropyrimidinyl, dioxolinyl, octahydrobenzofuranyl, octahydrobenzimidazolyl, and octahydrobenzothiazolyl.

s. "heterocyclic, optionally substituted" refers to a heterocyclic moiety as defined immediately above, in which up to 4 carbon atoms of the heterocycle moiety may be substituted with a substituent, each substituent is independently selected from the group consisting of halogen, cyano, hydroxy, $(C_1-C_6)$alkyl, $(C_1-C_6)$alkoxy, $(C_1-C_2)$alkyl substituted with one or more halogens, $(C_1-C_2)$ alkoxy substituted with one or more halogens, $SR^8$, and $NR^8R^8$, in which $R^8$ and $R^9$ are as defined above. Any nitrogen atom within such a heterocyclic ring may optionally be substituted with $(C_1-C_6)$ alkyl, if such substitution is chemically permissible.

t. "pharmaceutically acceptable" means suitable for use in mammals.

u. "salts" is intended to refer pharmaceutically acceptable salts and to salts suitable for use in industrial processes, such as the preparation of the compound.

v. "pharmaceutically acceptable salts" is intended to refer to either pharmaceutically acceptable acid addition salts" or "pharmaceutically acceptable basic addition salts" depending upon actual structure of the compound.

w. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

x. "compound of Formula I", "compounds of the invention", and "compounds" are used interchangeably throughout the application and should be treated as synonyms.

y. "patient" refers to warm blooded animals such as, for example, guinea pigs, mice, rats, gerbils, cats, rabbits, dogs, monkeys, chimpanzees, stump tail macques, and humans.

z. "treat" refers to the ability of the compounds to either relieve, alleviate, or slow the progression of the patient's infection or any tissue damage associated with such an infection. Treating also encompasses the administration of a compound prophylatically to prevent the occurrence, or likelihood of developing an infection.

aa. "livestock" refers to animals suitable for human meat consumption. Examples include pigs, cattle, chickens, fish, turkeys, rabbits, etc.

bb. "companion animals" refers to animals kept as pets such as dogs, cats, etc.

cc. "isomer" means "stereoisomer" and "geometric isomer" as defined below.

dd. "stereoisomer" means compounds that possess one or more chiral centers and each center may exist in the R or S configuration. Stereoisomers includes all diastereomeric, enantiomeric and epimeric forms as well as racemates and mixtures thereof.

ee. "geometric isomer" means compounds that may exist in cis, trans, anti, entgegen (E), and zusammen (Z) forms as well as mixtures thereof.

ff. When a bond is represented by a line such as "⋀⋀⋀" this is meant to represent that the bond is the point of attachment between two molecular subunits.

gg. "therapeutically effective amount" is an amount of a compound of the present invention that, when administered to a patient, provides the desired effect; i.e., lessening in the severity of the symptoms associated with a bacterial infection.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

Certain compounds of Formula I are also useful as intermediates for preparing other compounds of Formula I.

Some of the compounds of Formula I are capable of further forming pharmaceutically acceptable acid-addition and/or base salts. All of these forms are within the scope of the present invention.

Thus, pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, acetate, trifluoroacetate, propionate, caprylate, isobutyrate, oxalate, malonate, succinates suberate, sebacate, fumarate, maleate, mandelate, benzoate, chlorobenzoate, methylbenzoate, dinitrobenzoate, phthalate, benzensoulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *Journal of Pharmaceutical Science,* 1977; 66:1-19). The acid addition salt of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., supra., 1977). The base addition salts of said acidic compounds are prepared by contacting the free acid form with a sufficient amount of the desired base to produce the salt in the conventional manner.

All of the compounds of Formula I contain a triazolopyridine ring as depicted below. The numbering system for this ring is shown below:

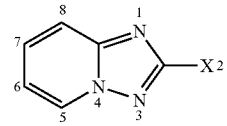

Position 2 of this triazolopyridine ring will always be substituted with a urea, thiourea or a sulfonamide moiety, as depicted by X above. The nitrogen atoms at positions 1, 3, and 4 will not be substituted. Positions 5, 6, 7, and 8 may be optionally substituted as described above.

A more specific embodiment of the invention is the triazolopyridine, or a salt thereof, as described below:

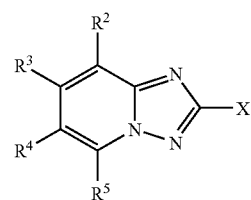

in which

X is represented by —NHC(O)—N-T, in which T is methyl, ethyl, trifluoromethyl, propyl, isopropyl, cyclopropyl, or cyclopropylmethyl;

$R^2$ is represented by hydrogen, methyl, fluoro, chloro, or cyano;

$R^3$ is represented by aryl, heteroaryl, arylalkyl, or heteroarylalkyl;

$R^4$ is represented by hydrogen, methyl, ethyl, isopropyl, cyclopropyl, fluoro, chloro, or cyano, and;

$R^5$ is represented by aryl, heteroaryl, $(CH_2)_zCOOR^6$, $(CH_2)_zCOR^6$, $(CH_2)_zC(NOR^7)R^6$, $(CH_2)_zS(O)R^6$, $(CH_2)_zS(O)_2R^6$, $(CH_2)_zNR^6R^7$, $(CH_2)_zOR^6$, $(CH_2)_z$—$CONR^6R^7$, $(CH_2)_z$—$NR_7$—$SO_2R_6$ or $(CH_2)_z$—$C(O)C(O)NR^6R^7$.

In a more specific embodiment for these compounds,
X is represented by —NHC(O)—N-T, in which T is ethyl
R² is represented by hydrogen,
R³ is phenyl, pyridine, pyrimidine, furan, pyrazole, oxadiazole, or thiofuran, any of which may be optionally substituted,
R⁴ is hydrogen, and,
R⁵ is as above.

A further illustration of the invention, are those compounds, or salts thereof,

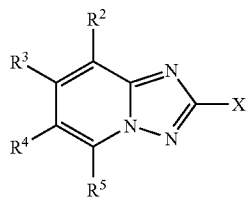

I in which:
X is represented by —NHC(O)—N-T, in which T is methyl, ethyl, trifluoromethyl, propyl, cyclopropyl, cyclopropylmethyl or isopropyl;
R² is represented by aryl, heteroaryl, $(CH_2)_z COOR^6$, $(CH_2)_z$—$CONR^6R^7$ $(CH_2)_z$—$C(O)C(O)NR^6R^7$; $(CH_2)_z COR^6$, $(CH_2)_z C(NOR^7)R^6$, $(CH_2)_z S(O)R^6$, $(CH_2)_z S(O)_2 R^6$, $(CH_2)_z NR^6R^7$, $(CH_2)_z OR^6$ or $(CH_2)_z$—$NR_7$—$SO_2R_6$.
R³ is represented by hydrogen, methyl, ethyl, isopropyl, cyclopropyl, fluoro, chloro, or cyano;
R⁴ is represented by aryl, heteroaryl, arylalkyl, or heteroarylalkyl, and;
R⁵ is represented by hydrogen, methyl, fluoro, chloro, or cyano.

In a more specific embodiment of these compounds,
X is represented by —NHC(O)—N-T, in which T is ethyl
R² is as above,
R³ is hydrogen,
R⁴ is phenyl, pyridine, pyrimidine, furan, pyrazole, oxadiazole or thiofuran, and;
R⁵ is represented by hydrogen.

Specific examples of compounds encompassed by Formula I are depicted below:
1-Ethyl-3-[5-(4-methyl-oxazol-2-yl)-7-pyridin-3-yl-[1,2,4]triazolo[1,5-a]pyridin-2-yl]-urea;
1-Ethyl-3-[5-(methyl-[1,2,4]oxadiazol-5-yl)-7-pyridin-3-yl-[1,2,4]triazolo[1,5-a]pyridin-2-yl]-urea;
1-Ethyl-3-[5-methyl-[1,2,4]oxadiazol-3-yl)-7-pyridin-3-yl-[1,2,4]triazolo[1,5-a]pyridin-2-yl]-urea;
1-Ethyl-3-[5-(5-methyl-1H-[1,2,4]triazol-3-yl)-7-pyridin-3-yl-[1,2,4]triazolo[1,5-a]pyridin-2-yl]-urea;
1-Ethyl-3-[5-(5-methyl-1H-[1,2,4]triazol-3-yl)-7-pyridin-3-yl-[1,2,4]triazolo[1,5-a]pyridin-2-yl]-urea;
1-Ethyl-3-[5-(5-methyl-[1,3,4]oxadiazol-2-yl)-7-pyridin-3-yl-[1,2,4]triazolo[1,5-a]pyridin-2-yl]-urea;
1-Ethyl-3-[5-(5-methyl[1,3,4]thiadiazol-2-yl)-7-pyridin-3-yl-[1,2,4]triazolo[1,5-a]pyridin-2-yl]-urea;
1-Ethyl-3-[5-(4-methyl-thiazol-2-yl)-7-pyridin-3-yl-[1,2,4]triazolo[1,5-a]pyridin-2-yl]-urea;
1-Ethyl-3-[7-pyridin-3-yl-5-(1H-[1,2,3]triazol-4-yl-[1,2,4]triazolo[1,5-a]pyridin-2-yl]-urea;
1-Ethyl-3-(7-pyridin-3-yl-5-[1,2,3]thiadiazol-4-yl-[1,2,4]triazolo[1,5-a]pyridin-2-yl]-urea;
1-Ethyl-3-[5-(4-methyl-1H-imidazol-2-yl)-7-pyridin-3-yl-[1,2,4]triazolo[1,5-a]pyridin-2-yl]-urea;
1-Ethyl-3-[5-(2-methyl-oxazol-5-yl)-y-pyridin-3-yl-[1,2,4]triazolo[1,5-a]pyridin-2-yl]-urea;
1-Ethyl-3-[5-(2-methyl-1H-imidazol-4-yl)-7-pyridin-3-yl-[1,2,4]triazolo[1,5-a]pyridin-2-yl]-urea;
1-[5-(2-Dimethylamino-acetyl)-7-pyridin-3-yl-[1,2,4]triazolo[1,5-a]pyridin-2-yl]-3-ethyl-urea
1-[5-Acetyl-7-pyridin-3-yl-[1,2,4]triazolo[1,5-a]pyridin-2-yl]-3-ethyl-urea;
1-Ethyl-3-(5-propionyl-7-pyridin-3-yl-[1,2,4]triazolo[1,5-a]pyridin-2-yl]-urea;
1-Ethyl-3-[5-(1-methoxyimino-propyl)-7-pyridin-3-yl-[1,2,4]triazolo[1,5-a]pyridin-2-yl]-urea;
1-Ethyl-3-[5-(1-methoxyimino-ethyl)-7-pyridin-3-yl-[1,2,4]triazolo[1,5-a]pyridin-2-yl]-urea;
1-[5-(2-Dimethylamino-1-methoxyimino-ethyl)-7-pyridin-3-yl-[1,2,4]triazolo[1,5-a]pyridin-2-yl]-3-ethyl-urea;
1-Ethyl-3-[5-(1-methoxyimino-2-methyl-propyl)-7-pyridin-3-yl-[1,2,4]triazolo[1,5-a]pyridin-2-yl]-urea;
2-(3-Ethyl-ureido)-7-3-yl-[1,2,4]triazolo[1,5-a]pyridine-5-sulfonic acid amide;
1-Ethyl-3-(5-isobutyryl-7-pyridin-3-yl-[1,2,4]triazolo[1,5-a]pyridin-2-yl)-urea;
1-(5-Dimethylamino-7-pyridin-3-yl-[1,2,4]triazolo[1,5-a]pyridin-2-yl)-3-ethyl-urea;
1-Ethyl-3-(5-methanesulfonyl-7-pyridin-3-yl-[1,2,4]triazolo[1,5-a]pyridin-2-yl)-urea;
1-Ethyl-3-[5-(4-methyl-oxazol-2-yl)-7-pyridin-3-yl-[1,2,4]triazolo[1,5-a]pyridin-2-yl]-urea;
1-Ethyl-3-[5-(3-methyl-[1,2,4]oxadiazol-5-yl)-7-pyridin-3-yl-[1,2,4]triazolo[1,5-a]pyridin-2-yl]-urea;
1-Ethyl-3-[5-(-methyl-[1,2,4]oxadiazol-3-yl]-7-pyridin-3-yl-[1,2,4]triazolo[1,5-a]pyridin-2-yl]-urea;
1-Ethyl-3-[5-(5-methyl-1H-[1,2,4]triazol-3-yl)-7-pyridin-3-yl-[1,2,4]triazolo[1,5-a]pyridin-2-yl]-urea;
1-Ethyl-3-[5-(5-methyl-[1,3,4]oxadiazol-2-yl)-7-pyridin-3-yl-[1,2,4]triazolo[1,5-a]pyridin-2-yl]-urea;
1-Ethyl-3-[5-(5-methyl-[1,2,4]thiadiazol-2-yl)-y-pyridin-3-yl-[1,2,4]triazolo[1,5-a]pyridin-2-yl]-urea;
1-Ethyl-3-[5-(4-methyl-thiazol-2-yl)-7-pyridin-3-yl-[1,2,4]triazolo[1,5-a]pyridin-2-yl]-urea;
1-Ethyl-3-[7-pyridin-3-yl-5-(1H-[1,2,3]triazolo-4-yl)-[1,2,4]triazolo[1,5-a]pyridin-2-yl]-urea;
1-Ethyl-3-(7-pyridin-3-yl-5-[1,2,3]thiadiazol-4-yl-[1,2,4]triazolo[1,5-a]pyridin-2-yl]-urea;
1-Ethyl-3-[5-(4-methyl-1H-imidazol-2-yl)-70pyridin-3-yl-[1,2,4]triazolo[1,5-a]pyridin-2-yl]-urea;
1-Ethyl-3-[5-(2-methyl-1Himidazol-4-yl)-y-pyridin-3-yl-[1,2,4]triazolo[1,5-a]pyridin-2-yl]-urea;
1-[5-(2-Dimethylamino-acetyl)-7-pyridin-3-yl-[1,2,4]triazolo[1,5-a]pyridin-2-yl]-3-ethyl-urea;
1-(5-Acetyl-7-pyridin-3-yl-[1,2,4]triazolo[1,5-a]pyridin-2-yl)-3-ethyl-urea;
1-Ethyl-3-(5-propionyl-7-pyridin-3-yl-[1,2,4]triazolo[1,5-a]pyridin-2-yl)-urea;
1-Ethyl-3-[5-(1-methoxyimino-porpyl)-7-pyridin-3-yl-[1,2,4]triazolo[1,5-a]pyridin-2-yl]-urea;
1-Ethyl-2-[5-(1-methoxyimino-propyl)-7-pyridin-3-yl-[1,2,4]triazolo[1,5-a]pyridin-2-yl]-urea;
1-[5-(2-Dimethylamino-1-methoxyimino-ethyl)-7-pyridin-3-yl-[1,2,4]triazolo[1,5-a]pyridin-2-yl]-3-ethyl-urea;
1-(5-Dimethylaminomethyl-7-pyridin-3-yl-[1,2,4]triazolo[1,5-a]pyridin-2-yl)-3-ethyl-urea;
1-[5-(2-Dimethylamino-ethoxy)-7-pyridin-3-yl-[1,2,4]triazolo[1,5-a]pyridin-2-yl]-3-ethyl-urea;
1-Ethyl-3-(5-methanesulfonylmethyl-7-pyridin-3-yl-1,2,4]triazolo[1,5-a]pyridin-2-yl)-urea;

[2-(3-Ethyl-ureido)-7-pyridin-3-yl-[1,2,4]triazolo[1,5-a]pyridin-5-yl]-methanesulfonamide;
1-Ethyl-3-(7-pyridin-3-yl-5-pyrimidin-2-yl-[1,2,4]triazolo[1,5-a]pyridin-2-yl)-urea;
1-Ethyl-3-(7-pyridin-3-yl-5-pyrimidin-5-yl-[1,2,4]triazolo[1,5-a]pyridin-2-yl)-urea;
N-[2-(3-Ethyl-ureido)-7-pyridin-3-yl-[1,2,4]triazolo[1,5-a]pyridin-5-ylmethyl]-acetamide;
1-Ethyl-3-[5-(3-hydroxy-pyrrolidin-1-yl)-y-pyridin-3-yl-[1,2,4]triazolo[1,5-a]pyridin-2-yl]-urea;
1-Ethyl-3-[5-(3-hydroxy-pyrrolidin-1-yl)-7-pyridin-3-yl-[1,2,4]triazolo[1,5-a]pyridin-2-yl]-urea;
1-Ethyl-3-[5-(3-hydroxy-pyrrolidin-1-ylmethyl)-7-pyridin-3-yl-[1,2,4]triazolo[1,5-a]pyridin-2-yl]-urea;
N-[2-(3-Ethyl-ureido)-7-pyridin-3-yl-[1,2,4]triazolo[1,5-a]pyridin-5-ylmethyl]-methanesulfonamide;
1-Ethyl-3-(7-pyridin-3-yl-5-pyrrolidin-1-ylmethyl-[1,2,4]triazolo[1,5-a]pyridin-2-yl)-urea;
1-Ethyl-3-(7-pyridin-3-yl-5-pyrrolidin-1-yl-[1,2,4]triazolo[1,5-a]pyridin-2-yl)-urea;
N-[2-(3-Ethyl-ureido)-7-pyridin-3-yl-[1,2,4]triazolo[1,5-a]pyridin-5-yl]-isobutyramide;
1-(5-Diethylaminomethyl-7-pyridin-3-yl-[1,2,4]triazolo[1,5-a]pyridin-2-yl)-3-ethyl-urea;
1-Ethyl-3-(5-piperidin-1-ylmethyl-7-pyridin-3-yl-[1,2,4]triazolo[1,5-a]pyridin-2-yl)-urea;
1-Ethyl-3-(5-morpholin-4-ylmethyl-7-pyridin-3-yl-[1,2,4]triazolo[1,5-a]pyridin-2-yl)-urea;
1-Ethyl-3-[5-(3-hydroxy-azetidin-1-ylmethyl)-7-pyridin-3-yl-[1,2,4]triazolo[1,5-a]pyridin-2-yl-urea;
1-Ethyl-3-(5-methylsulfanylmethyl-7-pyridin-3-yl-[1,2,4]triazolo[1,5-a]pyridin-2-yl)-urea;
1-Ethyl-3-(5-methoxymethyl-7-pyridin-3-yl-[1,2,4]triazolo[1,5-a]pyridin-2-yl)-urea;
1-(5-Benzenesulfonylmethyl-7-pyridin-3-yl-[1,2,4]triazolo[1,5-a]pyridin-2-yl)-4-ethyl-urea;
1-(5-Aminomethyl-7-pyridin-3-yl-[1,2,4]triazolo[1,5-a]pyridin-2-yl)-urea;
1-Ethyl-3-(5-methyl-7-pyridin-3-yl-[1,2,4]triazolo[1,5-a]pyridin-2-yl)-urea;
1-Ethyl-3-5-[5-(piperidine-1-carbonyl)-7-pyridin-3-yl-[1,2,4]triazolo[1,5-a]pyridin-2-yl]-urea;
1-Ethyl-3-5-(furan-2-carbonyl)-7-pyridin-3-yl-[1,2,4]triazolo[1,5-a]pyridin-2-yl]-urea;
1-(5-Cyanomethyl-7-pyridin-3-yl-[1,2,4]triazolo[1,5-a]pyridin-2-yl)-3-ethyl-urea;
1-(5-Cyclopropanecarbonyl-7-pyridin-3-yl-[1,2,4]triazolo[1,5-a]pyridin-2-yl)-3-ethyl-urea;
1-(5-Benzoyl-7-pyridin-3-yl-[1,2,4]triazolo[1,5-a]pyridin-2-yl)-3-ethyl-urea;
1-(5-Cyclopentanecarbonyl-7-pyridin-3-yl-[1,2,4]triazolo[1,5-a]pyridin-2-yl)-3-ethyl-urea;
1-Ethyl-3-(5-phenylacetyl-7-pyridin-3-yl-[1,2,4]triazolo[1,5-a]pyridin-2-yl)-urea;
1-Ethyl-3-[5-(furan-2-yl-methoxyimino-methyl)-70-pyridin-3-yl-[1,2,4]triazolo[1,5-a]pyridin-2-yl]-urea;
1-Ethyl-3-[7-pyridin-3-yl-5-(2-pyridin-3-yl-acetyl)-[1,2,4]triazolo[1,5-a]pyridin-2-yl]-urea;
1-[5-(Cyclopentyl-methoxyimino-methyl)-7-pyridin-3-yl-[1,2,4]triazolo[1,5-a]pyridin-2-yl]-3-ethyl-urea;
1-Ethyl-3-[5-(methoxyimino-phenyl-methyl)-7-pyridin-3-yl-[1,2,4]triazolo[1,5-a]pyridin-2-yl]-urea;
1-[5-(Cyclopropyl-methoxyimino-methyl)-7-pyridin-3-yl-[1,2,4]triazolo[1,5-a]pyridin-2-yl]-3-ethyl-urea;
1-Ethyl-3-[5-(3-isopropyl-[1,2,4]oxadiazol-5-yl)-7-pyridin-3-yl-[1,2,4]triazolo[1,5-a]pyridin-2-yl]-urea;
1-[5-(5-Cyclopropyl-[1,2,4]oxadiazol-3-yl)-7-pyridin-3-yl-[1,2,4]triazolo[1,5-a]pyridin-2-yl]-3-ethyl-urea;
1-Ethyl-3-[5-(3-ethyl-[1,2,4]oxadiazol-5-yl)-7-pyridin-3-yl-[1,2,4]triazolo[1,5-a]pyridin-2-yl]-urea;
1-Ethyl-3-[5-(5-isopropyl-[1,3,4]oxadiazol-2-yl)-7-pyridin-3-yl-[1,2,4]triazolo[1,5-a]pyridin-2-yl]-urea;
1-Ethyl-3-[5-(5-isopropyl-[1,3,4]thiadiazol-2-yl)-7-pyridin-3-yl-[1,2,4]triazolo[1,5-a]pyridin-2-yl]-urea;
1-Ethyl-3-[5-(5-idopropyl-[1,3,4]thiadiazol-2-yl-7-pyridin-3-yl-[1,2,4]triazolo[1,5-a]pyridin-2-yl]-urea;

Synthesis

The triazolopyridines of Formula I can be prepared using the synthetic procedures depicted below

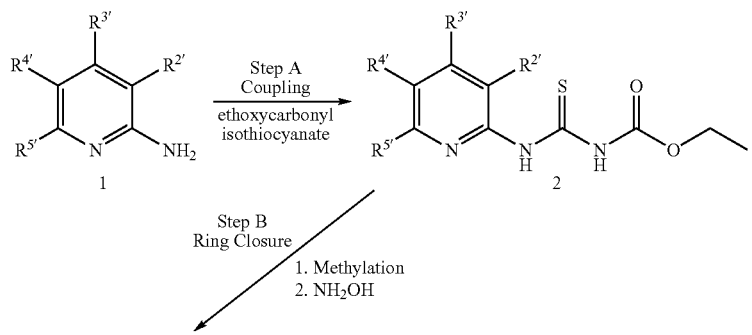

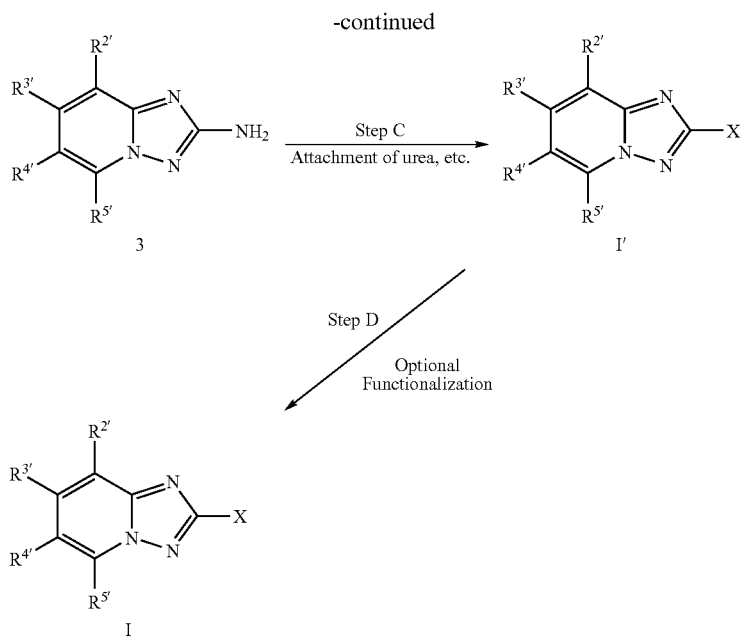

in Reaction Scheme I.

The starting material for the triazolopyridine is the 2-aminopyridine, described by Structure 1. In this pyridine, $R^{2'}$, $R^{3'}$, $R^{4'}$, and $R^{5'}$ are represented by: 1) the same substituent as is desired in the final product, 2) a reactive substrate such as a halogen atom, hydroxyl group, or amine group that will facilitate the coupling of the desired substituent onto the triazolopyridine core in a subsequent reaction, or 3) a protecting group that is removed after formation of the triazolopyridine core and further manipulated to achieve the desired triazolopyridine. One skilled in the art can determine the most efficient way of synthesizing the desired molecule.

In Step A, the 2-amino pyridine is contacted with at least one equivalent of ethoxycarbonyl isothiocyanate in order to form the 2-thiourea pyridine of Structure 2 in which $R^{2'}$-$R^{5'}$ are as above. The reaction is typically carried out at room temperature, in a solvent such as dioxane. The reactants are stirred for a sufficient period of time to complete the reaction, which may vary from 5 minutes to 24 hours, depending upon the temperature of the reaction, the quantity of reactants, etc. After completion, the desired product of structure 2 is recovered by filtration, evaporation, etc., as is known in the art. It may optionally be purified by chromatography as is known in the art prior to carrying out Step B.

In Step B, the triazolopyridine core is formed by methylating the thio group of the thiourea with an appropriate methylation agent, such as methyl iodide, then contacting the methylthiol with about one equivalent of hydroxylamine, in the presence of a weak base such as diisopropylamine. The reaction is typically carried out in an alcoholic solvent, at a temperature ranging from room temperature to reflux. The reactants are stirred for a sufficient period of time to complete the reaction, which may vary from 5 minutes to 24 hours, depending upon the quantity of reactants, the reaction temperature, etc. The triazolopyridine core of structure 3 may be recovered by filtration, evaporations, etc., as is known in the art. It may optionally be purified by chromatography prior to its utilization in the coupling reaction depicted in Step C.

In Step C, the side chain depicted by X is attached to the 2-position of the triazolopyridine core. If X is represented by a urea moiety or thiourea moiety, then an excess of a reactant represented by $NH_2$—$C(J)$-$T$-$R^1$, in which J, T, and $R^1$ are represented by the same substituent as required in the final product, is contacted with the triazolopyridine core of structure 3, in which $R^{2'}$-$R^{5'}$ are as defined above. The reactants are contacted and stirred in an aprotic solvent such as tetrahydrofuran, possibly in the presence of a catalyst, such as dibutyltindiacetate, at elevated temperatures, typically reflux. The reaction is carried out for a period of time ranging from 5 minutes to 24 hours. The resulting triazolopyridine of Formula I' may be recovered by filtration, evaporation or other techniques as is known in the art. It may optionally be purified by flash chromatography, or other techniques known in the art.

If X is represented by NH—$SO_2$—NH—$R^1$, then an excess of a reactant represented by $C_1$—$SO_2$—$NR^1$, is contacted with the triazolopyridine core of structure 3, in which $R^{2'}$-$R^{5'}$ are as defined above. The reactants are contacted and stirred in an aprotic solvent, such as dichloromethane, in the presence of base such as pyridine at lowered temperatures, or at room temperature. The reaction is carried out for a period of time ranging from 5 minutes to 24 hours. The resulting triazolopyridine of Formula I' may be recovered by filtration, evaporation or other techniques as is known in the art. It may optionally be purified by flash chromatography, or other techniques known in the art. (Bioorganic and Medicinal Chemistry Letters 2004, 14, 3235-3240).

Depending upon the desired final product and the specific substituents $R^{2'}$-$R^{5'}$ represent, the reaction may be complete. If any of $R^{2'}$-$R^{5'}$ do not represent the substituent required in the final product, then optional Step D should be carried out. The actual reaction will vary depending upon the particular substituent being placed on the triazolopyridine core. However, the coupling of the various functional groups described by $R^{2'}$-$R^{5'}$ onto heteroaryl cores is known in the art. The reader's attention is directed to *Angewandte Chemie*, International Edition 2002, 41(22), 4176-4211 for guidance on such reactions.

By way of illustrative example, methods for converting carboxylic esters into oxadiazoles or thiadiazoles are described in Synthesis 2003, 6, 899-905; Journal of Medicinal Chemistry 1991, 34(1), 140-151; Indian Journal of Heterocyclic Chemistry 2002, 12(3), 289-290. Likewise, the conversion of carboxylic esters into oxazoles is described in Synthesis 1998, (9), 1298-1304; Journal of Organic Chemistry 1989, 54(2), 431-434. Methods for preparing triazoles is described in Journal of the Chemical Society, Dalton Transactions 2002, (8), 1740-1746. Ketones, oximes and other carbonyl containing compounds can be prepared from the corresponding carboxylic esters using methods known in the art. These reactions are being described to illustrate the invention.

Medical and Veterinary Uses

The compounds may be used for the treatment or prevention of infectious disorders caused by a variety of bacterial organisms. Examples include Gram positive and Gram negative aerobic and anaerobic bacteria, including Staphylococci, for example *S. aureus*; Enterococci, for example *E. faecalis*; Streptococci, for example *S. pneumoniae; Haemophilus*, for example *H. influenza; Moraxella*, for example *M. catarrhalis*; and *Escherichia*, for example *E. coli*. Other examples include Mycobacteria, for example *M. tuberculosis*; intercellular microbes, for example *Chlamydia* and Rickettsiae; and *Mycoplasma*, for example *M. pneumoniae*.

Examples of infections that may be treated with the compounds of Formula I include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

In order to exhibit this anti-infective activity, the compounds need to be administered in a therapeutically effective amount. By a "therapeutically effective amount", is meant a sufficient quantity of the compound to treat the infection, at a reasonable benefit/risk ratio applicable to any such medical treatment. It will be understood, however, that the attending physician, within the scope of sound medical judgment, will decide the total daily dosage of the compound. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. As a general guideline however, the total daily dose will typically range from about 0.1 mg/kg/day to about 500 mg/kg/day in single or in divided doses. Typically, dosages for humans will range from about 10 mg to about 2000 mg per day, in a single or multiple doses.

Any route typically used to treat infectious illnesses, including oral, parenteral, topical, rectal, transmucosal, and intestinal, can be used to administer the compounds. Parenteral administrations include injections to generate a systemic effect or injections directly into to the afflicted area. Examples of parenteral administrations are subcutaneous, intravenous, intramuscular, intradermal, intrathecal, and intraocular, intranasal, intravetricular injections or infusions techniques. Topical administrations include the treatment of areas readily accessibly by local application, such as, for example, eyes, ears including external and middle ear infections, vaginal, open wound, skin including the surface skin and the underneath dermal structures, or other lower intestinal tract.

Transmucosal administration includes nasal aerosol or inhalation applications.

Formulations

Compounds of the invention can be formulated for administration in any convenient way for use in human or veterinary medicine, by analogy with other bioactive agents such as antibiotics. Such methods are known in the art and are summarized below.

The composition can be formulated for administration by any route known in the art, such as subdermal, by-inhalation, oral, topical or parenteral. The compositions may be in any form known in the art, including but not limited to tablets, capsules, powders, granules, lozenges, creams or liquid preparations, such as oral or sterile parenteral solutions or suspensions.

The topical formulations of the present invention can be presented as, for instance, ointments, creams or lotions, opthalmic ointments/drops and otic drops, impregnated dressings and aerosols, and may contain appropriate conventional additives such as preservatives, solvents to assist drug penetration and emollients, etc. Such topical formulations may also contain conventional carriers, such as cream or ointment bases and ethanol or oleyl alcohol for lotions. Such carriers may be present, for example, from about 1% up to about 98% of the formulation.

Tablets and capsules for oral administration may be in unit dose presentation form, and may contain conventional excipients such as binding agents, for example acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods will known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerin, propylene glycol, or ethyl alcohol; preservatives, for example methyl or propyl p-hydroxybenzoate or sorbic acid, and, if desired, conventional flavoring or coloring agents.

For parenteral administration, fluid unit dosage forms are prepared utilizing the compound and a sterile vehicle, water being typical. The compound, depending on the vehicle and concentration used, can be either suspended or dissolved in the vehicle or other suitable solvent. In preparing solutions, the compound can be dissolved in water for injection and filter sterilized before filling into a suitable vial or ampoule and sealing. Advantageously, agents such as a local anesthetic preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain, for example, from about 0.1% by weight, to about 60% by weight, of the active material, depending on the method of administration. Where the compositions comprise dosage units, each unit will contain, for example, from about 5-500 mg of the active ingredient. The dosage as employed for adult human treatment will range, for example, from about 10 to 3000 mg per day, depending on the route and frequency of administration.

The following examples are being provided to illustrate but not limit the claimed invention.

EXAMPLES

In the discussion above and in the examples below, the following abbreviations have the following meanings. If an abbreviation is not defined, it has its generally accepted meaning.

| | |
|---|---|
| bm = | broad multiplet |
| BOC = | tert-butoxycarbonyl |
| bd = | broad doublet |
| bs = | broad singlet |
| CDI = | 1,1'-carbonyldiimidazole |
| d = | doublet |
| dd = | doublet of doublets |
| dq = | doublet of quartets |
| dt = | doublet of triplets |
| DMF = | dimethylformamide |
| DMA = | dimethylacetamide |
| DMAP = | dimethylaminopyridine |
| DMSO = | dimethyl sulfoxide |
| eq. = | equivalents |
| g = | grams |
| h = | hours |
| HPLC = | high pressure liquid chromatography |
| LG = | leaving group |
| m = | multiplet |
| M = | molar |
| M % = | mole percent |
| max = | maximum |
| meq = | milliequivalent |
| mg = | milligram |
| mL = | milliliter |
| mm = | millimeter |
| mmol = | millimol |
| q = | quartet |
| s = | singlet |
| t or tr = | triplet |
| TBS = | tert-butyldimethylsilyl |
| TFA = | trifluoroacetic acid |
| THF = | tetrahydrofuran |
| TLC = | thin layer chromatography |
| p-TLC = | preparative thin layer chromatography |

| | |
|---|---|
| -continued | |
| μL = | microliter |
| N = | normality |
| MeOH = | methanol |
| DCM = | dichloromethane |
| HCl = | hydrochloric acid |
| ACN = | acetonitrile |
| MS = | mass spectrometry |
| rt = | room temperature |
| EtOAc = | ethyl acetate |
| EtO = | ethoxy |
| Ac = | acetate |
| NMP = | 1-methyl-2-pyrrolidinone |
| μL = | microliter |
| J = | coupling constant |
| NMR = | Nuclear magnetic resonance |
| MHz = | megahertz |
| Hz = | hertz |
| m/z = | mass to charge ratio |
| min = | minutes |
| Boc = | tert-butyloxycarbonyl |
| CBZ = | benzyloxycarbonyl |
| DCC = | 1,3-dicyclohexylcarbodiimide |
| PyBop = | benzotriazole-1-yl-oxy-trispyrrolidinophosphonium hexafluorophosphate |
| Pd(dppf)Cl$_2$ = | Bis(diphenylphosphino)ferrocenepalladium(II) chloride |
| Et$_2$O = | diethyl ether |
| NaOAc = | sodium acetate |
| AcOH = | acetic acid |
| dppf = | 1,1'-Bis(diphenylphosphino)ferrocene |
| PdCl$_2$ = | Palladium (II) chloride |
| MPLC = | medium pressure liquid chromatography |
| DME = | dimethoxyethane |
| PhMe = | toluene |
| KOAc = | potassium acetate |
| TosNCO = | p-toluenesulfonyl isocyanate |
| EtNH$_2$ = | ethylamine |
| Lawesson's reagent = | 2,4-Bis(4-methoxyphenyl)-1,3,2,4-dithiadiphosphetane 2,4-disulfide |

Example 1

1-Ethyl-3-(7-pyridin-3-yl-[1,2,4]triazolo[1,5-a]pyridin-2-yl)-urea

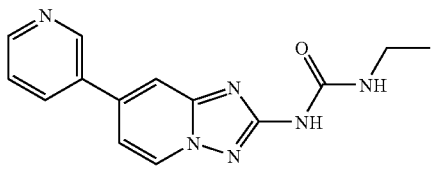

Step 1:

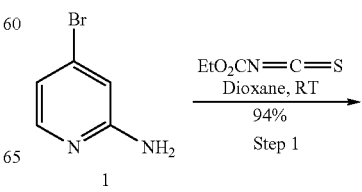

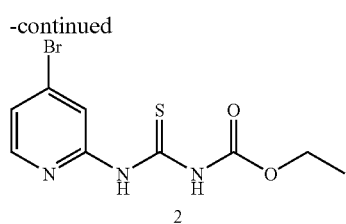

2-Amino-4-bromopyridine (1) (200 mg, 1.16 mmol) was dissolved in dioxane (4 mL) and the flask flushed with nitrogen. Freshly prepared ethoxycarbonyl isothiocyanate [*J. Org. Chem.*, 46, 3415-3420 (1981)] (152 mg, 1.16 mmol) was then added dropwise and the reaction mixture stirred at room temperature for 15 hours. The reaction solvent was removed under reduced pressure to give a solid which was purified by filtration through a plug of silica gel (50% EtOAc/hexanes as eluant) to give the desired compound thiourea 2. (APCI$^+$) 304, 306.

Step 2:

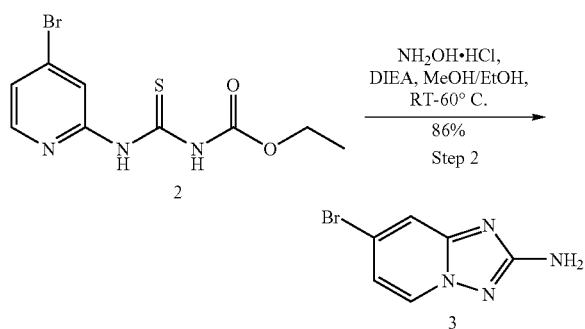

To a stirred suspension/solution of hydroxylamine hydrochloride (375 mg, 5.40 mmol) and diisopropylethylamine (419 mg, 3.24 mmol) in MeOH/EtOH (1:1, 2 mL) was added compound 2 as a solid. This mixture was stirred at room temperature for 2 h, giving a pale yellow suspension, followed by a further 3 h, at 60° C. The reaction mixture was allowed to cool, diluted with CH$_2$Cl$_2$ (100 mL), which was then washed with water (2×80 mL) and brine (80 mL). This solution was dried (Na$_2$SO$_4$) and the solvent removed under reduced pressure to give 7-bromo-[1,2,4]triazolo[1,5-a]pyridin-2-ylamine (3) LCMS (APCI$^+$) 213, 215.

Step 3:

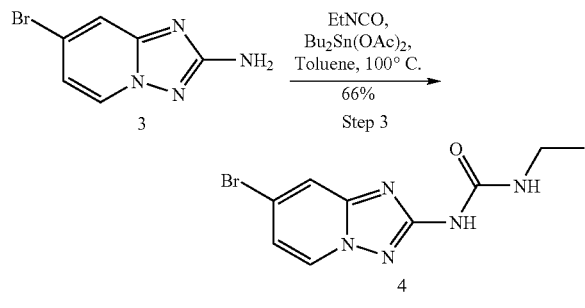

7-Bromo-[1,2,4]triazolo[1,5-a]pyridin-2-ylamine (compound 3, 1.22 g, 5.73 mmol) was dissolved in THF/toluene (1:1, 60 mL), then ethyl isocyanate (4.07 g, 57.3 mmol) and a catalytic quantity of dibutyltindiacetate (6 drops) were added to the mixture. The reaction was then heated in a sealed tube at 100° C. for 24 h. This mixture was allowed to cool, then the solvents removed under reduced pressure to afford an oily solid, which was triturated with Et$_2$O, giving a solid which was collected by filtration. Further material was isolated by flash chromatography of the resulting filtrate on silica (2% MeOH/CH$_2$Cl$_2$ as eluant) to give compound 1-(7-bromo-[1,2,4]triazolo[1,5-a]pyridin-2-yl)-3-ethyl-urea (4) LCMS (APCI$^+$) 284, 286.

Step 4:

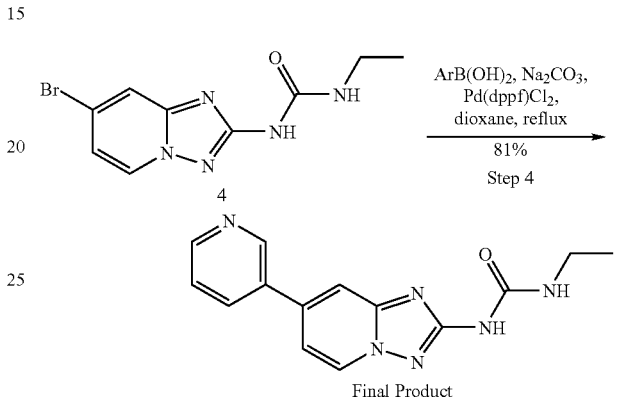

1-(7-Bromo-[1,2,4]triazolo[1,5-a]pyridin-2-yl)-3-ethyl-urea (4) (80 mg, 0.28 mmol) was dissolved in dioxane (2 mL), to which was added 2 M Na$_2$CO$_3$ (0.30 mL) and 3-pyridinylboronic acid (38 mg, 0.31 mmol). Pd(dppf)Cl$_2$ (13 mg) was added last, and the mixture heated under nitrogen at reflux for 1.5 h. The reaction solvent was removed under reduced pressure and the residue filtered through a plug of silica gel (5% MeOH/CH$_2$Cl$_2$ as eluant) to give a solid, which was triturated with Et$_2$O. 1-Ethyl-3-(7-pyridin-3-yl-[1,2,4]triazolo[1,5-a]pyridin-2-yl)-urea was isolated mp. 230-233° C.

Example 1A

5-Chloro-7-pyridin-3-yl-[1,2,4]triazolo[1,5-a]pyridin-2-ylamine

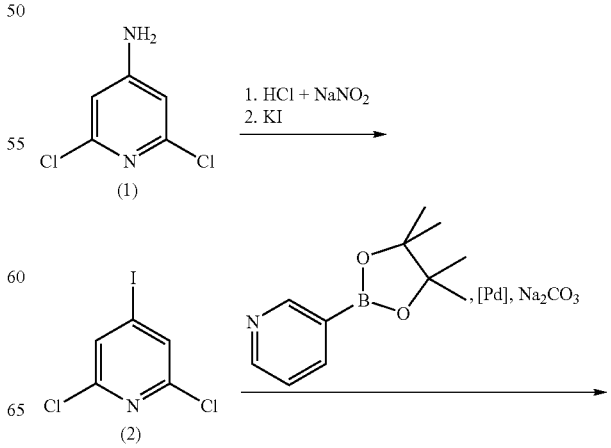

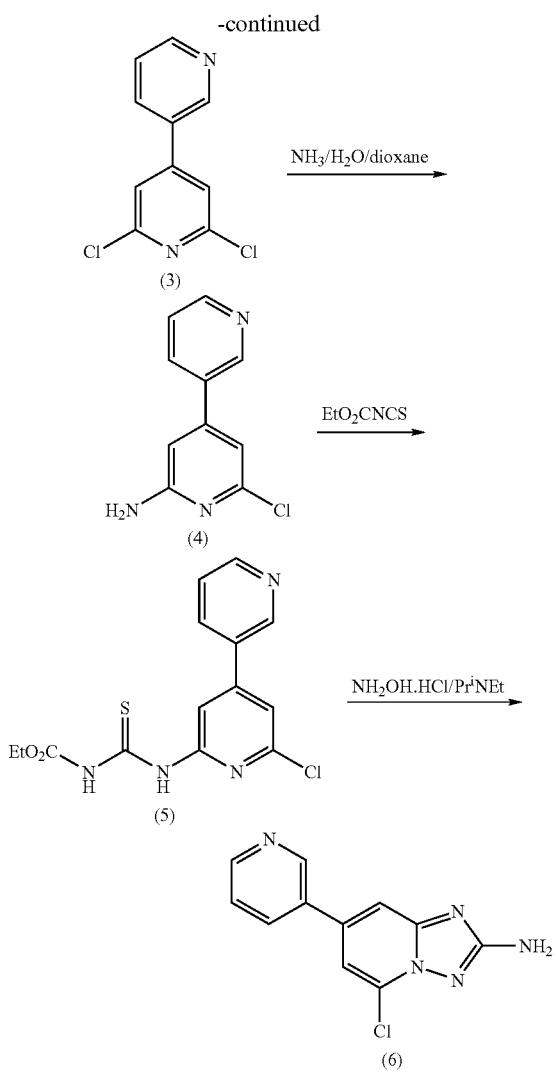

Step 1:

Compound (1) (90 g, 0.552 mol) was taken up in acetonitrile (900 mL) and water (1600 mL) in a 5-L flask equipped for mechanical stirring. HCl (conc.) (450 mL, 5.5 mol) was added all at once and the mixture was cooled to −4 to −5° C. A solution of NaNO$_2$ (76.2 g, 1.10 mol) in 250 mL H$_2$O was added in a dropwise fashion over 5 min. The mixture was warmed to 0° C. over 0.5 h. KI (275 g, 1.66 mol) in H$_2$O (500 mL) was added dropwise over 20 min whilst keeping the temperature at −1 to +1° C. The resulting mixture was warmed to 16° C., then cooled in an ice bath. NH$_3$ (28-30% in H$_2$O, 250 mL) was added whilst keeping the temperature at or below 15° C. The pH of the mixture was 8 after this addition. The dark brown organics were extracted into Et$_2$O (ca. 6 L). The Et$_2$O extracts were washed with an aqueous NaHSO$_3$ solution until a light orange solution was obtained which was then finally washed with a small volume of saturated brine. Drying (MgSO$_4$), filtration and removal of solvent afforded compound (2) which was employed crude in the next step of the reaction.

Step 2:

3-Pyridine boronic acid pinacolate ester (89.8 g, 0.438 mol), compound (2) (100 g, 0.365 mol) and Na$_2$CO$_3$ (116.1 g, 1.095 mol) were taken up in a mixture of toluene (1.2 L), H$_2$O (0.6 L) and EtOH (0.6 L) in a 5-L flask equipped for mechanical stirring. The orange mixture was degassed with a N$_2$ purge over 0.5 h, then [Pd(PPh$_3$)$_4$] (4.22 g, 3.65 mmol) was added. The mixture was brought to reflux for 36 h. On cooling, the solvent was stripped by rotary evaporation and the residue was separated between H$_2$O and EtOAc. The organic extracts were washed with a small volume of saturated brine, then dried (MgSO$_4$), filtered and reduced to dryness by rotary evaporation. The 95 g of orange solid thus obtained was dissolved in DCM (200 mL). Hexane (600 mL) was added to this solution with stirring on an ice bath. The resulting cream solid was collected after 1 h by filtration. Analysis by $^1$H NMR showed this to be pure (3). A further 6 g of pure compound (3) was obtained by recrystallization of the mother liquors.

Step 3:

A suspension of compound (3) (35 g, 156 mmol) in dioxane (250 mL) was treated with NH$_3$ (28-30% in H$_2$O, 350 mL). The steel bomb containing the mixture was sealed and heated at 135-150° C. (internal temperature) for 48 h. On cooling, the contents of the bomb were poured onto saturated brine (300 mL) and the organic material was extracted into EtOAc (ca. 3 L). The combined organic extracts were dried (Na$_2$SO$_4$), filtered and reduced to compound (4) which was assessed to be sufficiently pure to be employed crude in the next step of the reaction.

Step 4:

A suspension of compound (4) (31.5 g, 153 mmol) in dioxane (1 L) was treated all at once with EtO$_2$CNCS (22 g, 169 mmol). After stirring 48 h at room temperature, 1.8 L of hexane was added and the resulting colourless precipitate was collected by filtration, washed with hexane and dried in vacuo to yield compound (5).

Step 5:

NH$_2$OH.HCl (18.1 g, 260 mmol) in EtOH (500 mL) was treated with Pr$^i$NEt (34 g, 260 mmol). After stirring for 5 min at room temperature, compound (5) (29.2 g, 86.8 mmol) was added all at once and the resulting suspension was brought rapidly to reflux under N$_2$. After 3 h, the mixture was cooled on an ice bath and the resulting solid was collected by filtration, washed with a small volume of EtOH and dried in vacuo to yield compound (6). APCI-MS Found: [M+H]=246, 248.

Example 2

1-Ethyl-3-[7-(6-methoxy-pyridin-3-yl)-[1,2,4]triazolo[1,5-a]pyridin-2-yl]-urea

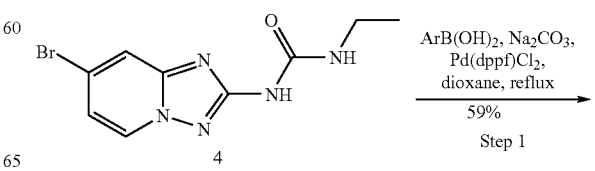

Step 1

-continued

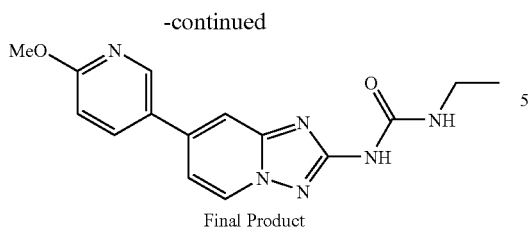

Final Product

Compound 4, prepared as in Example 1, (120 mg, 0.42 mmol) was dissolved in dioxane (5 mL), to which was added $Na_2CO_3$ (0.50 mL of a 2 M aqueous solution) and 3-methoxy-5-pyridineboronic acid (107 mg, 0.70 mmol). $Pd(dppf)Cl_2$ (38 mg) was added last, and the mixture heated under nitrogen at reflux for 15 h. The reaction solvent was removed and the residue filtered through a plug of silica gel (gradient 2-5% $MeOH/CH_2Cl_2$ as eluant) to give a solid which was triturated with $Et_2O$. 1-Ethyl-3-[7-(6-methoxy-pyridin-3-yl)-[1,2,4]triazolo[1,5-a]pyridin-2-yl]-urea was isolated mp. 230-233° C. Anal. calcd for $C_{15}H_{16}N_6O_2$: C, 57.7; H, 5.2; N, 26.9. Found: C, 57.6; H, 5.2; N, 26.4.

Example 3

1-Ethyl-3-[7-(2-methoxy-pyrimidin-5-yl)-[1,2,4]triazolo[1,5-a]pyridin-2-yl]-urea Using the general procedure of Example 2, but substituting 3-methoxy-5-pyrimidineboronic acid for 3-methoxy-5-pyridineboronic acid, the title compound was isolated mp. 243-248° C. Anal. calcd for $C_{14}H_{15}N_7O_2 \cdot 0.5H_2O$: C, 52.2; H, 5.0; N, 30.4. Found: C, 52.2; H, 4.7; N, 30.3.

Example 4

1-[7-(6-Dimethylamino-pyridin-3-yl)-[1,2,4]triazolo[1,5-a]pyridin-2-yl]-3-ethyl-urea Using the general procedure of Example 2, but substituting 2-(dimethylamino)-5-pyrimidineboronic acid for 3-methoxy-5-pyridineboronic acid the title compound was isolated mp. 285-290° C. Anal. calcd for $C_{15}H_{18}N_8O$: C, 55.2; H, 5.6; N, 34.3. Found: C, 55.2; H, 5.5; N, 34.3.

Example 5

1-Ethyl-3-(7-pyrimidin-5-yl-[1,2,4]triazolo[1,5-a]pyridin-2-yl)-urea

Using the general procedure of Example 2, but substituting pyrimdine-5-boronic acid for 3-methoxy-5-pyridineboronic acid the title compound was obtained.
Anal. calcd for $C_{13}H_{13}N_7O \cdot 0.25H_2O$: C, 54.3; H, 4.7; N, 34.1. Found: C, 54.3; H, 4.6; N, 33.8.

Example 6

2-(3-Ethyl-ureido)-7-pyridin-3-yl-[1,2,4]triazolo[1,5-a]pyridine-5-carboxylic acid methyl ester

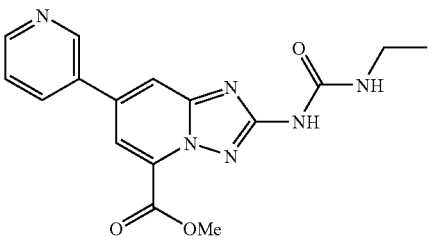

Step 1:

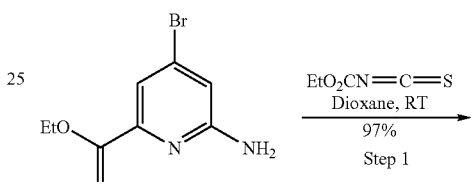

Ethyl 2-amino-4-bromopyridine-6-carboxylate (5) (1.75 g, 7.15 mmol) was dissolved in dioxane (45 mL) and the flask flushed with nitrogen. Freshly prepared ethoxycarbonyl isothiocyanate [*J. Org. Chem.*, 46, 3415-3420 (1981)] (1.04 g, 7.94 mmol) was then added dropwise and the reaction mixture stirred at room temperature for 15 h. The reaction solvent was removed under reduced pressure to give a solid which was suspended in $Et_2O$, collected by filtration and washed well with additional $Et_2O$. Further material was obtained via purification of the filtrate by chromatography on silica gel (40% EtOAc/hexanes as eluant), giving the desired compound, thiourea (6) LCMS ($APCI^+$) 376, 378.

Step 2:

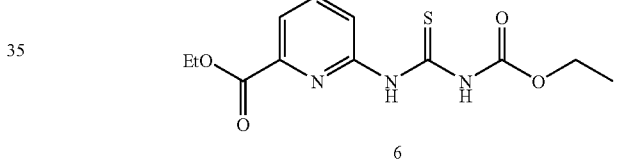

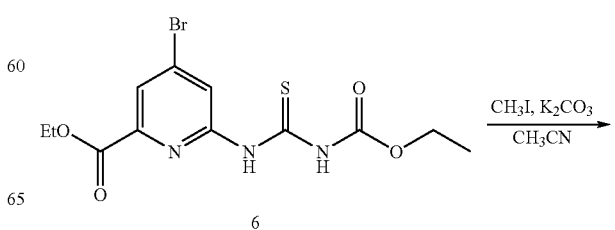

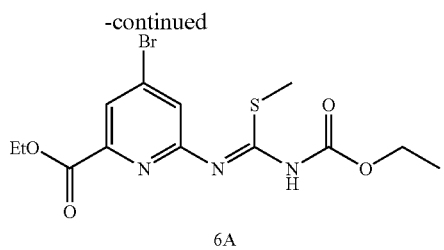

6A

Thiourea (6) (18.8 g, 50 mmol), methyl iodide (7.1 g, 50 mmol), and potassium carbonate (8.6 g, 62.5 mmol) in acetonitrile (750 mL) were heated to 40° C. After 1.5 hrs DMF (50 mL) was added with additional methyl iodide (7.1 g, 50 mmol) and the reaction was heated to 35° C. for 11 hrs. The reaction mixture was cooled to room temperature and concentrated to 20% original volume. This mixture was then partitioned between ethyl acetate/heptane (1.25 L of a 3:2 mixture) and water. The organic phase was washed with water (3×500 mL), followed by saturated sodium chloride aqueous solution (500 mL). The resultant organic phase was dried (magnesium sulfate), filtered, and concentrated to provide the desired product methylthiol (6A). MS [M+1] 390.

Step 3:

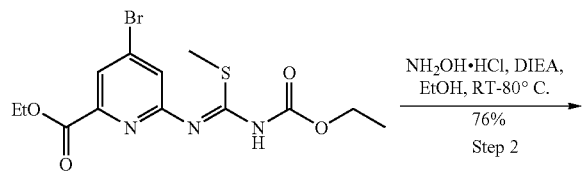

NH$_2$OH.HCl (363 mg, 5.22 mmol) and diisopropylethylamine (675 mg, 5.22 mmol) were stirred in EtOH for 10 minutes at room temperature. To this mixture was added methylthiol (6A) (1.31 g, 3.48 mmol) and the reaction stirred at room temperature for 20 minutes, followed by 80° C. for 1 h. The reaction mixture was allowed to cool, diluted with CH$_2$Cl$_2$ (150 mL), which was then washed with water (100 mL) and brine (100 mL). The organic phase was dried (Na$_2$SO$_4$) and the solvent removed under reduced pressure to give 2-amino-7-bromo-[1,2,4]triazolo[1,5-a]pyridine-5-carboxylic acid ethyl ester (7). LCMS (APCI$^+$) 285, 287.

Step 4:

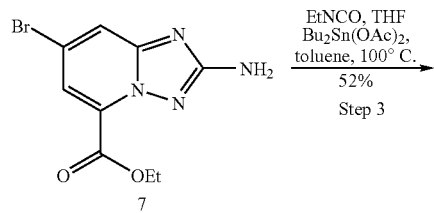

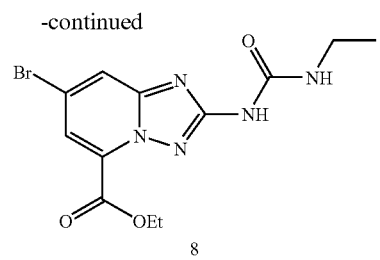

8

2-Amino-7-bromo-[1,2,4]triazolo[1,5-a]pyridine-5-carboxylic acid ethyl ester (7) (760 mg, 2.66 mmol) was dissolved in THF/toluene (1:1, 40 mL), then ethyl isocyanate (1.89 g, 26.6 mmol) and a catalytic quantity of dibutyltindiacetate (10 drops) were added to the mixture. The reaction was then heated in a sealed tube at 100° C. for 15 h. This mixture was allowed to cool, then the solvents removed under reduced pressure to afford a solid which was purified by flash chromatography on silica 2% MeOH/CH$_2$Cl$_2$ as eluant) to give 7-bromo-2-(3-ethyl-ureido)-[1,2,4]triazolo[1,5-a]pyridine-5-carboxylic acid ethyl ester (8) LCMS (APCI$^+$) 356, 358.

Step 5:

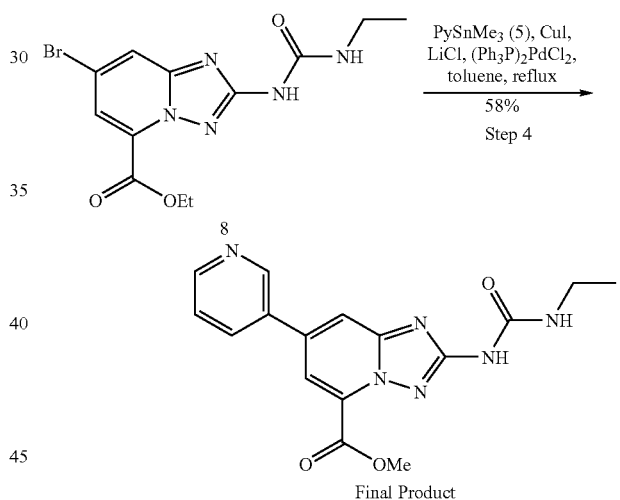

Final Product

A mixture of 7-bromo-2-(3-ethyl-ureido)-[1,2,4]triazolo[1,5-a]pyridine-5-carboxylic acid ethyl ester (8)(240 mg, 0.67 mmol), (Ph$_3$P)$_2$PdCl$_2$ (24 mg, 0.03 mmol) and CuI (13 mg, 0.07 mg) were suspended in dry toluene (5 mL). A solution of 3-pyridyltrimethylstannane [195 mg, 0.81 mmol; prepared from 3-bromopyridine according to the procedure of *J. Org. Chem.*, 64(19), 6999-7008 (1999)] in toluene (5 mL) was added, followed by LiCl (143 mg, 3.37 mmol) as a single portion. The entire mixture was heated at reflux under nitrogen for 2 h. The reaction mixture was allowed to cool, then diluted with 10% MeOH/CH$_2$Cl$_2$ (80 mL). This organic solution was washed with water (80 mL), 1 M KF solution (80 mL) and brine (80 mL). The organic layer was filtered to remove inorganic solids, dried (Na$_2$SO$_4$), and the solvent removed under reduced pressure to give a solid which was purified by chromatography on silica (2% MeOH/CH$_2$Cl$_2$ as eluant). Transesterification from the ethyl to the methyl ester occurred during workup and chromatography. 2-(3-Ethyl-ureido)-7-pyridin-3-yl-[1,2,4]triazolo[1,5-a]pyridine-5-carboxylic acid methyl ester was isolated; mp. 211-213° C. LCMS (APCI+) 341. HRMS (FAB+) calcd $C_{16}H_{17}N_6O_3$ (MH+) 341.1362, found 341.1358.

Example 7

2-(3-Ethyl-ureido)-7-pyridin-3-yl-[1,2,4]triazolo[1,5-a]pyridine-5-carboxylic acid methylamide 2-(3-Ethyl-ureido)-7-pyridin-3-yl-[1,2,4]triazolo[1,5-a]pyridine-5-carboxylic acid methyl ester, prepared as in Example 6, (46 mg, 0.14 mmol) was suspended/dissolved in 33% methylamine in EtOH (15 mL), then stirred overnight at room temperature. After this time the reaction mixture was concentrated to a volume of ca 5 mL, then diluted with $Et_2O$ (5 mL). The resulting precipitate was isolated by filtration and washed well with $Et_2O$ to give the final product mp. >300° C. LCMS (APCI+) 340.

Example 8

2-(3-Ethyl-ureido)-7-pyridin-3-yl-[1,2,4]triazolo[1,5-a]pyridine-5-carboxylic acid ethylamide Step 1:

Ethylamine (0.300 mL, 70% solution in water) and 7-bromo-2-(3-ethyl-ureido)-[1,2,4]triazolo[1,5-a]pyridine-5-carboxylic acid ethyl ester, prepared as in Example 6 (0.251 g, 0.705 mmol), was suspended in ethanol (3.00 mL) and shaken. After 20 hours the reaction was filtered and the filtrate washed with cold ethanol to afford 7-bromo-2-(3-ethyl-ureido)-[1,2,4]triazolo[1,5-a]pyridine-5-carboxylic acid ethylamide MS (APCI+): m/z 356.0 (M+H).

Step 2:

7-Bromo-2-(3-ethyl-ureido)-[1,2,4]triazolo[1,5-a]pyridine-5-carboxylic acid ethylamide (0.160 g, 0.450 mmol), pyridine-3-boronic acid (0.0910 g, 0.742 mmol), sodium carbonate (0.215 g, 2.03 mmol), and bis(diphenylphosphino)ferrocene palladium (II) chloride (0.005 g) were suspended in a solution of ethylene glycol dimethyl ether/water/ethanol (7:3:2, 6.00 mL) and subjected to microwave at 80° C. for 30 minutes. The reaction mixture was acidified with acetic acid and purified by column chromatography (gradient 0-5% methanol/dichloromethane) to afford the desired product 2-(3-ethyl-ureido)-7-pyridin-3-yl-[1,2,4]triazolo[1,5-a]pyridine-5-carboxylic acid ethylamide MS (APCI+): m/z 354.3 (M+H).

Example 9

2-(3-Ethyl-ureido)-7-pyridin-3-yl-[1,2,4]triazolo[1,5-a]pyridine-5-carboxylic acid propylamide Utilizing the procedure of Example 8, but substituting propylamine in step 1, 2-(3-ethyl-ureido)-7-pyridin-3-yl-[1,2,4]triazolo[1,5-a]pyridine-5-carboxylic acid propylamide was produced. MS (APCI+): m/z 368.1 (M+H).

Example 10

2-(3-Ethyl-ureido)-7-pyridin-3-yl-[1,2,4]triazolo[1,5-a]pyridine-5-carboxylic acid cyclopropylmethyl-amide Utilizing the procedure of Example 8, but substituting cyclopropylmethyl amine in step 1, 2-(3-ethyl-ureido)-7-pyridin-3-yl-[1,2,4]triazolo[1,5-a]pyridine-5-carboxylic acid cyclopropylmethyl-amide was produced. MS (APCI+): m/z 380.3 (M+H).

Example 11

2-(3-Ethyl-ureido)-7-pyridin-3-yl-[1,2,4]triazolo[1,5-a]pyridine-5-carboxylic acid benzylamide Utilizing the procedure of Example 8, but substituting benzylamine in step 1, 2-(3-ethyl-ureido)-7-pyridin-3-yl-[1,2,4]triazolo[1,5-a]pyridine-5-carboxylic acid benzylamide was produced. MS (APCI+): m/z 416.3 (M+H).

Example 12

2-(3-Ethyl-ureido)-7-pyridin-3-yl-[1,2,4]triazolo[1,5-a]pyridine-5-carboxylic acid isopropylamide Utilizing the procedure of Example 8, but substituting isopropylamine in step 1, 2-(3-ethyl-ureido)-7-pyridin-3-yl-[1,2,4]triazolo[1,5-a]pyridine-5-carboxylic acid isopropylamide was prepared. MS (APCI+): m/z 368.1 (M+H).

Example 13

2-(3-Ethyl-ureido)-7-pyridin-3-yl-[1,2,4]triazolo[1,5-a]pyridine-5-carboxylic acid cyclopropylamide Step 1:

Cyclopropylamine (0.136 g, 2.38 mmol) was suspended in tetrahydrofuran (2.00 mL) and cooled in an ice bath. This solution was charged with 2 molar trimethylaluminum in heptane (0.300 mL). After 20 minutes the solution was charged with 7-bromo-2-(3-ethyl-ureido)-[1,2,4]triazolo[1,5-a]pyridine-5-carboxylic acid ethyl ester produced as in Example 6, (0.248 g, 0.696 mmol) and shaken. After 24 hours the reaction was dissolved in dichloromethane and washed with saturated aqueous ammonium chloride. The organic layers were dried over magnesium sulfate and concentrated to afford 7-bromo-2-(3-ethyl-ureido)-[1,2,4]triazolo[1,5-a]pyridine-5-carboxylic acid cyclopropylamide MS (ACPI+): m/z 368.2 (M+H).

Step 2:

Utilizing the procedure of Example I, step 4, but substituting the product of Step 1 as the relevant reactant, 2-(3-ethyl-ureido)-7-pyridin-3-yl-[1,2,4]triazolo[1,5-a]pyridine-5-carboxylic acid cyclopropylamide was prepared. MS (APCI+): m/z 366.3 (M+H).

Example 14

2-(3-Ethyl-ureido)-7-pyridin-3-yl-[1,2,4]triazolo[1,5-a]pyridine-5-carboxylic acid diethylamide Diethylamine (0.400 mL) was suspended in tetrahydrofuran (2.00 mL) and cooled in an ice bath. This solution was charged with trimethylaluminum (0.500 mL of a 2 M solution in heptane). After 20 minutes the reaction was charged with the 2-(3-ethyl-ureido)-7-pyridin-3-yl-[1,2,4]triazolo[1,5-a]pyridine-5-carboxylic acid ethyl ester, prepared as in Example 16, Step 1, (0.255 g, 0.720 mmol) and shaken. After 18 hours the reaction was diluted with 1 volume of ethyl acetate and treated with an equal amount saturated aqueous sodium/potassium tartrate. After 6 hours the organic layer was isolated, dried over magnesium sulfate and concentrated to afford the desired product 2-(3-ethyl-ureido)-7-pyridin-3-yl-[1,2,4]triazolo[1,5-a]pyridine-5-carboxylic acid diethylamide, MS (APCI+): m/z 382.1 (M+H).

Example 15

1-Ethyl-3-[5-(pyrrolidine-1-carbonyl)-7-pyrrolidin-1-yl-[1,2,4]triazolo[1,5-a]pyridin-2-yl]-urea To a suspension of 7-bromo-2-(3-ethyl-ureido)-[1,2,4]triazolo[1,5-a]pyridine-5-carboxylic acid ethyl ester prepared as in Example 16, Step 1 (0.080 g, 0.22 mmol) in dimethylsulfoxide (1 mL) was added pyrrolidine (0.2 mL). The reaction was stirred at 23° C. for 30 minutes, then 80° C. for 3 days. The reaction was then diluted with 2 volumes of water, acidified with 1N aqueous hydrogen chloride, then neutralized with saturated aqueous sodium bicarbonate and extracted with ethyl acetate (3×20 mL). The combined organic extracts were dried over sodium sulfate and evaporated in vacuo to give a colorless oily solid that was purified by silica gel chromatography (gradient elution: 0-20% isopropanol/dichloromethane) to give 1-ethyl-3-[5-(pyrrolidine-1-carbonyl)-7-pyrrolidin-1-yl-[1,2,4]triazolo[1,5-a]pyridin-2-yl]-urea MS (APCI)=372.2 [M+H]

Example 16

2-(3-Ethyl-ureido)-7-pyridin-3-yl-[1,2,4]triazolo[1,5-a]pyridine-5-carboxylic acid amide

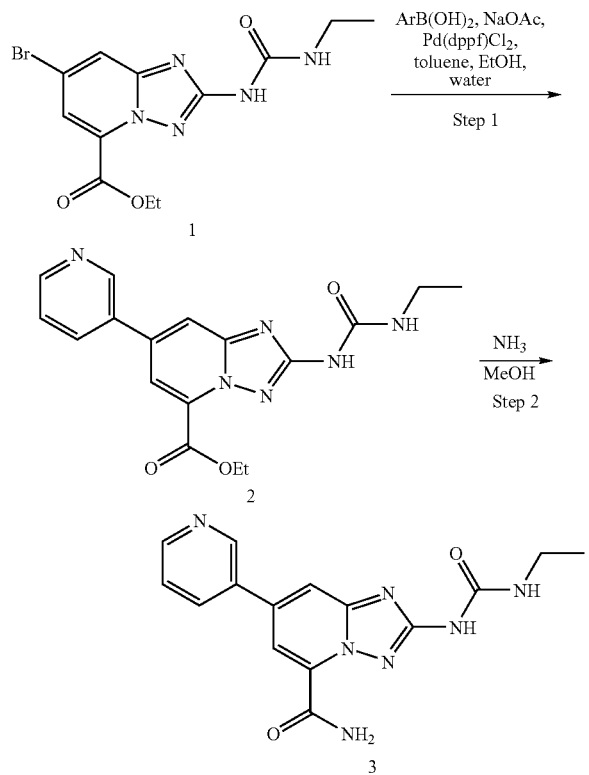

Step 1:
Bromide (I) prepared as in Example 6, Step 4, (2.70 g, 7.58 mmol) and NaOAc (3.11 g, 37.9 mmol) were suspended in toluene (120 mL) to which was added a suspension of pyridine-3-boronic acid (1.40 g, 11.4 mmol) in EtOH (30 mL). Water (30 mL) and Pd(dppf)Cl$_2$ (336 mg, 0.38 mmol) were added and the mixture heated at reflux temperature for 2 h under nitrogen. The mixture was allowed to cool and all solvent then removed under reduced pressure. The residue was taken up in CH$_2$Cl$_2$/EtOH, inorganic salts were removed by filtration, and the filtrate was evaporated onto silica gel for purification. Purification by silica gel column chromatography (gradient: 2-5% EtOH/CH$_2$Cl$_2$ as eluant) provided ester (2) 2-(3-ethyl-ureido)-7-pyridin-3-yl-[1,2,4]triazolo[1,5-a]pyridine-5-carboxylic acid ethyl ester as a solid. mp. 242-245° C. Anal. calcd for C$_{17}$H$_{18}$N$_6$O$_3$: C, 57.6; H, 5.1; N, 23.7. Found: C, 57.4; H, 5.1; N, 23.5.

Step 2:
Ester (2) was suspended in a solution of 2 M NH$_3$ in MeOH (50 mL) and stirred at room temperature for 18 h. The solvent was removed under reduced pressure, then diluted with Et$_2$O. The resulting precipitate was collected by filtration yielding amide (3), 2-(3-ethyl-ureido)-7-pyridin-3-yl-[1,2,4]triazolo[1,5-a]pyridine-5-carboxylic acid amide. LCMS (APCI$^+$) 326. Anal. calcd for C$_{15}$H$_{15}$N$_7$O$_2$: C, 55.4; H, 4.7; N, 30.1. Found: C, 55.5; H, 4.7; N, 30.0.

Example 17

1-Ethyl-3-[5-(5-methyl-2H-[1,2,4]triazol-3-yl)-7-pyridin-3-yl-[1,2,4]triazolo[1,5-a]pyridin-2-yl]-urea 2-(3-Ethyl-ureido)-7-pyridin-3-yl-[1,2,4]triazolo[1,5-a]pyridine-5-carboxylic acid amide, which may be prepared as in Example 16, (200 mg, 0.62 mmol) was suspended in DMA (8 mL) and preheated to 90° C. Dimethylacetamide-dimethylacetal (0.45 mL, 3.07 mmol) was added and the solution was heated at 90° C. for 30 minutes. The reaction was allowed to cool, diluted with water (100 mL), then extracted with CH$_2$Cl$_2$ (3×50 mL). The combined CH$_2$Cl$_2$ fractions were washed with water (3×50 mL), brine (50 mL), and dried (Na$_2$SO$_4$). The mixture was filtered under reduced pressure. The resultant oil was dissolved in AcOH and hydrazine hydrate (0.1 mL, 1.85 mmol) was added. The mixture was heated at 90° C. for 2 h. All solvent was then removed under high vacuum and the resulting slurry suspended in sat. NaHCO$_3$ solution (50 mL). Crude 1-ethyl-3-[5-(5-methyl-2H-[1,2,4]triazol-3-yl)-7-pyridin-3-yl-[1,2,4]triazolo[1,5-a]pyridin-2-yl]-urea triazole) was isolated by filtration and dried. Purification by silica gel chromatography (0.5% c.NH$_3$ in 10% MeOH/CH$_2$Cl$_2$ as eluant) gave the desired product. HRMS (FAB$^+$) calcd C$_{17}$H$_{17}$N$_9$O (MH$^+$) 364.1634, found 364.1632.

Example 18

1-Ethyl-3-[5-(3-methyl-[1,2,4]oxadiazol-5-yl)-7-pyridin-3-yl-[1,2,4]triazolo[1,5-a]pyridin-2-yl]-urea 2-(3-Ethyl-ureido)-7-pyridin-3-yl-[1,2,4]triazolo[1,5-a]pyridine-5-carboxylic acid amide, which may be prepared as in Example 16, (200 mg, 0.62 mmol) was suspended in DMA (8 mL) and preheated to 90° C. Dimethylacetamide-dimethylacetal (0.45 mL, 3.07 mmol) was added and the solution was heated at 90° C. for 30 minutes. The reaction was allowed to cool, diluted with water (100 mL), then extracted with CH$_2$Cl$_2$ (3×50 mL). The combined CH$_2$Cl$_2$ fractions were washed with water (3×50 mL), brine (50 mL), and dried (Na$_2$SO$_4$). The mixture was filtered under reduced pressure. The resultant oil was dissolved in a mixture of dioxane and acetic acid (3 mL of a 1:1 mixture). Hydroxylamine hydrochloride (64 mg, 0.92 mmol) and 2 M NaOH solution (0.46 mL, 0.92 mmol) were added and the mixture was stirred at 90° C. for 2 h. The reaction mixture was allowed to cool, concentrated under reduced pressure and diluted with water (50 mL) to afford a precipitate. The precipitate was collected by filtration, then purified by chromatography on silica gel (5% MeOH/CH$_2$Cl$_2$ as eluant) to give the desired product, 1-ethyl-3-[5-(3-methyl-[1,2,4]oxadiazol-5-yl)-7-pyridin-3-yl-[1,2,4]triazolo[1,5-a]pyridin-2-yl]-urea (27) as a solid mp. 298-301° C.

Example 19

N-Ethyl-2-{[(ethylamino)carbonyl]amino}-7-pyrimidin-5-yl[1,2,4]triazolo[1,5-a]pyridine-5-carboxamide Step 1:
A mixture of 7-bromo-2-(3-ethyl-ureido)-[1,2,4]triazolo[1,5-a]pyridine-5-carboxylic acid ethyl ester (0.548 g, 1.54 mmol/prepared as in Example 6, Step 4) sodium acetate (0.63 g, 7.68 mmol), dppf (86 mg, 0.155 mmol), pyrimidine-5-boronic acid (0.289 g, 2.33 mmol) in toluene (30 mL)/water (6 mL)/ethanol (6 mL) was purged with nitrogen. PdCl$_2$(PhCN)$_2$ (60 mg, 0.156 mmol) was added and the mixture was purged with nitrogen then refluxed for 0.5 h. The reaction mixture was cooled and the resulting crystalline product was filtered and washed with water. The product was dissolved in hot methanol, filtered through celite and cooled to give 2-(3-ethyl-ureido)-7-pyrimidin-5-yl-[1,2,4]triazolo[1,5-a]pyridine-5-carboxylic acid ethyl ester as a solid. ACPI-MS Found: [M+H]+=356.

Step 2:
A slurry of the product of Step 1 (0.268 g, 0.754 mmol) in dimethylacetamide (10 mL) was treated with ethylamine (2 mL, 30.6 mmol) then heated to 60° C. in a sealed tube for 16 h. The precipitate was filtered, washed with dimethylacetamide and then water, to give title compound as a solid; m.p. 317-321° C. ACPI-MS Found: [M+H]+=355.

Example 20

7-[2-(Dimethylamino)pyrimidin-5-yl]-N-ethyl-2-{[(ethylamino)carbonyl]amino}[1,2,4]triazolo[1,5-a]pyridine-5-carboxamide Using the generalized procedure of Example 19, but substituting 2-(dimethylamino)-5-pyrimidinylboronic acid for pyrimidine-5-boronic acid in Step 1, the title compound was obtained as a solid; m.p. 328-334° C. ACPI-MS Found: [M+H]+=398.

Example 21

7-(3,5-Dimethylisoxazol-4-yl)-N-ethyl-2-{[(ethylamino)carbonyl]amino}[1,2,4]triazolo[1,5-a]pyridine-5-carboxamide Using the generalized procedure of 19, but substituting 3,5-dimethyl-4-isoxazolylboronic acid for pyrimidine-5-boronic acid in Step 1, the title compound was obtained. Recrystallisation of the crude product from methanol gave the title compound as a solid; m.p. 238-241° C. ACPI-MS Found: [M+H]+=372.

Example 22

N-Ethyl-N'-[5-(1,3-oxazol-5-yl)-7-pyridin-3-yl[1,2,4]triazolo[1,5-a]pyridin-2-yl]urea Step 1:
2-(3-Ethyl-ureido)-7-pyridin-3-yl-[1,2,4]triazolo[1,5-a]pyridine-5-carboxylic acid ethyl ester, produced as in Example 16, Step 2, (250 mg, 0.71 mmol) was dissolved/suspended in absolute EtOH (50 mL). A solution of NaBH4 (134 mg, 3.53 mmol) in EtOH (5 mL) was then added dropwise, and the mixture stirred at room temperature for 1.5 h. The reaction mixture was diluted with water (100 mL), then extracted with EtOAc (4×80 mL). The combined EtOAc fractions were washed with brine (100 mL), dried (Na$_2$SO$_4$), and the solvent removed under reduced pressure to afford a crude solid which was purified by filtration through a plug of silica gel (5% MeOH/CH$_2$Cl$_2$ as eluant). 1-Ethyl-3-(5-hydroxymethyl-7-pyridin-3-yl-[1,2,4]triazolo[1,5-a]pyridin-2-yl)-urea was isolated as a solid. LCMS (APCI+) 313.

Step 2:
The product of Step 1 (154 mg, 0.50 mmol) was dissolved in THF (50 mL), to which was added MnO$_2$ (250 mg). This mixture was heated at reflux for 18 h., at which point two further portions (50 mg each) were added over the next 8 hours. Finally, the mixture was heated at reflux for 18 h., allowed to cool, then the MnO$_2$ removed by filtration over celite which was washed with THF and MeOH/CH$_2$Cl$_2$. The solvent was removed under reduced pressure to afford 1-ethyl-3-(5-formyl-7-pyridin-3-yl-[1,2,4]triazolo[1,5-a]pyridin-2-yl)-urea as a crude solid. LCMS (APCI+) 311.

Step 3:
A mixture of the product of Step 2 (40 mg, 0.13 mmol), tosylmethyl isocyanide (28 mg, 0.14 mmol) and K$_2$CO$_3$ (36 mg, 0.26 mmol) were stirred at room temperature in MeOH (5 mL) for a few minutes, then heated at reflux for 0.5 h. All solvent was then removed under reduced pressure, the residue taken up into MeOH/CH$_2$Cl$_2$, and dried onto silica. Purification was carried out by filtration through a plug of silica gel (5% MeOH/CH$_2$Cl$_2$ as eluant) to give the title compound as a solid. LCMS (APCI+) 350.

Example 23

N-Ethyl-N'-[5-(5-methyl-1,3,4-oxadiazol-2-yl)-7-pyridin-3-yl[1,2,4]triazolo[1,5-a]pyridin-2-yl]urea Step 1:
A slurry of 2-(3-ethyl-ureido)-7-pyridin-3-yl-[1,2,4]triazolo[1,5-a]pyridine-5-carboxylic acid ethyl ester which may be produced as in Example 16, (1.45 g, 4.09 mmol) in ethanol (60 mL) and hydrazine hydrate (4 mL) was refluxed for 4 h. The mixture was cooled and the product was filtered, washed with water and dried to give 1-ethyl-3-(5-hydrazinocarbonyl-7-pyridin-3-yl-[1,2,4]triazolo[1,5-a]pyridin-2-yl)-urea as a solid. ACPI-MS Found: [M+H]+=341.

Step 2:
Acetic anhydride (0.95 mL, 10 mmol), triethylamine (1.2 mL, 8.6 mmol) and the product of Step 1 (0.996 g, 2.93 mmol) in dioxane (100 mL) was refluxed for 6 h. The solution was cooled and the product was filtered, washed with water and then dried to give 1-[5-(N'-acetyl-hydrazinocarbonyl)-7-pyridin-3-yl-[1,2,4]triazolo[1,5-a]pyridin-2-yl]-3-ethyl-urea as a solid ACPI-MS Found: [M+H]+=383.

Step 3:

A mixture of the product of Step 2 (0.419 g, 1.10 mmol) in polyphosphoric acid (10 mL) was heated to 120° C. for 2 h. The viscous mixture was poured onto ice and made basic with saturated aqueous sodium bicarbonate, then extracted with dichloromethane (4×250 mL). Removal of the solvent in vacuo gave a solid which was triturated with methanol then filtered to give 5-(5-methyl-[1,3,4]oxadiazol-2-yl)-7-pyridin-3-yl-[1,2,4]triazolo[1,5-a]pyridin-2-ylamine (0.185 g, 58%) as a solid. ACPI-MS Found: [M+H]+=294.

Step 4:

A suspension of the product of Step 3 in toluene (20 mL) containing dibutyltin diacetate (0.1 mL) and ethyl isocyanate (0.2 mL) was heated to 110° C. for 48 h. The suspension was cooled and the precipitate was filtered and washed with toluene to give the tile compound as a solid; m.p. 318-321°. ACPI-MS Found: [M+H]+=365.

Example 24

N-Ethyl-N'-{5-[(E)-(hydroxyimino)methyl]-7-pyridin-3-yl[1,2,4]triazolo[1,5-a]pyridin-2-yl}urea 1-Ethyl-3-(5-formyl-7-pyridin-3-yl-[1,2,4]triazolo[1,5-a]pyridin-2-yl)-urea, which may be produced as in Example 22, Step 2, was suspended in MeOH (40 mL) and treated with pyridine (319 mg, 4.03 mmol) followed by hydroxylamine hydrochloride (280 mg, 4.03 mmol). This mixture was stirred at room temperature for 2 h. The reaction solvent was removed under reduced pressure and the resulting residue suspended in water, collected by filtration and dried to give the desired product as a solid. LCMS (APCI+) 326.

Example 25

N-Ethyl-N'-[5-(1-hydroxyethyl)-7-pyridin-3-yl[1,2,4]triazolo[1,5-a]pyridin-2-yl]urea 1-Ethyl-3-(5-formyl-7-pyridin-3-yl-[1,2,4]triazolo[1,5-a]pyridin-2-yl)-urea which may be produced as in Example 22, Step 2, (186 mg, 0.60 mmol) was dissolved in dry THF (100 mL) and cooled to −30° C. under nitrogen. Methylmagnesium bromide (1.00 mL of a 3.0M solution in diethyl ether, 3.00 mmol) was added dropwise and the resulting yellow-orange mixture stirred at −30° C. for 1 h., then room temperature overnight. Saturated NH$_4$Cl (100 mL) was added and the resulting aqueous solution extracted with EtOAc (3×100 mL). The combined organic fractions were dried (Na$_2$SO$_4$), evaporated onto silica gel, and filtered through a plug of silica (gradient: 5-10% MeOH/CH$_2$Cl$_2$ as eluant) to provide title compound as a solid. LCMS (APCI+) 327.

Example 26

N-(5-Acetyl-7-pyridin-3-yl[1,2,4]triazolo[1,5-a]pyridin-2-yl)-N'-ethylurea

N-Ethyl-N'-[5-(1-hydroxyethyl)-7-pyridin-3-yl[1,2,4]triazolo[1,5-a]pyridin-2-yl]urea, which may be produced as in Example 25, was dissolved in a mixture of DMSO (10 mL) and triethylamine (850 mg, 8.42 mmol). A solution of sulphur trioxide-pyridine complex (574 mg, 3.61 mmol) in DMSO (2.5 mL) was added dropwise over 10 minutes, then the mixture stirred at room temperature overnight. The solution was diluted with water, the pH adjusted to 4-4.5 with 1 M HCl, and the resulting solid isolated by filtration. The solid was then purified by column chromatography on silica gel (5% MeOH/CH$_2$Cl$_2$ as eluant) to afford the desired compound as a solid. LCMS (APCI+) 325.

Example 27

N-(5-Cyano-7-pyridin-3-yl[1,2,4]triazolo[1,5-a]pyridin-2-yl)-N'-ethylurea

N-Ethyl-N'-{5-[(E)-(hydroxyimino)methyl]-7-pyridin-3-yl[1,2,4]triazolo[1,5-a]pyridin-2-yl}urea, which may be produced by the method of Example 24, (308 mg, 0.95 mmol) and sodium acetate (20 mg, catalytic) were suspended in acetic anhydride (30 mL) then heated at 100° C. for 1 h. The acetic anhydride was then removed under reduced pressure and the resulting residue taken up into a mixture of CH$_2$Cl$_2$/MeOH and evaporated onto silica gel. Purification was carried out by chromatography on silica (gradient elution: 0-5% CH$_2$Cl$_2$/MeOH) to give the nitrile as a solid. LCMS (APCI+) 308.

Example 28

1-Ethyl-3-{5-[5-(2-oxo-propyl)-[1,3,4]oxadiazol-2-yl]-7-pyridin-3-yl-[1,2,4]triazolo[1,5-a]pyridin-2-yl}-urea Step 1:

2-Amino-7-bromo-[1,2,4]triazolo[1,5-a]pyridine-5-carboxylic acid methyl ester (5.0 g, 18 mmol), produced by the general method of Example 6, Step 2, was suspended in 100 mL of MeOH and hydrazine (0.66 mL, 21 mmol) was added. The mixture was heated to reflux and stirred overnight. The mixture was allowed to cool and the resulting solid was collected by filtration and dried under vacuum to give 2-amino-7-bromo-[1,2,4]triazolo[1,5-a]pyridine-5-carboxylic acid hydrazide. MS (APCI+): m/z 270.9, 272.9.

Step 2:

The product of Step 1, 2-amino-7-bromo-[1,2,4]triazolo[1,5-a]pyridine-5-carboxylic acid hydrazide (1.0 g, 3.7 mmol), diketene (0.28 mL, 3.7 mmol) and THF (~25 mL) were placed in a flask. The mixture was stirred at room temperature for 48 hours. The solvent was removed under reduced pressure and the residue was partitioned between water and a solution of 9:1 CH$_2$Cl$_2$/MeOH. The organics were dried with MgSO4 and concentrated to give an oily yellow solid. The solid was dissolved in a small amount of CH$_2$Cl$_2$ and filtered through a plug of silica, eluting with CH$_2$Cl$_2$. The filtrate was concentrated to give 1-[5-(2-amino-7-bromo-[1,2,4]triazolo[1,5-a]pyridine-5-yl)-[1,3,4]oxadiazol-2-yl]-propan-2-one, which was used without further purification, in Step 3. MS (APCI+): m/z 337.0, 339.0.

Step 3:

1-[5-(2-Amino-7-bromo-[1,2,4]triazolo[1,5-a]pyridine-5-yl)-[1,3,4]oxadiazol-2-yl]-propan-2-one (product of Step 2), (0.37 g, 1.1 mmol), 3-pyridyl boronic acid (0.2 g, 1.65 mmol) and NaOAc, (0.5 g, 5 mmol) were placed in a flask with 100 mL of 8:1:1 toluene/EtOH/water and placed under a N$_2$ atmosphere. PdCl$_2$(dppf), (0.09 g, 0.11 mmol) was added and the mixture was heated to 105° C. for two hours. The mixture was concentrated to dryness under reduced pressure and the residue taken up in 100 mL of 9:1 CH$_2$Cl$_2$/methanol. The mixture was filtered through celite and insoluble residue discarded. The filtrate was extracted with 1 N HCl (3×25 mL), and any residue in the aqueous removed by filtration. The aqueous filtrate was adjusted to pH 8 with K$_2$CO$_3$, resulting in a precipitate that was dried under vacuum to give 1-[5-(2-Amino-7-pyridin-3-yl-[1,2,4]triazolo[1,5-a]pyridine-5-yl)-[1,3,4]oxadiazol-2-yl]-propan-2-one. MS (APCI+): m/z 336.1.

Step 4:

The product of Step 3, 1-[5-(2-Amino-7-pyridin-3-yl-[1,2,4]triazolo[1,5-a]pyridine-5-yl)-[1,3,4]oxadiazol-2-yl]-propan-2-one, (0.1 g, 0.3 mmol) ethyl isocyanate (0.02 g, 0.3 mmol) three drops of dibutyltin diacetate, and 15 mL of THF were added to a screw-cap vial and heated to 100° C. for 48 hours. After cooling, the resulting solid was collected by filtration, washed sparingly with water, and dried under vacuum to give the title compound 1-ethyl-3-{5-[5-(2-oxo-propyl)-[1,3,4]oxadiazol-2-yl]-7-pyridin-3-yl-[1,2,4]triazolo[1,5-a]pyridin-2-yl}-urea. MS (APCI+): m/z 407.1.

Example 29

1-Ethyl-3-[5-[5-isopropyl)-[1,3,4]oxadiazol-2-yl]-7-pyridin-3-yl-[1,2,4]triazolo[1,5-a]pyridin-2-yl}-urea Step 1:

2-Amino-7-bromo-[1,2,4]triazolo[1,5-a]pyridine-5-carboxylic acid hydrazide (1.0 g, 3.7 mmol, produced as in Example 29, Step 1) was added to neat isobutyric anhydride (~20 mL) and stirred overnight. The resulting solid was collected by filtration and washed with EtOAc and ether, then dried under vacuum to give 2-amino-7-bromo-[1,2,4]triazolo[1,5-a]pyridine-5-carboxylic acid N'-isobutyryl-hydrazide, which was used without further purification. MS (APCI+): m/z 341.0, 343.0.

Step 2:

The product of Step 1, 2-amino-7-bromo-[1,2,4]triazolo[1,5-a]pyridine-5-carboxylic acid N'-isobutyryl-hydrazide (1.0 g, 2.9 mmol) was suspended in neat POCl3 (~10 mL) and heated to 100° C. for one hour. The mixture was concentrated under reduced pressure and the residue was diluted with water. The pH of the aqueous mixture was made slightly basic by the addition of K$_2$CO$_3$, then extracted with a solution of 9:1 CH$_2$Cl$_2$/MeOH (50 mL). The organics were dried with MgSO4 and concentrated under reduced pressure to give a solid, which was triturated with ether and collected by filtration and dried under vacuum to give 7-bromo-5-(5-isopropyl-[1,3,4]oxadiazol-2-yl)-[1,2,4]triazolo[1,5-a]pyridine-2-ylamine, that was used without further purification in Step 3. MS (APCI+): m/z 325.0.

Step 3: 5-(5-Isopropyl-[1,3,4]oxadiazol-2-yl)-7-pyridin-3-yl[1,2,4]triazolo[1,5-a]pyridine-2-ylamine was prepared analogously to Example 29, Step 3, except 7-bromo-5-(5-isopropyl-[1,3,4]oxadiazol-2-yl)-[1,2,4]triazolo[1,5-a]pyridine-2-ylamine was used as the starting material. MS (APCI+): m/z 322.1.

Step 4:

1-Ethyl-3-[5-[5-isopropyl)-[1,3,4]oxadiazol-2-yl]-7-pyridin-3-yl-[1,2,4]triazolo[1,5-a]pyridin-2-yl]-urea was prepared by the general method of Example 29, Step 4, except 5-(5-isopropyl-[1,3,4]oxadiazol-2-yl)-7-pyridin-3-yl[1,2,4]triazolo[1,5-a]pyridine-2-ylamine (0.25 g, 0.8 mmol) was used as the starting material to give the desired product, 1-ethyl-3-[5-[5-isopropyl)-[1,3,4]oxadiazol-2-yl]-7-pyridin-3-yl-[1,2,4]triazolo[1,5-a]pyridin-2-yl}-urea. MS (APCI+): m/z 393.1.

Example 30

1-[7-(2-Dimethylamino-pyrimidin-5-yl)-5-(5-isobutyl-[[1,3,4]thiadiazol-2-yl)-[1,2,4]triazolo[1,5-a]pyridine-2-yl]-3-ethylurea

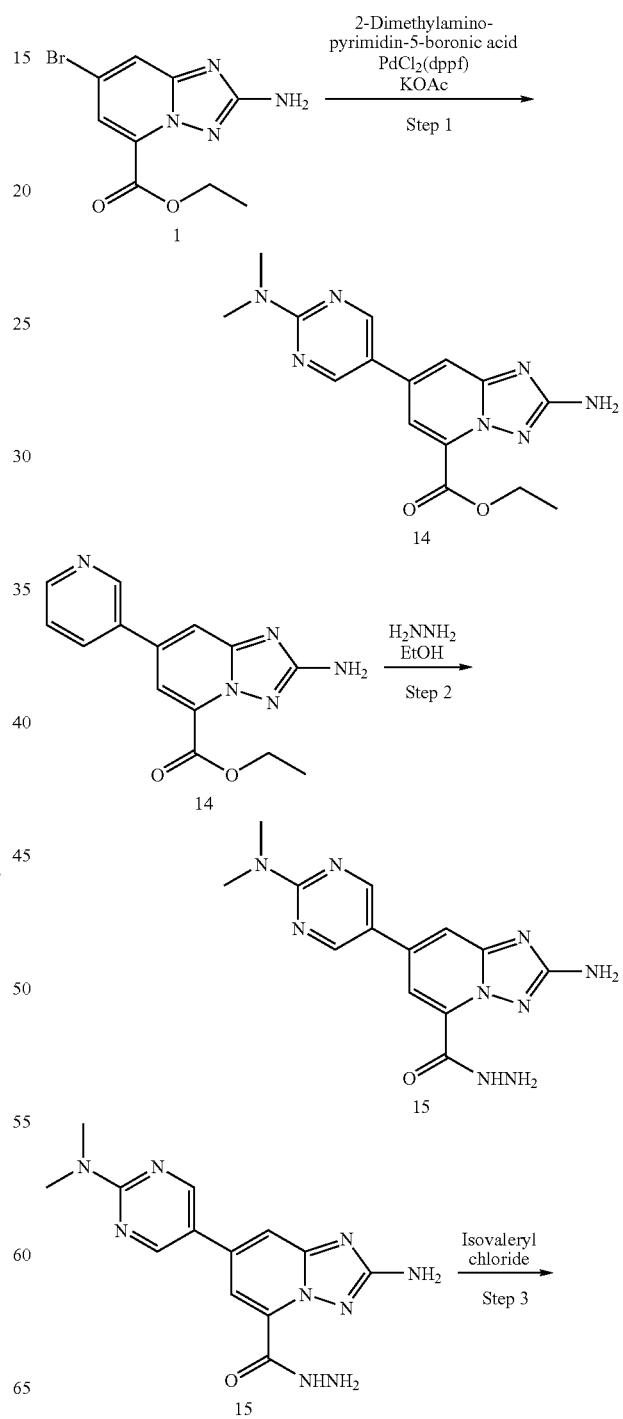

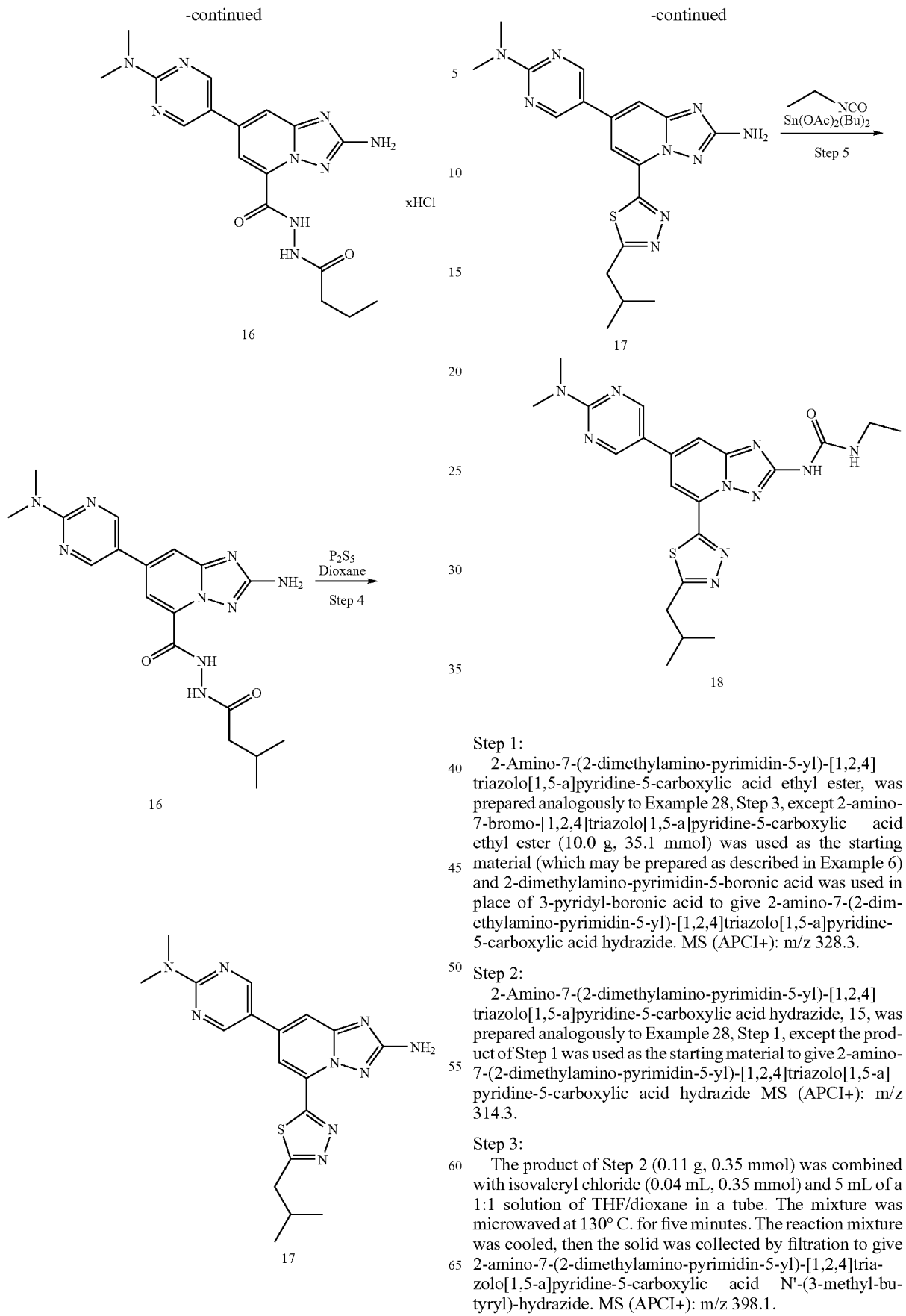

Step 1:

2-Amino-7-(2-dimethylamino-pyrimidin-5-yl)-[1,2,4]triazolo[1,5-a]pyridine-5-carboxylic acid ethyl ester, was prepared analogously to Example 28, Step 3, except 2-amino-7-bromo-[1,2,4]triazolo[1,5-a]pyridine-5-carboxylic acid ethyl ester (10.0 g, 35.1 mmol) was used as the starting material (which may be prepared as described in Example 6) and 2-dimethylamino-pyrimidin-5-boronic acid was used in place of 3-pyridyl-boronic acid to give 2-amino-7-(2-dimethylamino-pyrimidin-5-yl)-[1,2,4]triazolo[1,5-a]pyridine-5-carboxylic acid hydrazide. MS (APCI+): m/z 328.3.

Step 2:

2-Amino-7-(2-dimethylamino-pyrimidin-5-yl)-[1,2,4]triazolo[1,5-a]pyridine-5-carboxylic acid hydrazide, 15, was prepared analogously to Example 28, Step 1, except the product of Step 1 was used as the starting material to give 2-amino-7-(2-dimethylamino-pyrimidin-5-yl)-[1,2,4]triazolo[1,5-a]pyridine-5-carboxylic acid hydrazide MS (APCI+): m/z 314.3.

Step 3:

The product of Step 2 (0.11 g, 0.35 mmol) was combined with isovaleryl chloride (0.04 mL, 0.35 mmol) and 5 mL of a 1:1 solution of THF/dioxane in a tube. The mixture was microwaved at 130° C. for five minutes. The reaction mixture was cooled, then the solid was collected by filtration to give 2-amino-7-(2-dimethylamino-pyrimidin-5-yl)-[1,2,4]triazolo[1,5-a]pyridine-5-carboxylic acid N'-(3-methyl-butyryl)-hydrazide. MS (APCI+): m/z 398.1.

Step 4:

The product of Step 3 (0.065 g, 0.16 mmol) in dioxane (5 mL) was placed in a tube with phosphorus pentasulfide (0.15 g, 0.33 mmol) and heated in a microwave at 100° C. for five minutes. The supernatant was decanted and concentrated to give a solid that was used immediately without further purification.

Step 5:

The solid from step 4 (0.045 g), ethyl isocyanate (0.02 g, 0.3 mmol), three drops of dibutyltin diacetate, and 5 mL of dioxane were added to a tube and heated in a microwave at 100° C. for 20 minutes. The mixture was allowed to stand overnight. The resulting solid was collected by filtration and dried under vacuum to give 1-[7-(2-dimethylamino-pyrimidin-5-yl)-5-(5-isobutyl-[[1,3,4]thiadiazol-2-yl]-[1,2,4]triazolo[1,5-a]pyridine-2-yl]-3-ethylurea. MS (APCI+): m/z 467.1.

Example 31

2-(3-Ethyl-ureido)-7-(2-methoxy-pyridi-3-yl)-[1,2,4]triazolo[1,5-a]pyridine-5-carboxylic acid ethyl amide Step 1:

Ethyl amine (Aldrich 70% aqueous) was added to a suspension of 7-bromo-2-(3-ethyl-ureido)-[1,2,4]triazolo[1,5-a]pyridine-5-carboxylic acid ester, which may be prepared as described in Example 6, (2.03 g, 5.7 mmol) in 40 ml of ethanol and warmed to 35° C. Suspension stirred overnight under nitrogen then cooled to 0° C. and filtered. The collected solids were rinsed with ethanol, then dried in vacuo at 45° C. to yield 7-bromo-2-(3-ethyl-ureido)-[1,2,4]triazolo[1,5-a]pyridine-5-carboxylic acid ethyl amide MS (APCI10V+) 355, 357

Step 2:

7-Bromo-2-(3-ethyl-ureido)-[1,2,4]triazolo[1,5-a]pyridine-5-carboxylic acid ethyl amide (product of Step 1) (0.150 g, 0.42 mmol) and sodium acetate (0.156 g, 1.90 mmol) were suspended in toluene (7.5 ml). 2-Methoxy-3-pyridineboronic acid (0.097 g, 0.634 mmol) suspended in ethanol (1.5 mL) followed by [1,1'-Bis(diphenylphosphino)-ferrocene) dichloropalladium (II) complex with dichloromethane (0.017 g, 0.021 mmol) suspended in water (1.1 mL) were added to the toluene suspension which was then degassed (3x's) using $N^2$ and vacuum before warming to reflux. Reaction mixture was cooled to room temperature and concentrated in vacuo. The solid residue was purified by silica gel chromatography (gradient: 0-5% methanol/dichloromethane) to give 2-(3-ethyl-ureido)-7-(2-methoxy-pyridi-3-yl)-[1,2,4]triazolo[1,5-a]pyridine-5-carboxylic acid ethyl amide as a solid. MS (APCI10V+) 384)

Example 32

2-(3-Ethyl-ureido)-7-(4-methoxy-pyridin-3-yl)-[1,2,4]triazolo[1,5-a]pyridine-5-carboxylic acid ethyl amide Using the general procedure of Example 31, Step 2, but substituting 4-methoxy-3-pyridineboronic acid (0.097 g, 0.634 mmol) for 2-methoxy-3-pyridineboronic acid, the title compound was obtained. Solid residue was purified by silica gel chromatography (gradient: 0-5% methanol/dichloromethane) to give 2-(3-ethyl-ureido)-7-(4-methoxy-pyridi-3-yl)-[1,2,4]triazolo[1,5-a]pyridine-5-carboxylic acid ethyl amide (5) as a solid. MS (APCI10V+) 384).

Example 33

7-(3,6-Dihydro-2H-pyran-4-yl)-2-(3-ethyl-ureido)-[1,2,4]triazolo[1,5-a]pyridine-5-carboxylic acid ethyl amide Using the general procedure of Example 31, Step 2, but substituting 4-(4,4,5,5-tetramethyl-[1,3,2]dioxaborolan-2-yl)-3,6-dihydro-2H-pyran for 2-methoxy-3-pyridineboronic acid, the title compound was obtained. Solid residue was purified by silica gel chromatography (gradient: 0-5% methanol/dichloromethane) to give 7-(3,6-dihydro-2H-pyran-4-yl)-2-(3-ethyl-ureido)-[1,2,4]triazolo[1,5-a]pyridine-5-carboxylic acid ethyl amide as a solid. MS (APCI10V+) 359.

Example 34

2-(3-Ethyl-ureido)-7-(6-fluoro-pyridin-3-yl)-[1,2,4]triazolo[1,5-a]pyridine-5-carboxylic acid ethylamide Step 1:

Bis(pinacolato)diboron (0.22 g, 0.85 mmol) was added to 5-bromo-2-fluoropyridine (0.15, 0.85 mmol) dissolved in DMF (6 mL). [1,1'-Bis(diphenylphosphino)-ferrocene) dichloropalladium (II) complex with dichloromethane (0.042 g, 0.051 mmol) followed by potassium acetate (0.25 g, 2.6 mmol) were added, then the reaction mixture was degassed (3x's) using $N_2$ and vacuum before warming to 80° C. The reaction was held at temperature for 2 hours before cooling to room temperature.

Step 2:

7-Bromo-2-(3-ethyl-ureido)-[1,2,4]triazolo[1,5-a]pyridine-5-carboxylic acid ethyl amide, which may be prepared as described in Example 6, (0.15 g, 0.42 mmol), [1,1'-Bis(diphenylphosphino)-ferrocene) dichloropalladium (II) complex with dichloromethane (0.02 g, 0.03 mmol) and sodium carbonate (0.327, 3.1 mml) were added to the reaction solution from Step 1. The reaction mixture was degassed (and heated to 80° C. for 4 hours. Next, the reaction mixture was cooled to room temperature and saturated $NaHCO_3$ (50 mL) was added. The product was extracted (5% MeOH/dichloromethane) and the solvent was removed. The crude product was purified by silica gel chromatography (gradient: 0-5% MeOH in dichloromethane) to give 2-(3-ethyl-ureido)-7-(6-fluoro-pyridin-3-yl)-[1,2,4]triazolo[1,5-a]pyridine-5-carboxylic acid ethyl amide as a solid. MS (APCI10V+) 372.

Example 35

7-(2,6-Dimethyl-pyridin-3-yl)-2-(3-ethyl-ureido)-[1,2,4]triazolo[1,5-a]pyridine-5-carboxylic acid ethyl amide Step 1:

Using the general procedure of Example 34, Step 1, but substituting 3-bromo-2,6-dimethyl-pyridine (0.150, 0.806 mmol), for 2-bromo-2-fluoro-pyridine 2,6-Dimethyl-3-(4,4,5,5-tetramethyl-[1,3,2]dioxaborolan-2-yl)-pyridine was obtained. The compound was not isolated and the resulting reaction mixture was used directly in Step 2.

Step 2:

7-(2,6-Dimethyl-pyridin-3-yl)-2-(3-ethyl-ureido)-[1,2,4]triazolo[1,5-a]pyridine-5-carboxylic acid ethyl amide was produced using the general method of Example 34, Step 2, with the substitution of the product of Step 1 above as one of the starting materials. The resulting material was purified by silica gel chromatography (10% MeOH in dichloromethane) to give 7-(2,6-Dimethyl-pyridin-3-yl)-2-(3-ethyl-ureido)-[1,2,4]triazolo[1,5-a]pyridine-5-carboxylic acid ethyl amide as a solid. MS (APCI10V−) 380.

Examples 36-103

General Procedure for the Synthesis of the $C^5$-amides (Method A)

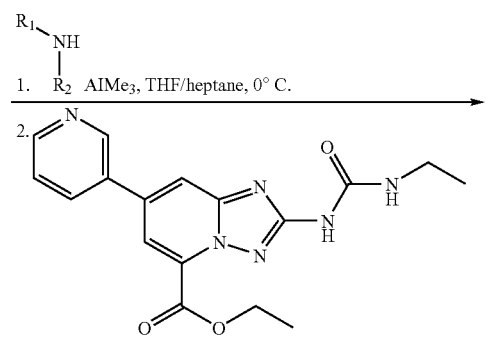

-continued

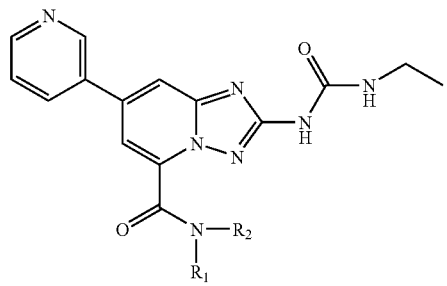

A solution of trimethylaluminum (2.0 M in heptane, 0.3 mL, 0.6 mmol) was added to a solution of an amine (appropriately substituted to yield the desired final product, i.e. —NR$^1$R$^2$) (0.6 mmol) in tetrahydrofuran (1 mL) at 0° C. The solution was then kept at 0° C. for 30 min. A suspension of 2-(3-ethyl-ureido)-7-pyridin-3-yl-[1,2,4]triazolo[1,5-a]pyridine-5-carboxylic acid ethyl ester, which may be prepared as described in Example 16, (42 mg, 0.12 mmol) in tetrahydrofuran (1 mL) was then added to the amine-trimethylaluminum complex at 0° C. The reaction mixture was then shaken at room temperature for 19 hours. Ethyl acetate (5 mL) was added to the reaction mixture followed by careful addition of saturated aqueous sodium potassium tartrate (4 mL). The layers were separated, and the organic layer was dried (magnesium sulfate), filtered, and concentrated under reduced pressure. The crude product was then purified by via reverse phase preparative MPLC or reverse phase preparative HPLC.

General Procedure for the Synthesis of the $C^7$-Aryl and $C^7$-Heteroaryl Derivatives (Method B):

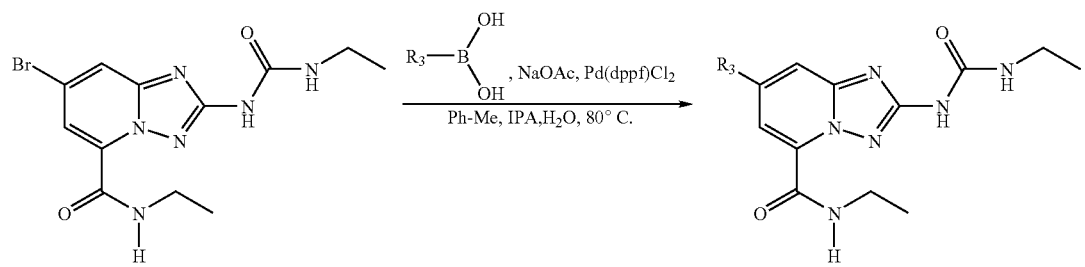

To a reaction vessel containing an appropriately substituted boronic acid derivative (i.e. $R^3$—B—$(OH)_2$, 0.190 mmol) was added a suspension of 7-bromo-2-(3-ethyl-ureido)-[1,2,4]triazolo[1,5-a]pyridine-5-carboxylic acid ethylamide, which may be prepared as in Example 8, (50 mg, 0.14 mmol) in toluene (2 mL). Isopropyl alcohol (0.5 mL), sodium acetate (52 mg, 0.63 mmol) in water (0.5 mL), and Pd(dppf)Cl$_2$ complex with dichloromethane (1:1) (4 mg, 0.005 mmol) were added in sequential order. The reaction mixture was then heated at 80° C. on a shaker block for 7 hours. After cooling the mixture to room temperature, ethyl acetate (3 mL) and saturated aqueous sodium bicarbonate (1 mL) were added. The layers were mixed vigorously and then separated. The organic layer was then dried (magnesium sulfate), filtered, and concentrated under reduced pressure. The crude product was then purified via reverse phase preparative HPLC.

Purification Methods

Preparative MPLC, column: Biotage KP-C18-HS, 60 Å, particle size 60 microns; solvent gradient: 99% water/1% acetonitrile to 40% water/60% acetonitrile over 1000 mL, flow rate=37 mL/min. Example: 36.

Preparative HPLC method 1, column: Phenomenex Luna C18(2), 5 microns; solvent gradient: 20% acetonitrile (0.1% formic acid)/80% water (0.1% formic acid) hold for 3 minutes then to 100% acetonitrile (0.1% formic acid) over 5.50 minutes then hold at 100% acetonitrile (0.1% formic acid) for 1.50 minutes; flow rate=30 mL/min. Examples: 37-48.

Preparative HPLC method 2, column: Waters Atlantis dC18 (19×100 mm, 5 microns); solvent gradient: 15% acetonitrile (3% 1-propanol)/85% water (3% 1-propanol) hold for 1 minute then to 100% acetonitrile (3% 1-propanol) over 7.50 minutes then hold at 100% acetonitrile (3% 1-propanol) for 1.50 minutes; flow rate=30 mL/min. Examples: 74-77 and 49-51.

Preparative HPLC method 3, column: Waters Atlantis dC18 (19×100 mm, 5 microns); solvent gradient: 15% acetonitrile (3% 1-propanol)/85% water (3% 1-propanol) hold for 2.50 minutes then to 100% acetonitrile (3% 1-propanol) over 6.00 minutes then hold at 100% acetonitrile (3% 1-propanol) for 1.50 minutes; flow rate=30 mL/min. Examples: 52-73, 78-81, and 103.

Preparative HPLC method 4, column: Waters XTerra™ MSC18 (19×100 mm, 5 microns); solvent gradient: 20% acetonitrile (0.1% ammonium hydroxide)/80% water (0.1% ammonium hydroxide) for 1 minute then to 100% acetonitrile (0.1% ammonium hydroxide) over 5 minutes then hold at 100% acetonitrile (0.1% ammonium hydroxide) for 4 minutes; flow rate=30 mL/min. Examples: 83, 84, 85, 94-102.

Preparative HPLC method 5, column: Waters XTerra™ MSC18 (19×100 mm, 5 microns); solvent gradient: 15% acetonitrile (0.1% ammonium hydroxide)/85% water (0.1% ammonium hydroxide) for 1 minute then to 100% acetonitrile (0.1% ammonium hydroxide) over 6 minutes then hold at 100% acetonitrile (0.1% ammonium hydroxide) for 3 minutes; flow rate=30 mL/min. Examples: 86-93.

TABLE 1

| Example | Structure | Name | Method | Mass Spec |
|---|---|---|---|---|
| 36 | 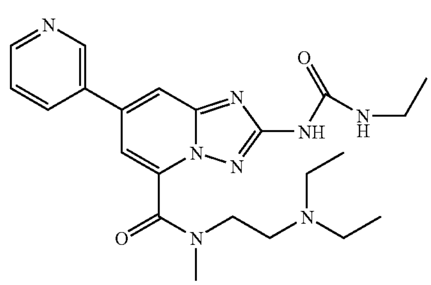 | 2-(3-Ethyl-ureido)-7-pyridin-3-yl-[1,2,4]triazolo[1,5-a]pyridine-5-carboxylic acid (2-diethylamino-ethyl)-methyl-amide | A | 439.2 (M + 1) |
| 37 | 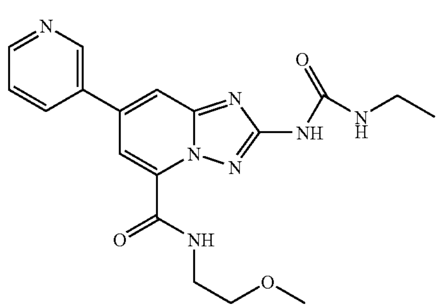 | 2-(3-Ethyl-ureido)-7-pyridin-3-yl-[1,2,4]triazolo[1,5-a]pyridine-5-carboxylic acid (2-methoxy-ethyl)-amide | A | 384.2 (M + 1), |

TABLE 1-continued

| Example | Structure | Name | Method | Mass Spec |
|---|---|---|---|---|
| 38 | 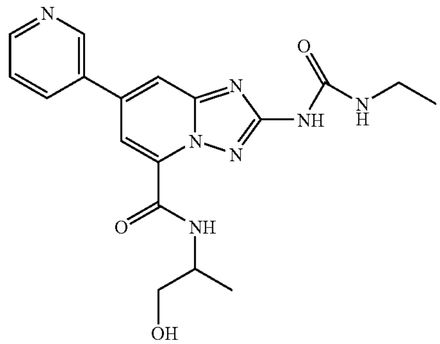 | 2-(3-Ethyl-ureido)-7-pyridin-3-yl-[1,2,4]triazolo[1,5-a]pyridine-5-carboxylic acid (2-hydroxy-1-methyl-ethyl)-amide | A | 384.2 (M + 1), |
| 39 | 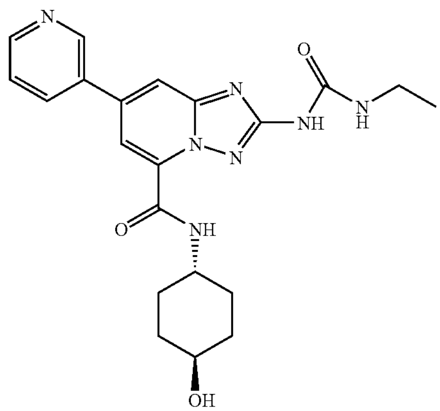 | trans-2-(3-Ethyl-ureido)-7-pyridin-3-yl-[1,2,4]triazolo[1,5-a]pyridine-5-carboxylic acid (4-hydroxy-cyclohexyl)-amide | A | 424.3 (M + 1) |
| 40 | 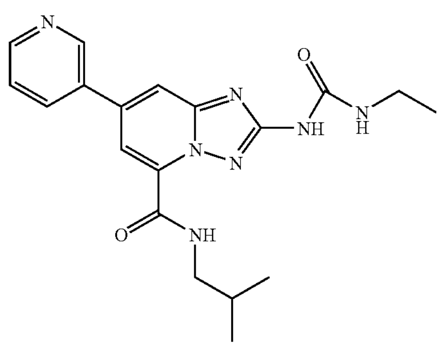 | 2-(3-Ethyl-ureido)-7-pyridin-3-yl-[1,2,4]triazolo[1,5-a]pyridine-5-carboxylic acid isobutyl-amide | A | 382.2 (M + 1),. |
| 41 | 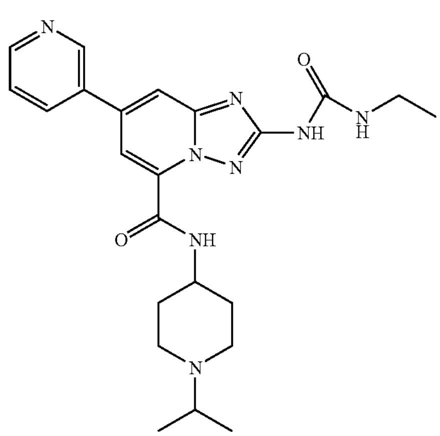 | 2-(3-Ethyl-ureido)-7-pyridin-3-yl-[1,2,4]triazolo[1,5-a]pyridine-5-carboxylic acid (1-isopropyl-piperidin-4-yl)-amide | A | 451.3 (M + 1). |

TABLE 1-continued

| Example | Structure | Name | Method | Mass Spec |
|---|---|---|---|---|
| 42 | 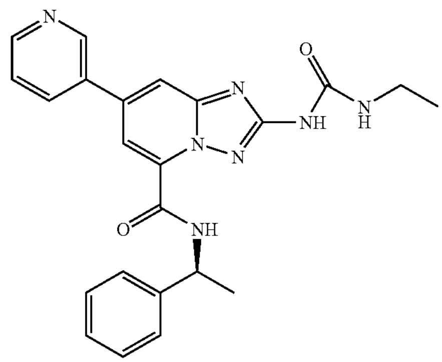 | (S)-2-(3-Ethyl-ureido)-7-pyridin-3-yl-[1,2,4]triazolo[1,5-a]pyridine-5-carboxylic acid (1-phenyl-ethyl)-amide | A | 430.3 (M + 1), |
| 43 | 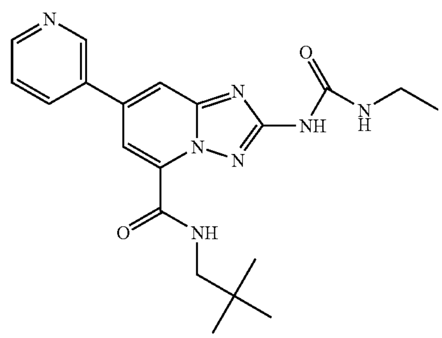 | 2-(3-Ethyl-ureido)-7-pyridin-3-yl-[1,2,4]triazolo[1,5-a]pyridine-5-carboxylic acid (2,2-dimethyl-propyl)-amide | A | 396.3 (M + 1) |
| 44 | 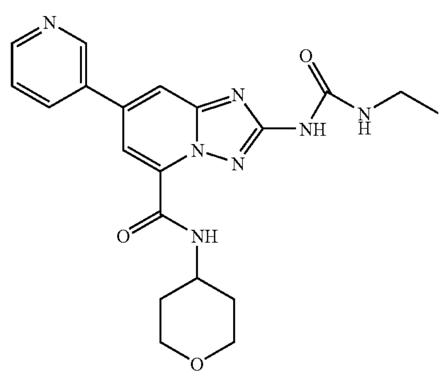 | 2-(3-Ethyl-ureido)-7-pyridin-3-yl-[1,2,4]triazolo[1,5-a]pyridine-5-carboxylic acid (tetrahydro-pyran-4-yl)-amide | A | 410.3 (M + 1) |
| 45 | 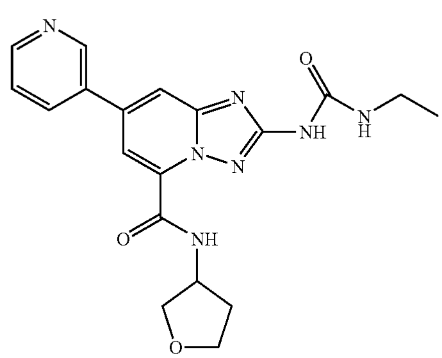 | 2-(3-Ethyl-ureido)-7-pyridin-3-yl-[1,2,4]triazolo[1,5-a]pyridine-5-carboxylic acid (tetrahydro-furan-3-yl)-amide | A | 396.2 (M + 1) |

TABLE 1-continued

| Example | Structure | Name | Method | Mass Spec |
|---|---|---|---|---|
| 46 | 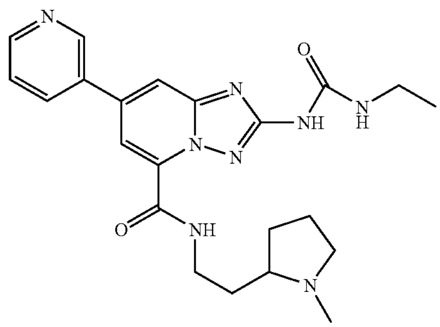 | 2-(3-Ethyl-ureido)-7-pyridin-3-yl-[1,2,4]triazolo[1,5-a]pyridine-5-carboxylic acid [2-(1-methyl-pyrrolidin-2-yl)-ethyl]-amide | A | 437.3 (M + 1) |
| 47 | 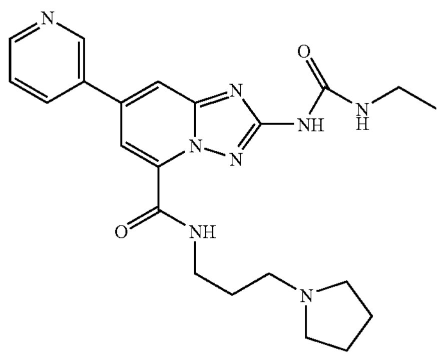 | 2-(3-Ethyl-ureido)-7-pyridin-3-yl-[1,2,4]triazolo[1,5-a]pyridine-5-carboxylic acid (3-pyrrolidin-1-yl-propyl)-amide | A | 437.3 (M + 1) |
| 48 | 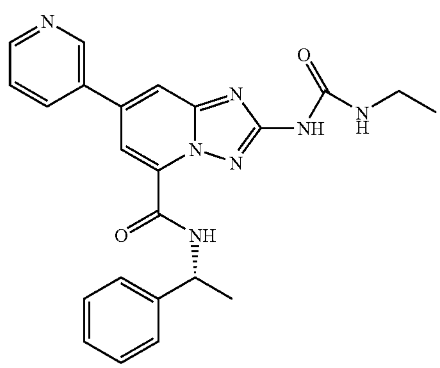 | (R)-2-(3-Ethyl-ureido)-7-pyridin-3-yl-[1,2,4]triazolo[1,5-a]pyridine-5-carboxylic acid (1-phenyl-ethyl)-amide | A | 430.3 (M + 1) |
| 49 | 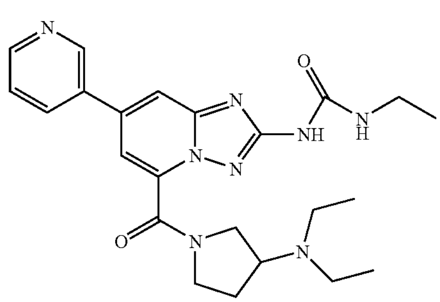 | 1-[5-(3-Diethylamino-pyrrolidine-1-carbonyl)-7-pyridin-3-yl-[1,2,4]triazolo[1,5-a]pyridin-2-yl]-3-ethyl-urea | A | 451.3 (M + 1) |

TABLE 1-continued

| Example | Structure | Name | Method | Mass Spec |
| --- | --- | --- | --- | --- |
| 50 | 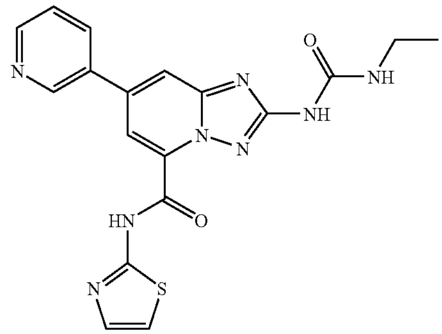 | 2-(3-Ethyl-ureido)-7-pyridin-3-yl-[1,2,4]triazolo[1,5-a]pyridine-5-carboxylic acid thiazol-2-ylamide | A | 409.1 (M +1) |
| 51 | 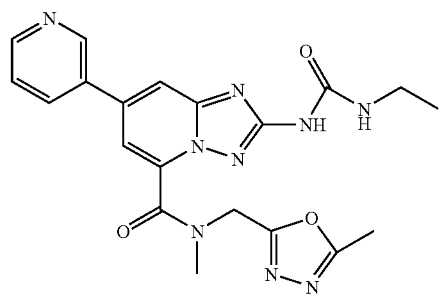 | 2-(3-Ethyl-ureido)-7-pyridin-3-yl-[1,2,4]triazolo[1,5-a]pyridine-5-carboxylic acid methyl-(5-methyl-[1,3,4]oxadiazol-2-ylmethyl)-amide | A | 436.2 (M + 1) |
| 52 | 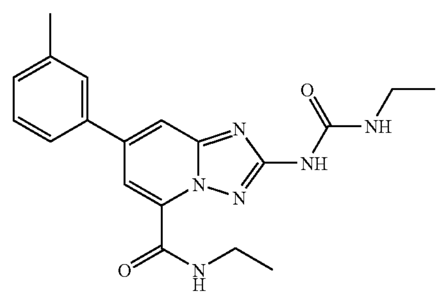 | 2-(3-Ethyl-ureido)-7-m-tolyl-[1,2,4]triazolo[1,5-a]pyridine-5-carboxylic acid ethylamide | B | 367.4 (M + 1) |
| 53 | 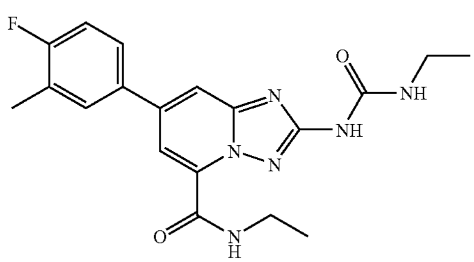 | 2-(3-Ethyl-ureido)-7-(4-fluoro-3-methyl-phenyl)-[1,2,4]triazolo[1,5-a]pyridine-5-carboxylic acid ethylamide | B | 385.4 (M + 1) |
| 54 | 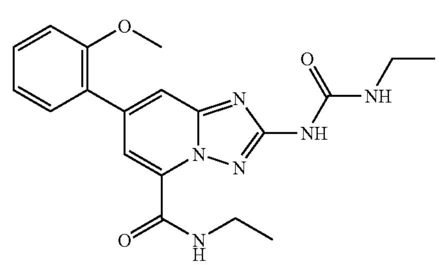 | 2-(3-Ethyl-ureido)-7-(2-methoxy-phenyl)-[1,2,4]triazolo[1,5-a]pyridine-5-carboxylic acid ethylamide | B | 383.3 (M + 1) |

TABLE 1-continued

| Example | Structure | Name | Method | Mass Spec |
|---|---|---|---|---|
| 55 | 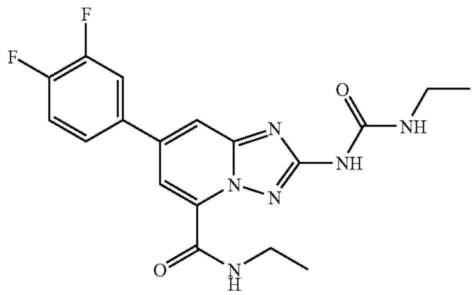 | 7-(3,4-Difluoro-phenyl)-2-(3-ethyl-ureido)-[1,2,4]triazolo[1,5-a]pyridine-5-carboxylic acid ethylamide | B | 389.3 (M + 1) |
| 56 | 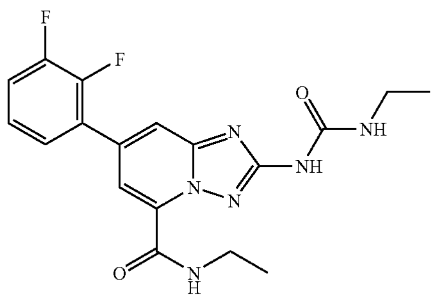 | 7-(2,3-Difluoro-phenyl)-2-(3-ethyl-ureido)-[1,2,4]triazolo[1,5-a]pyridine-5-carboxylic acid ethylamide | B | 389.3 (M + 1) |
| 57 | 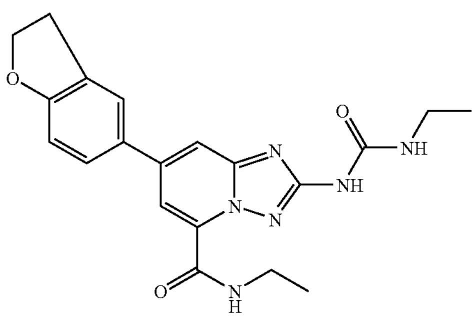 | 7-(2,3-Dihydro-benzofuran-5-yl)-2-(3-ethyl-ureido)-[1,2,4]triazolo[1,5-a]pyridine-5-carboxylic acid ethylamide | B | 395.4 (M + 1) |
| 58 | 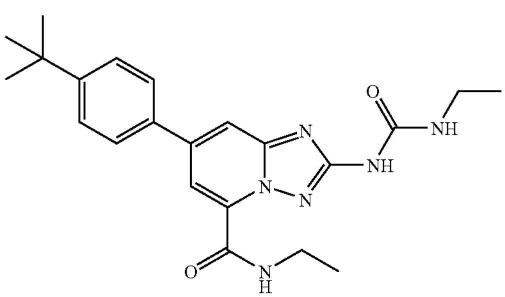 | 7-(4-tert-Butyl-phenyl)-2-(3-ethyl-ureido)-[1,2,4]triazolo[1,5-a]pyridine-5-carboxylic acid ethylamide | B | 409.4 (M + 1) |
| 59 | 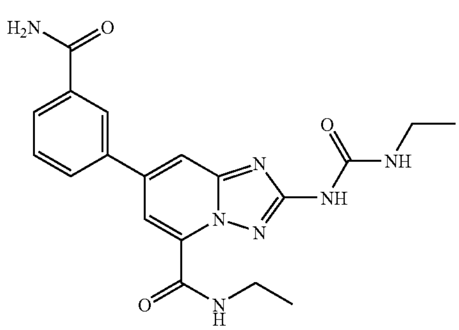 | 7-(3-Carbamoyl-phenyl)-2-(3-ethyl-ureido)-[1,2,4]triazolo[1,5-a]pyridine-5-carboxylic acid ethylamide | B | 396.3 (M + 1) |

TABLE 1-continued

| Example | Structure | Name | Method | Mass Spec |
|---|---|---|---|---|
| 60 | 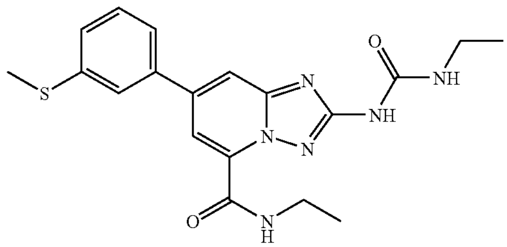 | 2-(3-Ethyl-ureido)-7-(3-methyl-sulfanyl-phenyl)-[1,2,4]triazolo[1,5-a]pyridine-5-carboxylic acid ethylamide | B | 399.3 (M + 1) |
| 61 | 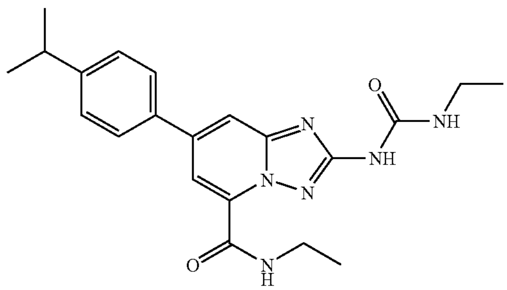 | 2-(3-Ethyl-ureido)-7-(4-isopropyl-phenyl)-[1,2,4]triazolo[1,5-a]pyridine-5-carboxylic acid ethylamide | B | 395.4 (M + 1) |
| 62 | 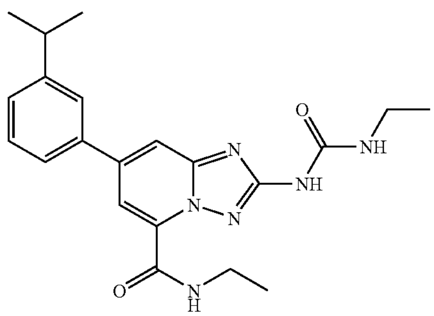 | 2-(3-Ethyl-ureido)-7-(3-isopropyl-phenyl)-[1,2,4]triazolo[1,5-a]pyridine-5-carboxylic acid ethylamide | B | 395.4 (M + 1) |
| 63 | 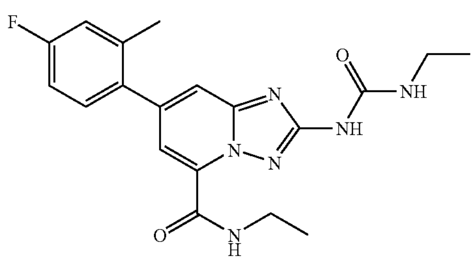 | 2-(3-Ethyl-ureido)-7-(4-fluoro-2-methyl-phenyl)-[1,2,4]triazolo[1,5-a]pyridine-5-carboxylic acid ethylamide | B | LC/MS method G: 389.3 (M + 1), 98.3%, 3.54 min |
| 64 | 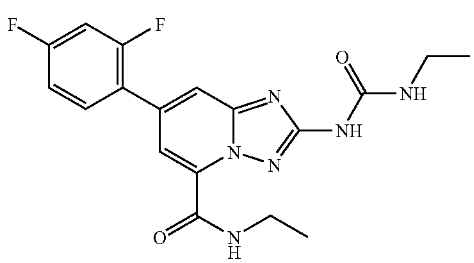 | 7-(2,4-Difluoro-phenyl)-2-(3-ethyl-ureido)-[1,2,4]triazolo[1,5-a]pyridine-5-carboxylic acid ethylamide | B | 378.3 (M + 1) |

TABLE 1-continued

| Example | Structure | Name | Method | Mass Spec |
|---|---|---|---|---|
| 65 | 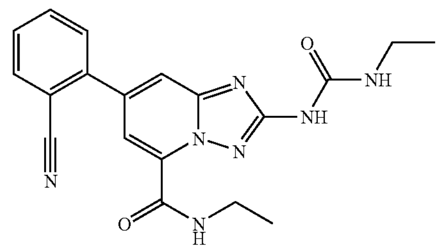 | 7-(2-Cyano-phenyl)-2-(3-ethyl-ureido)-[1,2,4]triazolo[1,5-a]pyridine-5-carboxylic acid ethylamide | B | 389.3 (M + 1) |
| 66 | 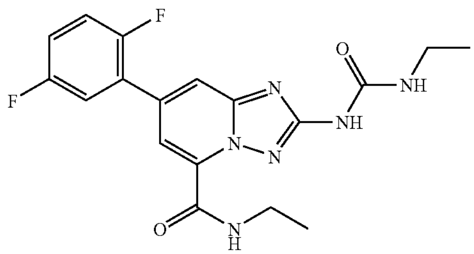 | 7-(2,5-Difluoro-phenyl)-2-(3-ethyl-ureido)-[1,2,4]triazolo[1,5-a]pyridine-5-carboxylic acid ethylamide | B | 387.3 (M + 1) |
| 67 | 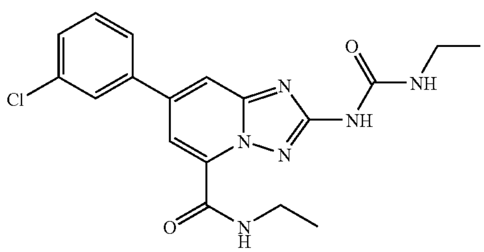 | 7-(3-Chloro-phenyl)-2-(3-ethyl-ureido)-[1,2,4]triazolo[1,5-a]pyridine-5-carboxylic acid ethylamide | B | 367.4 (M + 1) |
| 68 | 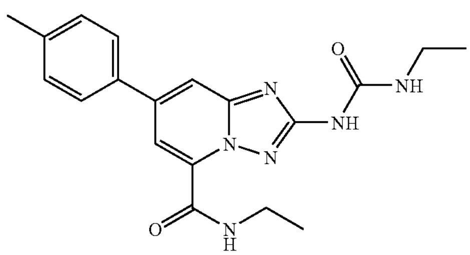 | 2-(3-Ethyl-ureido)-7-p-tolyl-[1,2,4]triazolo[1,5-a]pyridine-5-carboxylic acid ethylamide | B | 371.3 (M + 1) |
| 69 | 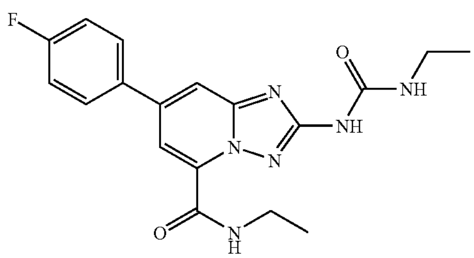 | 2-(3-Ethyl-ureido)-7-(4-fluoro-phenyl)-[1,2,4]triazolo[1,5-a]pyridine-5-carboxylic acid ethylamide | B | 371.3 (M + 1) |
| 70 | 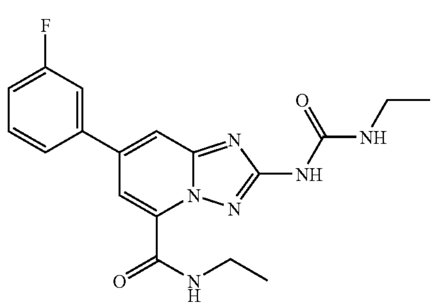 | 2-(3-Ethyl-ureido)-7-(3-fluoro-phenyl)-[1,2,4]triazolo[1,5-a]pyridine-5-carboxylic acid ethylamide | B | 353.3 (M + 1) |

TABLE 1-continued

| Example | Name | Method | Mass Spec |
|---|---|---|---|
| 71 | 2-(3-Ethyl-ureido)-7-phenyl-[1,2,4]triazolo[1,5-a]pyridine-5-carboxylic acid ethylamide | B | 371.4 (M + 1) |
| 72 | 2-(3-Ethyl-ureido)-7-(2-fluoro-phenyl)-[1,2,4]triazolo[1,5-a]pyridine-5-carboxylic acid ethylamide | B | 371.4 (M + 1) |
| 73 | 2-(3-Ethyl-ureido)-7-o-tolyl-[1,2,4]triazolo[1,5-a]pyridine-5-carboxylic acid ethylamide | B | 367.4 (M + 1), |
| 74 | 1-Ethyl-3-[5-(2-isopropyl-pyrrolidine-1-carbonyl)-7-pyridin-3-yl-[1,2,4]triazolo[1,5-a]pyridin-2-yl]-urea | A | 422.3 (M + 1) |
| 75 | 2-(3-Ethyl-ureido)-7-pyridin-3-yl-[1,2,4]triazolo[1,5-a]pyridine-5-carboxylic acid cyclobutylamide | A | 380.2 (M + 1) |

TABLE 1-continued

| Example | Structure | Name | Method | Mass Spec |
|---|---|---|---|---|
| 76 | 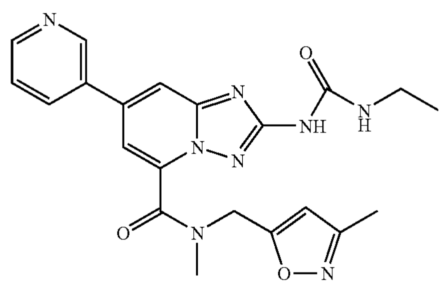 | 2-(3-Ethyl-ureido)-7-pyridin-3-yl-[1,2,4]triazolo[1,5-a]pyridine-5-carboxylic acid methyl-(3-methyl-isoxazol-5-yl-methyl)-amide | A | 435.2 (M + 1) |
| 77 | 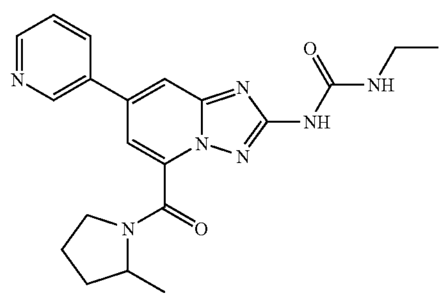 | 1-Ethyl-3-[5-(2-methyl-pyrrolidine-1-carbonyl)-7-pyridin-3-yl-[1,2,4]triazolo[1,5-a]pyridin-2-yl]-urea | A | 394.2 (M + 1) |
| 78 | 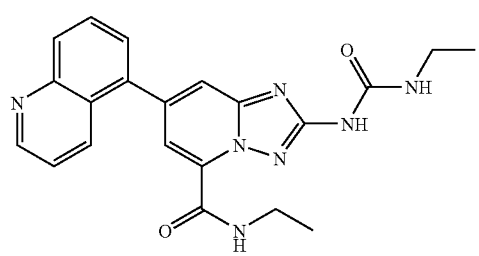 | 2-(3-Ethyl-ureido)-7-quinolin-5-yl-[1,2,4]triazolo[1,5-a]pyridine-5-carboxylic acid ethylamide | B | 404.4 (M + 1) |
| 79 | 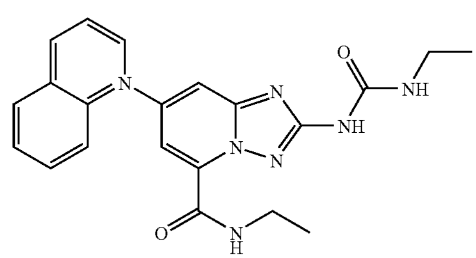 | 2-(3-Ethyl-ureido)-7-quinolin-8-yl-[1,2,4]triazolo[1,5-a]pyridine-5-carboxylic acid ethylamide | B | 404.4 (M + 1) |
| 80 | 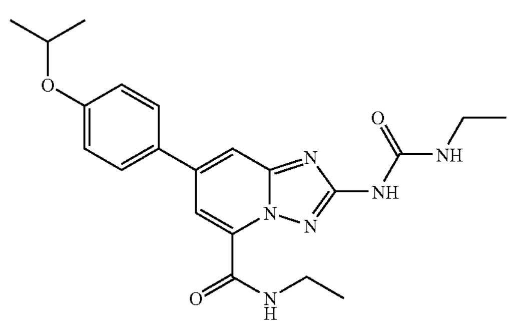 | 2-(3-Ethyl-ureido)-7-(4-isopropoxy-phenyl)-[1,2,4]triazolo[1,5-a]pyridine-5-carboxylic acid ethylamide | B | 411.4 (M + 1) |

TABLE 1-continued

| Example | Structure | Name | Method | Mass Spec |
|---|---|---|---|---|
| 81 | 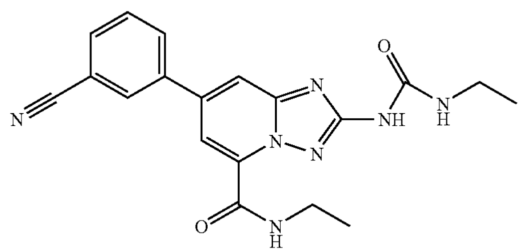 | 7-(3-Cyano-phenyl)-2-(3-ethyl-ureido)-[1,2,4]triazolo[1,5-a]pyridine-5-carboxylic acid ethylamide | B | 378.3 (M + 1) |
| 82 | 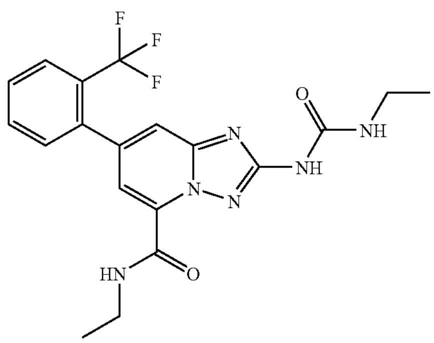 | 2-(3-Ethyl-ureido)-7-(2-trifluoromethyl-phenyl)-[1,2,4]triazolo[1,5-a]pyridine-5-carboxylic acid ethylamide | B | 421.3 (M + 1) |
| 84 | 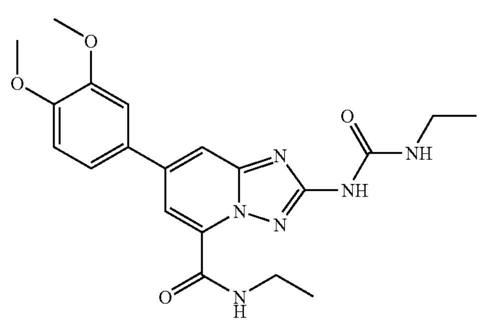 | 7-(3,4-Dimethoxy-phenyl)-2-(3-ethyl-ureido)-[1,2,4]triazolo[1,5-a]pyridine-5-carboxylic acid ethylamide | B | 413.3 (M + 1) |
| 85 | 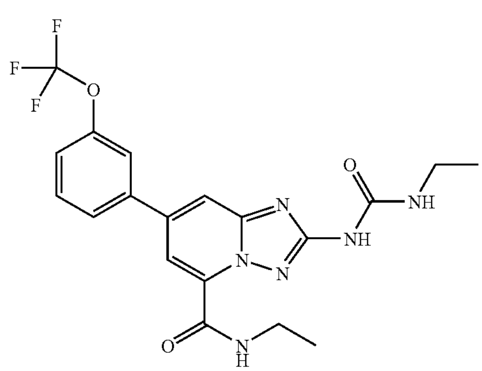 | 2-(3-Ethyl-ureido)-7-(3-trifluoromethoxy-phenyl)-[1,2,4]triazolo[1,5-a]pyridine-5-carboxylic acid ethylamide | B | 437.2 (M + 1) |

TABLE 1-continued

| Example | Structure | Name | Method | Mass Spec |
|---|---|---|---|---|
| 86 | 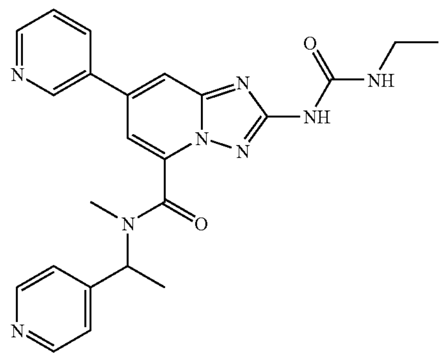 | 2-(3-Ethyl-ureido)-7-pyridin-3-yl-[1,2,4]triazolo[1,5-a]pyridine-5-carboxylic acid methyl-(1-pyridin-4-yl-ethyl)-amide | A | 445.3 (M + 1) |
| 87 | 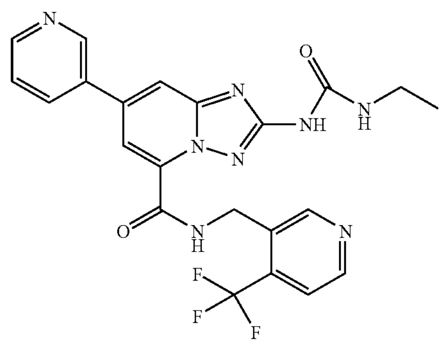 | 2-(3-Ethyl-ureido)-7-pyridin-3-yl-[1,2,4]triazolo[1,5-a]pyridine-5-carboxylic acid (4-trifluoromethyl-pyridin-3-ylmethyl)-amide | A | 485.3 (M + 1) |
| 88 | 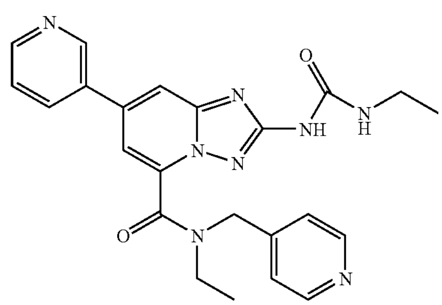 | 2-(3-Ethyl-ureido)-7-pyridin-3-yl-[1,2,4]triazolo[1,5-a]pyridine-5-carboxylic acid ethyl-pyridin-4-ylmethyl-amide | A | 445.3 (M + 1) |
| 89 | 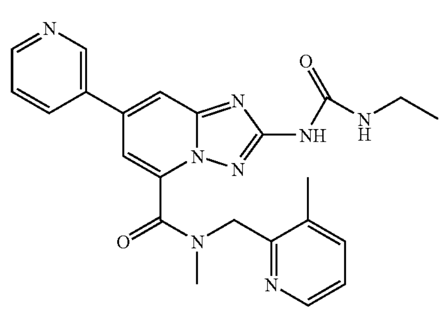 | 2-(3-Ethyl-ureido)-7-pyridin-3-yl-[1,2,4]triazolo[1,5-a]pyridine-5-carboxylic acid methyl-(3-methyl-pyridin-2-yl-methyl)-amide | A | 445.3 (M + 1) |

TABLE 1-continued

| Example | Structure | Name | Method | Mass Spec |
|---|---|---|---|---|
| 90 | 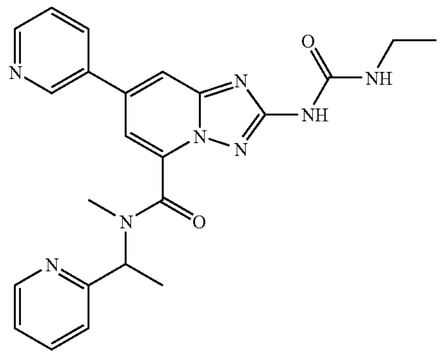 | 2-(3-Ethyl-ureido)-7-pyridin-3-yl-[1,2,4]triazolo[1,5-a]pyridine-5-carboxylic acid methyl-(1-pyridin-2-yl-ethyl)-amide | A | 445.3 (M + 1) |
| 91 | 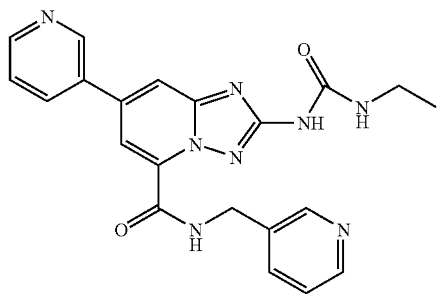 | 2-(3-Ethyl-ureido)-7-pyridin-3-yl-[1,2,4]triazolo[1,5-a]pyridine-5-carboxylic acid (pyridin-3-ylmethyl)-amide | A | 417.2 (M + 1) |
| 92 | 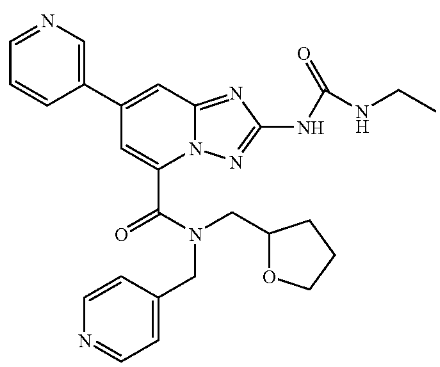 | 2-(3-Ethyl-ureido)-7-pyridin-3-yl-[1,2,4]triazolo[1,5-a]pyridine-5-carboxylic acid pyridin-4-ylmethyl-(tetrahydro-furan-2-ylmethyl)-amide | A | 501.4 (M + 1) |
| 93 | 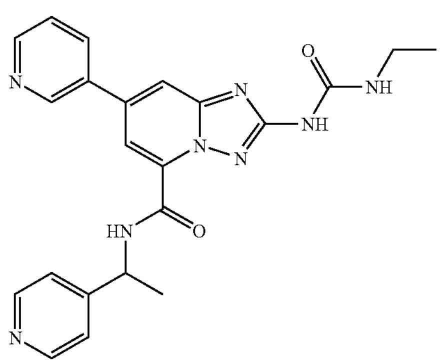 | 2-(3-Ethyl-ureido)-7-pyridin-3-yl-[1,2,4]triazolo[1,5-a]pyridine-5-carboxylic acid (1-pyridin-4-yl-ethyl)-amide | A | 431.3 (M + 1) |

TABLE 1-continued

| Example | Structure | Name | Method | Mass Spec |
|---|---|---|---|---|
| 94 | 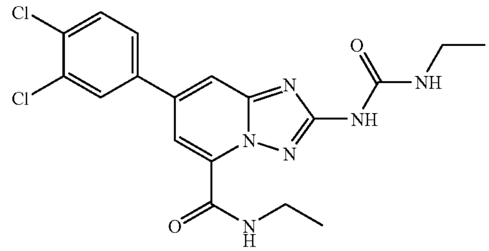 | 7-(3,4-Dichloro-phenyl)-2-(3-ethyl-ureido)-[1,2,4]triazolo[1,5-a]pyridine-5-carboxylic acid ethylamide | B | Rick? |
| 95 | 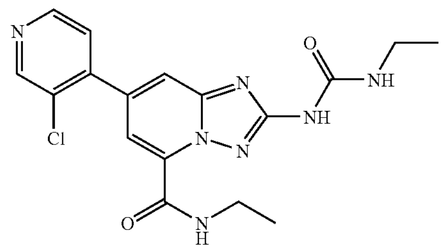 | 7-(3-Chloro-pyridin-4-yl)-2-(3-ethyl-ureido)-[1,2,4]triazolo[1,5-a]pyridine-5-carboxylic acid ethylamide | B | 388.3 (M + 1) |
| 96 | 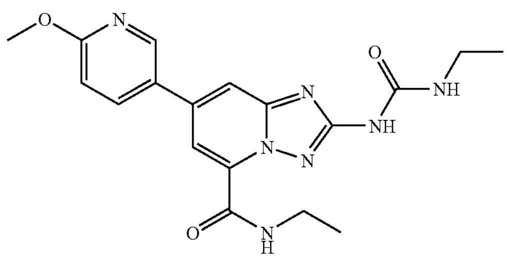 | 2-(3-Ethyl-ureido)-7-(6-methoxy-pyridin-3-yl)-[1,2,4]triazolo[1,5-a]pyridine-5-carboxylic acid ethylamide | B | 384.4 (M + 1) |
| 97 | 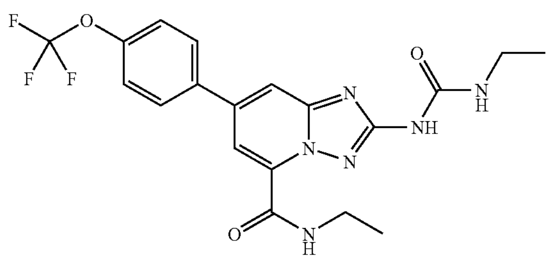 | 2-(3-Ethyl-ureido)-7-(4-trifluoromethoxy-phenyl)-[1,2,4]triazolo[1,5-a]pyridine-5-carboxylic acid ethylamide | B | 437.3 (M + 1) |
| 98 | 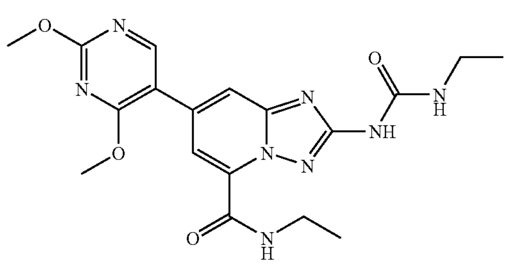 | 7-(2,4-Dimethoxy-pyrimidin-5-yl)-2-(3-ethyl-ureido)-[1,2,4]triazolo[1,5-a]pyridine-5-carboxylic acid ethylamide | B | 415.4 (M + 1) |
| 99 | 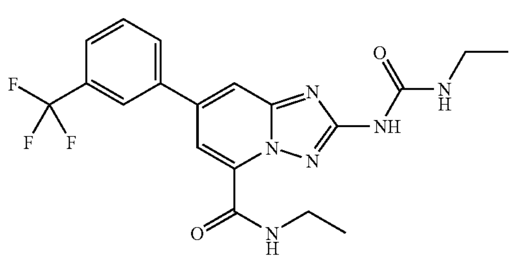 | 2-(3-Ethyl-ureido)-7-(3-trifluoromethyl-phenyl)-[1,2,4]triazolo[1,5-a]pyridine-5-carboxylic acid ethylamide | B | 421.3 (M + 1), |

TABLE 1-continued

| Example | Structure | Name | Method | Mass Spec |
|---|---|---|---|---|
| 100 | 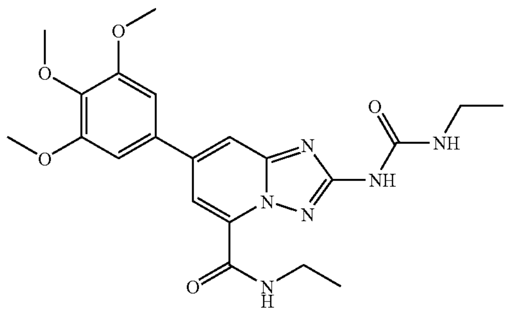 | 2-(3-Ethyl-ureido)-7-(3,4,5-trimethoxy-phenyl)-[1,2,4]triazolo[1,5-a]pyridine-5-carboxylic acid ethylamide | B | 443.4 (M + 1) |
| 101 | 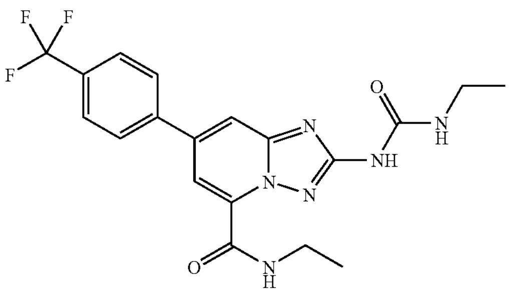 | 2-(3-Ethyl-ureido)-7-(4-trifluoromethyl-phenyl)-[1,2,4]triazolo[1,5-a]pyridine-5-carboxylic acid ethylamide | B | 421.3 (M + 1) |
| 102 | 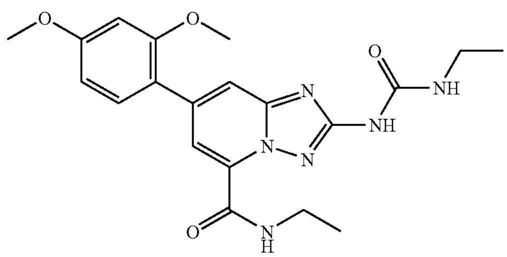 | 7-(2,4-Dimethoxy-phenyl)-2-(3-ethyl-ureido)-[1,2,4]triazolo[1,5-a]pyridine-5-carboxylic acid ethylamide | B | 413.3 (M + 1) |
| 103 | 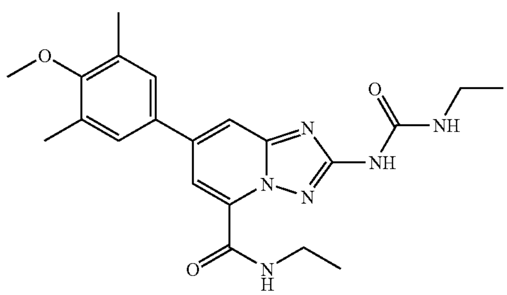 | 2-(3-Ethyl-ureido)-7-(4-methoxy-3,5-dimethyl-phenyl)-[1,2,4]triazolo[1,5-a]pyridine-5-carboxylic acid ethylamide | B | 411.4 (M + 1) |

Example 104

2-(3-Ethyl-ureido)-7-pyridin-3-yl-[1,2,4]triazolo[1,5-a]pyridine-5-carboxylic acid diethylamide Diethylamine (0.40 mL) in tetrahydrofuran (2.0 mL) was treated with trimethylaluminum (0.50 mL) and allowed to stir at 0° C. for 20 min. Next, 2-(3-ethyl-ureido)-7-pyridin-3-yl-[1,2,4]triazolo[1,5-a]pyridine-5-carboxylic acid ethyl ester, which may be produced as in Example 16, Step 2, (255 mg, 0.72 mmol) was added and warmed to room temperature. After 18 h the reaction was diluted with ethyl acetate (50 mL) and treated with an equal volume of saturated aqueous Rochelle salt. After 6 h the layers were separated and the organic layer was dried over magnesium sulfate and concentrated to provide 2-(3-ethyl-ureido)-7-pyridin-3-yl-[1,2,4]triazolo[1,5-a]pyridine-5-carboxylic acid diethylamide as a light yellow powder. MS (APCI+): m/z 382.2 (M+H).

Example 105

2-(3-Ethyl-ureido)-7-pyridin-3-yl-[1,2,4]triazolo[1,5-a]pyridine-5-carboxylic acid (2-dimethylamino-ethyl)-amide Step 1:

7-Bromo-2-(3-ethyl-ureido)-[1,2,4]triazolo[1,5-a]pyridine-5-carboxylic acid ethyl ester, (which may be produced as in Example 6, Step 4) (254 mg, 0.714 mmol) in ethanol (2.0 mL) was treated with dimethyl ethylene diamine (0.40 mL).

After 26 h a precipitate was removed by filtration, washed with ethanol and dried. Next, the crude material was taken up in 1N HCl and extracted with dichloromethane. The aqueous layer was neutralized with solid sodium bicarbonate, then extracted with dichloromethane, dried over magnesium sulfate, and concentrated to afford 7-bromo-2-(3-ethyl-ureido)-[1,2,4]triazolo[1,5-a]pyridine-5-carboxylic acid (2-dimethylamino-ethyl)-amide. MS (APCI+): m/z 398.2 (M+H).

Step 2:

The product of Step 1 (37.5 mg, 0.094 mmol), pyridyl-2-boronic acid (20.0 mg, 0.163 mmol), sodium carbonate (50.0 mg, 0.472 mmol) and Pd(dppf)Cl2 (5.00 mg) in 7:3:2 DME/H2O/EtOH (4.00 mL) were subjected to microwave radiation for 30 min at 80° C. Next, the crude was acidified with acetic acid and evaporated on silica then dry loaded. The crude was chomatographed (0-5% MeOH/CH$_2$Cl$_2$) to afford 2-(3-ethyl-ureido)-7-pyridin-3-yl-[1,2,4]triazolo[1,5-a]pyridine-5-carboxylic acid (2-dimethylamino-ethyl)-amide. MS (APCI+): m/z 397.1 (M+H).

Example 106

2-(3-Ethyl-ureido)-7-pyridin-3-yl-[1,2,4]triazolo[1,5-a]pyridine-5-carboxylic acid 3,4-dimethoxy-benzylamide Step 1:

7-Bromo-2-(3-ethyl-ureido)-[1,2,4]triazolo[1,5-a]pyridine-5-carboxylic acid ethyl ester, which may be prepared as in Example 6, (253 mg, 0.714 mmol) and 3,4-dimethoxybenzylamine (0.55 mL) were taken up in ethanol (4.0 mL). After 24 h the precipitate was removed by filtration and washed with ethanol to afford 7-bromo-2-(3-ethyl-ureido)-[1,2,4]triazolo[1,5-a]pyridine-5-carboxylic acid 3,4-dimethoxy-benzylamide MS (APCI+): m/z 478.4 (M+H).

Step 2:

Using the general procedure of Example 105, Step 2, but substituting 7-bromo-2-(3-ethyl-ureido)-[1,2,4]triazolo[1,5-a]pyridine-5-carboxylic acid 3,4-dimethoxy-benzylamide as the starting material, 2-(3-ethyl-ureido)-7-pyridin-3-yl-[1,2,4]triazolo[1,5-a]pyridine-5-carboxylic acid 3,4-dimethoxy-benzylamide was produced as a white solid. MS (APCI+): m/z 476.1 (M+H).

Example 107

2-(3-Ethyl-ureido)-7-pyridin-3-yl-[1,2,4]triazolo[1,5-a]pyridine-5-carboxylic acid (3-amino-propyl)-amide 2-(3-Ethyl-ureido)-7-pyridin-3-yl-[1,2,4]triazolo[1,5-a]pyridine-5-carboxylic acid ethyl ester (which may be produced as in Example 16, Step 2, 201 mg, 0.563 mmol) in ethanol (15.0 mL) was charged with propylene diamine (0.30 mL). After 24 h the precipitate was removed by filtration, washed with ethanol and dried. Next the crude was taken up in 1N HCl and extracted with CH$_2$Cl$_2$. The aqueous layer was neutralized with solid sodium bicarbonate, then extracted with dichloromethane dried over magnesium sulfate and concentrated to afford the title compound. MS (APCI+): m/z 383.3 (M+H).

Example 108

1-(5-Butyryl-7-pyridin-3-yl-[1,2,4]triazolo[1,5-a]pyridine-2-yl)-3-ethyl-urea

Step 1:

Dimethylhydroxylamine HCl salt (1.40 g, 14.5 mmol) in THF (15.0 mL) was cooled to 0° C. and treated with trimethylaluminum (1.80 mL). After 1 h the solution was charged with 2-(3-ethyl-ureido)-7-pyridin-3-yl-[1,2,4]triazolo[1,5-a]pyridine-5-carboxylic acid ethyl ester (which may be produced as in Example 16, Step 1) (1.01 g, 2.84 mmol). After 20 h the reaction was diluted in ethyl acetate and charged with an equal amount of Rochelle salt. This biphasic solution was stirred rapidly for 4 h. then separated and the organic dried over magnesium sulfate and concentrated to afford 2-(3-ethyl-ureido)-7-pyridin-3-yl-[1,2,4]triazolo[1,5-a]pyridine-5-carboxylic acid methoxy-methyl-amide. MS (APCI+): m/z 370.4 (M+H).

Step 2:

Propylmagnesium chloride (1.00 mL) was cooled to 0° C. then charged with 2-(3-ethyl-ureido)-7-pyridin-3-yl-[1,2,4]triazolo[1,5-a]pyridine-5-carboxylic acid methoxy-methyl-amide (252 mg, 0.682 mmol) in tetrahydrofuran (4.00 mL). After 24 h the reaction was diluted with tetrahydrofuran and neutralized with NH$_4$Cl. The organic was dried over magnesium sulfate and concentrated leaving a solid. The crude was recrystallized (ethyl acetate) to afford the final product 1-(5-butyryl-7-pyridin-3-yl-[1,2,4]triazolo[1,5-a]pyridine-2-yl)-3-ethyl-urea. MS (APCI+): m/z 353.4 (M+H).

Example 109

1-(5-Cyclopropanecarbonyl-7-pyridin-3-yl-[1,2,4]triazolo[1,5-a]pyridine-2-yl)-3-ethyl-urea Using the general procedure of Example 108, except in Step 2 cyclopropylmagnesium bromide was substituted for propylmagnesium chloride, the title compound was produced. MS (APCI+): m/z 351.3 (M+H).

Example 110

1-Ethyl-3-(5-phenylacetyl-7-pyridin-3-yl-[1,2,4]triazolo[1,5-a]pyridine-2-yl)-urea Using the general procedure of Example 108, except in Step 2 substituting benzylmagnesium chloride for propylmagnesium chloride, the title compound was produced. MS (APCI+): m/z 401.3 (M+H).

Example 111

1-(5-Benzoyl-7-pyridin-3-yl-[1,2,4]triazolo[1,5-a]pyridine-2-yl)-3-ethyl-urea

Using the procedure of Example 108, except in Step 2 substituting phenylmagnesium bromide for propylmagnesium chloride, the title compound was produced. MS (APCI+): m/z 387.4 (M+H).

Example 112

1-Ethyl-3-[5-(1-methoxyimino-butyl)-7-pyridin-3-yl-[1,2,4]triazolo[1,5-a]pyridine-2-yl]-urea 1-(5-Butyryl-7-pyridin-3-yl-[1,2,4]triazolo[1,5-a]pyridin-2-yl)-3-ethyl-urea, which may be produced as in Example 108 (46.0 mg, 0.13 mmol) and O-methylhydroxylamine HCl (18.0 mg, 0.22 mmol) in ethanol (1.0 mL) were charged with sodium acetate trihydrate (55.0 mg, 0.41 mmol). After 24 h the reaction was concentrated then taken up in ethyl acetate and washed with saturated sodium bicarbonate. The organic was concentrated and the resulting oil chromatographed (0-10% isopropanol/$CH_2Cl_2$) to afford 1-ethyl-3-[5-(1-methoxyimino-butyl)-7-pyridin-3-yl-[1,2,4]triazolo[1,5-a]pyridine-2-yl]-urea. MS (APCI+): m/z 382.3 (M+H).

Example 113

1-Ethyl-3-(7-pyridin-3-yl-5-pyrrolidin-1-ylmethyl-imidazo[1,2-a]pyridin-2-yl)-urea Step 1:
A suspension of 2-amino-7-bromo-[1,2,4]triazolo[1,5-a]pyridine-5-carboxylic acid ethyl ester, which may be produced as in Example 6, Step 3, (0.518 g, 1.82 mmol), ethylisocyanate (0.6 mL), and 5 drops of dibutyltin diacetate THF (6 mL) was heated in a closed vial at 130° C. for 20 min. in a CEM microwave reactor. The resulting slurry was then suspended in DCM (5 mL) and diethylether (25 mL) and the precipitate was collected by vacuum filtration, washed diethylether (2×15 mL) and dried under a stream of air to give 7-bromo-2-(3-ethyl-ureido)-[1,2,4]triazolo[1,5-a]pyridine-5-carboxylic acid ethyl ester as a solid.

Step 2:
A suspension of the product of Step 1 (0.145 g, 0.407 mmol), 3-pyridylboronic acid (0.092 g, 0.750 mmol), sodium acetate trihydrate (0.308 g, 2.08 mmol), and 0.013 g Pd(dppf)$Cl_2$-DCM in a mixture of 7:3:2 DME/water/EtOH (6 mL) was heated to 80° C. for 30 min in a closed vial in a CEM microwave reactor. The reaction was then partitioned between saturated sodium bicarbonate and DCM and the organic layer was collected. The aqueous layer was extracted with DCM (2×25 mL) and the combined organic layers were then extracted with 1N HCl (3×10 mL). The combined aqueous extracts were then neutralized with solid sodium bicarbonate and extracted with DCM (3×20 mL). The combined organic layers were then dried over sodium sulfate and evaporated in vacuo to give 2-(3-ethyl-ureido)-7-pyridin-3-yl-[1,2,4]triazolo[1,5-a]pyridine-5-carboxylic acid ethyl ester as a powder. MS (APCI+)=355.2

Step 3:
To a stirring suspension of the product of Step 2, (0.88 g, 2.5 mmol) in THF (40 mL) and MeOH (5 mL) was added sodium borohydride (1.02 g, 27 mmol). After 1 h the reaction was quenched by the addition of ca. 50 mL water and stirred 1 h to allow formation of a precipitate. The solid was rinsed with water (3×10 mL) and dried in vacuo to give the alcohol, 1-ethyl-3-(5-hydroxymethyl-7-pyridin-3-yl-[1,2,4]triazolo[1,5-a]pyridin-2-yl)-urea as a solid.

Step 4:
To a suspension of the product of Step 3 (0.108 g, 0.346 mmol), triphenylphosphine (0.125 g, 0.477 mmol) and imidazole (0.115 g, 1.69 mmol) in 5 mL DCM at 23° C. was added iodine (0.115 g, 0.453 mmol) and the reaction was stirred vigorously for 15 min. To this mixture was then added pyrrolidine (0.2 mL) and the reaction was stirred an additional 10 min until all solids had dissolved. The reaction was then applied directly to a silica gel column and chromatographed (gradient elution: 2-18% MeOH/DCM) to give the title compound as a powder MS (APCI+)=352.1

Example 114

1-(5-Cyclopropylaminomethyl-7-pyridin-3-yl-imidazo[1,2-a]pyridin-2-yl)-3-ethyl-urea Using the general procedure of Example 113, but substituting cyclopropyl amine for pyrrolidine in Step 4, the title compound as obtained. MS (APCI+)=352.3

Example 115

1-Ethyl-3-(5-ethylaminomethyl-7-pyridin-3-yl-imidazo[1,2-a]pyridin-2-yl)-urea

Using the general procedure of Example 113, but substituting ethyl amine (2N in THF) for pyrrolidine in Step 4, the title compound as obtained. MS (APCI+)=340.3

Example 116

7-(2-Dimethylamino-pyrimidin-5-yl)-2-(3-isopropyl-ureido)-imidazo[1,2-a]pyridine-5-carboxylic acid ethyl ester Step 1:
Bromo-2-(3-isopropyl-ureido)-[1,2,4]triazolo[1,5-a]pyridine-5-carboxylic acid ethyl ester was prepared using the general method described in Step 1 of Example 113, except substituting isopropyl isocyanate for ethyl isocyanate.

Step 2:
A suspension of the product produced above in Step 1 (0.197 g, 0.532 mmol), sodium acetate trihydrate (0.390 g, 2.64 mmol), 2-dimethylaminopyrimidine-5-boronic acid (0.18 g, 1.08 mmol), and bis[2-ethyloxazoline]palladium(II) diacetate (0.0083 g) in 10 mL of a 4:1:1 mixture of toluene, water, ethanol was heated to reflux. After 15 min. the reaction was cooled to 23° C. After 1 h a solid was collected by filtration and washed with diethylether (3×5 mL) then dried under a stream of air to give 7-(2-dimethylamino-pyrimidin-5-yl)-2-(3-isopropyl-ureido)-[1,2,4]triazolo[1,5-a]pyridine-5-carboxylic acid ethyl ester as a powder. MS (APCI+)=413.3

Example 117

7-(2-Dimethylamino-pyrimidin-5-yl)-2-(3-isopropyl-ureido)-imidazo[1,2-a]pyridine-5-carboxylic acid ethylamide A suspension of the product of Example 116, 7-(2-dimethylamino-pyrimidin-5-yl)-2-(3-isopropyl-ureido)-imidazo[1,2-a]pyridine-5-carboxylic acid ethyl ester (0.149 g, 0.361 mmol) in ethylamine (2 mL of a 70% aqueous solution) was treated with imidazole (2 g) and heated to 100° C. for 1 min until it became a homogeneous solution. The reaction was cooled to 23° C. and diluted with water (15 mL). The precipitated solid was collected by vacuum filtration then dried in vacuo to give 7-(2-dimethylamino-pyrimidin-5-yl)-2-(3-isopropyl-ureido)-[1,2,4]triazolo[1,5-a]pyridine-5-carboxylic acid ethylamide. MS (APCI+)=412.2

Example 118

2-(3-Ethyl-ureido)-7-(4-methoxy-phenyl)-imidazo[1,2-a]pyridine-5-carboxylic acid ethyl ester Using the general procedure of Example 116, Step 2, but substituting 7-bromo-2-(3-ethyl-ureido)-[1,2,4]triazolo[1,5-a]pyridine-5-carboxylic acid ethyl ester for bromo-2-(3-isopropyl-ureido)-[1,2,4]triazolo[1,5-a]pyridine-5-carboxylic acid ethyl ester and substituting 4-methoxyphenyl boronic acid for 2-dimethylaminopyrimidine-5-boronic acid the title compound was obtained as a solid. MS m/z 384.3 (M+H$^+$).

Example 119

2-(3-Ethyl-ureido)-7-(4-methoxy-phenyl)-imidazo[1,2-a]pyridine-5-carboxylic acid ethylamide Using the general procedure of Example 117, but substituting 2-(3-ethyl-ureido)-7-(4-methoxy-phenyl)-imidazo[1,2-a]pyridine-5-carboxylic acid ethyl ester for 7-(2-dimethylamino-pyrimidin-5-yl)-2-(3-isopropyl-ureido)-imidazo[1,2-a]pyridine-5-carboxylic acid ethyl ester the title compound was obtained as a solid. MS m/z 383.1 (M+H$^+$).

Example 120

1-Ethyl-3-[7-pyridin-3-yl-5-(pyrrolidine-1-carbonyl)-imidazo[1,2-a]pyridin-2-yl]-urea A dry mixture of imidazole (2 g) and 2-(3-ethyl-ureido)-7-pyridin-3-yl-[1,2,4]triazolo[1,5-a]pyridine-5-carboxylic acid ethyl ester (which may be produced as described in Example 16, Step 1) (0.160 g, 0.452 mmol) was heated until it became a homogeneous melt. It was then allowed to cool and solidify. To the solid was added pyrrolidine (0.1 mL) and the mixture was heated until it became a homogeneous melt, then allowed to cool to 23° C. Additional pyrrolidine (0.1 mL) was added and the reaction was heated at melt temperature for 30 sec. The reaction was cooled to RT and allowed to solidify. The solid was partitioned between water and EtOAc and the aqueous layer was extracted EtOAc (3×15 mL). The combined organic layers were then washed with brine and dried over sodium sulfate. Evaporation in vacuo gave a solid that was purified by silica gel chromatography (gradient elution 2-30% isopropanol/dichloromethane) to give the desired product. MS (APCI+)=380.1

Example 121

1-Ethyl-3-[5-(pyrrolidine-1-carbonyl)-7-pyrrolidin-1-yl-[1,2,4]triazolo[1,5-a]pyridin-2-yl]-urea To a suspension of 7-bromo-2-(3-ethyl-ureido)-[1,2,4]triazolo[1,5-a]pyridine-5-carboxylic acid ethyl ester (which may be produced as in Example 6) (0.080 g, 0.22 mmol) in dimethylsulfoxide (1 mL) was added pyrrolidine (0.2 mL). The reaction was stirred at 23° C. for 30 minutes then 80° C. for 3 days. The reaction was then diluted with water (2 mL), acidified with 1N aqueous hydrogen chloride, then neutralized with saturated aqueous sodium bicarbonate and extracted with ethyl acetate (3×20 mL). The combined organic extracts were dried over sodium sulfate and evaporated in vacuo to give a solid that was purified by silica gel chromatography (gradient elution: 0-20% isopropanol/dichloromethane) to give the title compound as a solid. MS (APCI)=372.2 [M+H]

Example 122

1-Ethyl-3-[5-(4-ethyl-thiazol-2-yl)-7-pyridin-3-yl-[1,2,4]triazolo[1,5-a]pyridin-2-yl]-urea Step 1:

A suspension of 2-(3-ethyl-ureido)-7-pyridin-3-yl-[1,2,4]triazolo[1,5-a]pyridine-5-carboxylic acid amide which may be produced as in Example 16, (1.03 g, 3.17 mmol) and Lawesson's reagent (Pederson, Lawesson, Bull. Soc. Chim. Belg. 1978, 87, 223, 229 & 293)(1.28 g, 3.17 mmol) in 40 mL of toluene/dioxane (1:1) mixture was heated to reflux for 12 h under nitrogen. Solvents were removed under reduced pressure to obtain a solid. This solid was dissolved in MeOH/CHCl$_3$, and dried onto silica gel. This material was then purified by column chromatography on silica gel (2-10% MeOH/CHCl$_3$ as eluent) to afford 2-(3-ethyl-ureido)-7-pyridin-3-yl-[1,2,4]triazolo[1,5-a]pyridine-5-carbothioic acid amide as a solid. LCMS (APCI$^+$) 342.

Step 2:

A mixture of the product of Step 1 (0.5 g, 1.47 mmol) and 1-bromo-2-butanone (0.22 g, 1.47 mmol) in EtOH (10 mL) was heated to reflux for 3 h. The solvent was removed under reduced pressure; the resulting yellow solid was dissolved in MeOH/CHCl$_3$, and dried onto silica gel. The slurry was then purified by column chromatography on silica gel using 1-4% MeOH/CHCl$_3$ as eluent, to afford 1-ethyl-3-[5-(4-ethyl-thiazol-2-yl)-7-pyridin-3-yl-[1,2,4]triazolo[1,5-a]pyridin-2-yl]-urea as a solid. LCMS (APCI$^+$) 394.

Example 123

1-Ethyl-3-[5-(2-ethyl-thiazol-5-yl)-7-pyridin-3-yl-[1,2,4]triazolo[1,5-a]pyridin-2-yl]-urea Step 1:

Nitrogen gas was purged through a suspension of 5-chloro-7-pyridin-3-yl-[1,2,4]triazolo[1,5-a]pyridin-2-ylamine which may be produced as described in Example 1A, (212 mg, 0.86 mmol), potassium acetate (422 mg, 4.30 mmol) and 2-ethyl-thiazole (674 μL mg, 6.02 mmol) in dry DMA (5 mL) for 3 min. Tetrakis(triphenylphosphine)palladium (50 mg, 0.04 mmol) was added, and the mixture was heated at 200° C. in a microwave reactor for 10 min. After being cooled to room temperature, the reaction mixture was diluted with EtOAc (150 mL), washed with water (3×25 mL), and the aqueous layer was back extracted with EtOAc. Combined organic extracts were washed with brine (25 mL×2), dried (Na$_2$SO$_4$), and concentrated in vacuo. The crude product was purified by silica gel chromatography (gradient 0-2% methanol/chloroform) to give 5-(2-ethyl-thiazol-5-yl)-7pyridin-3-yl-[1,2,4]triazolo[1,5-a]pyridin-2-ylamine as a solid. MS m/z 394 (M+H$^+$).

Step 2:

A suspension of the product of Step 1 (75 mg, 0.23 mmol), ethylisocyanate (92 μL, 1.17 mmol), and dibutyltin diacetate (2 drops) in dry toluene (5 mL) was heated at 125° C. in a microwave reactor for 1 h. After being cooled to room temperature, the precipitated solid was filtered, and washed with chloroform to give 1-ethyl-3-[5-(2-ethyl-thiazol-5-yl)-7-pyridin-3-yl-[1,2,4]triazolo[1,5-a]pyridin-2-yl]-urea as solid. MS m/z 394 (M+H$^+$).

Example 124

1-ethyl-3-[5-(2-ethyl-thiazol-5-yl)-7-pyridin-3-yl-[1,2,4]triazolo[1,5-a]pyridin-2-yl]-urea Step 1:
Nitrogen gas was purged through a suspension of 5-chloro-7-pyridin-3-yl-[1,2,4]triazolo[1,5-a]pyridin-2-ylamine, which may be produced as in Example 1A, (212 mg, 0.86 mmol), KOAc (422 mg, 4.30 mmol) and 2-ethyl-thiazole (674 µL mg, 6.02 mmol) in dry DMA (5 mL) for 3 min.
Tetrakis(triphenylphosphine)palladium (50 mg, 0.04 mmol) was added, and the mixture was heated at 200° C. in a microwave reactor for 10 min. After being cooled to room temperature, the reaction mixture was diluted with EtOAc (150 mL), washed with water (25 mL×3), and the aqueous layer was back extracted with EtOAc. Combined organic extracts were washed with brine (25 mL×2), dried (Na$_2$SO$_4$), and concentrated in vacuo. The crude product was purified by silica gel chromatography (gradient 0-2% methanol/chloroform) to give 5-(2-ethyl-thiazol-5-yl)-7-pyridin-3-yl-[1,2,4]triazolo[1,5-a]pyridin-2-ylamine as a solid. MS m/z 394 (M+H$^+$).

Step 2:
A suspension of the product of Step 1 (75 mg, 0.23 mmol), ethylisocyanate (92 µL, 1.17 mmol), and dibutyltin diacetate (2 drops) in dry toluene (5 mL) was heated at 125° C. in a microwave reactor for 1 h. After being cooled at room temperature, the precipitated solid was filtered, and washed with chloroform to give the title compound as a solid. MS m/z 394 (M+H$^+$).

Example 125

1-Ethyl-3-[5-(thiazol-5-yl)-7-pyridin-3-yl-[1,2,4]triazolo[1,5-a]pyridin-2-yl]-urea Step 1:
Using the general procedure of Example 124, Step 1, but substituting thiazole for 2-ethyl-thiazole, 5-(thiazol-5-yl)-7-pyridin-3-yl-[1,2,4]triazolo[1,5-a]pyridin-2-ylamine was produced as a solid. MS m/z 295 (M+H$^+$).

Step 2:
Using the general procedure of Example 124, Step 2, but substituting 5-(thiazol-5-yl)-7-pyridin-3-yl-[1,2,4]triazolo[1,5-a]pyridin-2-ylamine for 5-(2-ethyl-thiazol-5-yl)-7-pyridin-3-yl-[1,2,4]triazolo[1,5-a]pyridin-2-ylamine the title compound was obtained as a solid. MS m/z 366 (M+H$^+$).

Example 126

1-(5,7-Di-pyridin-3-yl-[2,4]triazolo[1,5-a]pyridin-2-yl)-3-ethyl-urea

Step 1:
A mixture of 3-pyridine boronic acid pinacolate ester (500 mg, 2.44 mmol), Na$_2$CO$_3$ (649 mg, 6.12 mmol) and 5-chloro-7-pyridin-3-yl-[1,2,4]triazolo[1,5-a]pyridin-2-ylamine, which may be produced as in Example 1A, (500 mg, 2.04 mmol) in toluene (30 mL), ethanol (15 mL) and water (15 mL) was degassed by purging with N$_2$ for 10 min. [PdCl$_2$(dppf)].CH$_2$Cl$_2$ (56 mg, 0.082 mmol) was added and the mixture was brought to reflux for 36 h. The solvent was evaporated and the residue was extracted into hot EtOH/MeOH, filtered through Celite, and pre-adsorbed onto SiO$_2$. Column chromatography (0-10% MeOH in CH$_2$Cl$_2$) afforded the product 5,7-di-pyridin-3-yl-[1,2,4]triazolo[1,5-a]pyridin-2-ylamine as a solid. MS m/z 289 (M+H$^+$).

Step 2:
A suspension of the product of Step 1 (185 mg, 0.642 mmol) in DMF (10 mL) was heated until almost homogeneous. TosNCO (0.20 mL, 1.3 mmol) was added all at once. The resulting solution was stirred for 1 h at room temperature whereon EtNH$_2$ (6.4 mL of a 2 M solution in THF) was added. The suspension was heated at 120° C. for 10 min in the microwave. On cooling, a precipitate was collected by filtration, washed with MeOH and dried in vacuo at 80° C. for 2 h to yield the title compound. MS m/z 360 (M+H$^+$).

Example 127

1-Ethyl-3-(5-pyridin-2-yl-7-pyridin-3-yl-[1,2,4]triazolo[1,5-a]pyridin-2-yl)-urea Step 1:
A suspension of 2-pyridineboronic acid N-phenyldiethanolamine ester (983 mg, 3.67 mmol), 5-chloro-7-pyridin-3-yl-[1,2,4]triazolo[1,5-a]pyridin-2-ylamine, which may be produced as in Example 1A, (450 mg, 1.83 mmol), K$_2$CO$_3$ (506 mg, 3.67 mmol), CuI (140 mg, 0.74 mmol) and [Pd(PPh$_3$)$_4$] (106 mg, 0.092 mmol) in dioxane (9 mL) was heated under microwave conditions at 150° C. for 30 min then at 160° C. for a further 30 min. The resulting suspension was dissolved in MeOH and pre-adsorbed onto SiO$_2$. Column chromatography (0-10% MeOH in CH$_2$Cl$_2$) afforded the product 5-pyridin-2-yl-7-pyridin-3-yl-[1,2,4]triazolo[1,5-a]pyridin-2-ylamine as a solid. MS m/z 289 (M+H$^+$).

Step 2:
Using the general procedure of Example 126, Step 2, but substituting 5-pyridin-2-yl-7-pyridin-3-yl-[1,2,4]triazolo[1,5-a]pyridin-2-ylamine for 5,7-dipyridin-3-yl-[1,2,4]triazolo[1,5-a]pyridin-2-ylamine, the title compound was obtained.

Example 128

1-Ethyl-3-(7-pyridin-3-yl-5-pyrimidin-2-yl-[1,2,4]triazolo[1,5-a]pyridin-2-yl)-urea Step 1:
A suspension of 2-tributylstannyl pyrimidine (1 g, 2.7 mmol), 5-chloro-7-pyridin-3-yl-[1,2,4]triazolo[1,5-a]pyridin-2-ylamine, which may be produced as in Example 1A, (605 mg, 2.46 mmol) and [PdCl$_2$(PPh$_3$)$_2$] (86 mg, 0.123 mmol) in dioxane (10 mL) was heated under reflux for 18 h, then at 150° C. under microwave conditions for 1 h. The resulting suspension was dissolved in hot MeOH and pre-adsorbed onto SiO$_2$. Column chromatography (0-10% MeOH in CH$_2$Cl$_2$) afforded 7-pyridin-3-yl-5-pyrimidin-2-yl-[1,2,4]triazolo[1,5-a]pyridin-2-ylamine as a solid. MS m/z 290 (M+H$^+$).

Step 2:
A warmed suspension of the product of Step 1 (330 mg, 1.14 mmol) in DMF (10 mL) was treated with TosNCO (0.43 mL, 2.9 mmol). The mixture was stirred at room temperature for 1 h. EtNH₂ (14 mL of a 2 M solution in THF) was added all at once and the suspension was heated in the microwave at 100° C. for 12 min. On cooling to 0° C. for 1 h, the precipitated solid 1-ethyl-3-(7-pyridin-3-yl-5-pyrimidin-2-yl-[1,2,4]triazolo[1,5-a]pyridin-2-yl)-urea was collected by filtration, washed with MeOH and dried in vacuo at 80° C. for 2 h. MS m/z 361 (M+H⁺).

Example 129

N-Ethyl-N'-[5-(2-methyl-1,3-oxazol-5-yl)-7-pyridin-3-yl[1,2,4]triazolo[1,5-a]pyridin-2-yl]urea Step 1:
A mixture of 2-methyl oxazole (Heterocycles, 1999, 53, 1167) (0.7 g, 6.6 mmol), 5-chloro-7-pyridin-3-yl-[1,2,4]triazolo[1,5-a]pyridin-2-ylamine, which may be produced as in Example 1A, (0.42 g, 1.32 mmol), Pd (PPh₃)₄ (84 mg, 5 mol %), and KOAc (0.84 g, 6.6 mmol) in DMA (6 mL) in a tube was irradiated with microwaves at 200° C. for 15 min. The reaction mixture was then filtered through a pad of Celite, washed repeatedly with MeOH and CHCl₃. The filtrate was evaporated and the resulting residue was triturated with CHCl₃. The filtrate was evaporated and the resulting residue was triturated with 15 mL of chloroform and 200 mL of hexanes. This crude product was taken up into MeOH/CHCl₃ and dried onto silica gel. This material was then purified by column chromatography on silica gel (10-15% MeOH/CHCl₃ as eluant) to afford 5-(2-Methyl-oxazol-5-yl)-7-pyridin-3-yl-[1,2,4]triazolo[1,5-a]pyridin-2-ylamine as a solid. LCMS (APCI⁺) 293.

Step 2:
A mixture of the product of Step 1 (0.23 g, 0.787 mmol), ethyl isocyanate (0.28 g, 3.93 mmol) and a catalytic quantity of dibutyltin diacetate (3 drops) in THF/toluene (1:1, 10 mL) was heated in a sealed tube at 100° C. for 15 h. This mixture was cooled to 0° C., the solid obtained was filtered and washed with 10% CHCl₃/hexanes to provide the target compound, N-ethyl-N'-[5-(2-methyl-1,3-oxazol-5-yl)-7-pyridin-3-yl[1,2,4]triazolo[1,5-a]pyridin-2-yl]urea as a solid. LCMS (APCI⁺) 364.

Example 130

1-[5-(3-Dimethylamino-pyrrolidin-1-yl)-7-pyridin-3-yl-[1,2,4]triazolo[1,5-a]pyridin-2-yl]-3-ethyl-urea Step 1:
A mixture of 5-chloro-7-pyridin-3-yl-[1,2,4]triazolo[1,5-a]pyridin-2-ylamine, which may be produced as in Example 1A, (0.3 g, 1.22 mmol), and dimethyl-pyrrolidin-3-yl-amine (0.3 ml, 2.4 mmol) in anhydrous toluene (5 ml) was irradiated with microwaves at 130° C. for 60 minutes. Additional dimethyl-pyrrolidin-3-yl-amine (0.15 ml, 1.2 mmol) was added and the resulting mixture was irradiated for 60 minutes at 130° C. The solvent was evaporated and this material was purified by silica gel column chromatography (0-1% NH₄OH, 0-10% MeOH in CH₂Cl₂ as eluant) to afford 5-(3-dimethylamino-pyrrolidin-1-yl)-7-pyridin-3-yl-[1,2,4]triazolo[1,5-a]pyridin-2-ylamine, as a solid. MS (APCI⁺) 324 (M+1).

Step 2:
A mixture of 5-(3-dimethylamino-pyrrolidin-1-yl)-7-pyridin-3-yl-[1,2,4]triazolo[1,5-a]pyridin-2-ylamine (0.190 g, 0.6 mmol), and NaHMDS (1.4 ml of 1 M solution in THF, 1.4 mmol) in anhydrous THF (100 ml) was stirred at room temperature for 45 minutes. EtNCO (0.5 ml, 6.3 mmol) was added and the resulting reaction mixture was stirred at room temperature overnight. The reaction was quenched with HCl (0.35 ml of 4 M solution in dioxane). Solvent was evaporated and the resultant material was purified by column chromatography on silica gel (1% NEt₃, 0-10% MeOH in CH₂Cl₂ as eluant), followed by trituration in EtOH, to afford the desired compound as a solid. Mp. 248-250° C. MS (APCI⁺) 395 (M+1).

Example 131

1-Ethyl-3-[5-(4-methyl-piperazin-1-yl)-7-pyridin-3-yl-[1,2,4]triazolo[1,5-a]pyridin-2-yl]-urea Step 1:
A mixture of 5-chloro-7-pyridin-3-yl-[1,2,4]triazolo[1,5-a]pyridin-2-ylamine, which may be produced as in Example 1A, (0.5 g, 2.03 mmol), and 1-methyl-piperazine (6 ml, 54 mmol) was irradiated with microwaves at 130° C. for 60 minutes. Solvent was evaporated. The resulting material was purified by column chromatography on silica gel (0-2% NH₄OH, 0-10% MeOH in CH₂Cl₂ as eluant) to afford 5-(4-methyl-piperazin-1-yl)-7-pyridin-3-yl-[1,2,4]triazolo[1,5-a]pyridin-2-ylamine as a solid. MS (APCI⁺) 310 (M+1).

Step 2:
Using the generalized procedure of Example 130, Step 2, but substituting 5-(4-methyl-piperazin-1-yl)-7-pyridin-3-yl-[1,2,4]triazolo[1,5-a]pyridin-2-ylamine for 5-(3-dimethylamino-pyrrolidin-1-yl)-7-pyridin-3-yl-[1,2,4]triazolo[1,5-a]pyridin-2-ylamine, the title compound was obtained. The compound was purified by column chromatography on silica gel (1% NEt₃, 0-10% MeOH in CH₂Cl₂ as eluant), followed by trituration in EtOH, to afford the desired compound as a solid MS (APCI⁺) 381 (M+1).

Example 132

1-Ethyl-3-[5-(2-methyl-thiazol-5-yl)-7-pyridin-3-yl-[1,2,4]triazolo[1,5-a]pyridin-2-yl]-urea Step 1:
Nitrogen gas was purged through a suspension of 5-chloro-7-pyridin-3-yl-[1,2,4]triazolo[1,5-a]pyridin-2-ylamine, which may be produced as in Example 1A, (246 mg, 1.0 mmol), KOAc (490 mg, 5.0 mmol) and 2-methylthiazole (623 μL mg, 7.0 mmol) in dry DMA (5 mL) for 3 min. Tetrakis (triphenylphosphine)palladium (58 mg, 0.05 mmol) was added, and the mixture was heated at 200° C. in a microwave reactor for 10 min. After being cooled to room temperature the mixture was diluted with EtOAc (100 mL), washed with water (10 mL×3), and the aqueous layer was back extracted with EtOAc (50 mL). Combined organic extracts were washed with brine (10 mL×2), dried (Na₂SO₄), and concentrated. The solid obtained was triturated with chloroform to give 5-(2-methyl-thiazol-5-yl)-7pyridin-3-yl-[1,2,4]triazolo[1,5-a]pyridin-2-ylamine as a solid. MS m/z 309 (M+H⁺).

Step 2:
A suspension of the product of Step 1 (160 mg, 0.52 mmol), ethylisocyanate (205 μL, 2.6 mmol), and dibutyltin diacetate (5 drops) in dry toluene (6 mL) was heated at 125° C. in a microwave reactor for 1 h. After being cooled at room temperature the precipitated solid was filtered and washed with chloroform. The crude product was purified by flash chromatography (gradient 0-2% methanol/chloroform) to give 1-ethyl-3-[5-(2-methyl-thiazol-5-yl)-7-pyridin-3-yl-[1,2,4]triazolo[1,5-a]pyridin-2-yl]-urea as a solid. MS m/z 380 (M+H$^+$).

Example 133

1-Ethyl-3-(5-morpholin-4-yl-7-pyridin-3-yl-[1,2,4]triazolo[1,5-a]pyridin-2-yl)-urea Step 1:

A mixture of 5-chloro-7-pyridin-3-yl-[1,2,4]triazolo[1,5-a]pyridin-2-ylamine, which may be produced as in Example 1A, (0.5 g, 2.03 mmol), and morpholine (6 ml, 69 mmol) was irradiated with microwaves at 130° C. for 60 minutes. Morpholine was removed in vacuo and the resulting material was purified by column chromatography on silica gel (0-2% NH$_4$OH, 0-10% MeOH in CH$_2$Cl$_2$ as eluant) to afford 5-morpholin-4-yl-7-pyridin-3-yl-[1,2,4]triazolo[1,5-a]pyridin-2-ylamine as a solid. MS (APCI$^+$) 297 (M+1).

Step 2:

Using the generalized procedure of Example 130, Step 2, but substituting 5-morpholin-4-yl-7-pyridin-3-yl-[1,2,4]triazolo[1,5-a]pyridin-2-ylamine for 5-(3-dimethylamino-pyrrolidin-1-yl)-7-pyridin-3-yl-[1,2,4]triazolo[1,5-a]pyridin-2-ylamine, 1-ethyl-3-(5-morpholin-4-yl-7-pyridin-3-yl-[1,2,4]triazolo[1,5-a]pyridin-2-yl)-urea was obtained as a solid. Melting Point: 298-300° C. MS (APCI$^+$) 368 (M+1).

Example 134

1-Ethyl-3-[5-(3-hydroxy-pyrrolidin-1-yl)-7-pyridin-3-yl-[1,2,4]triazolo[1,5-a]pyridin-2-yl]-urea Step 1:

A mixture of 5-chloro-7-pyridin-3-yl-[1,2,4]triazolo[1,5-a]pyridin-2-ylamine, which may be produced as in Example 1A, (0.5 g, 2.03 mmol), and pyrrolidin-3-ol (2 ml, 24 mmol) in anhydrous toluene (4 ml) was irradiated with microwaves at 130° C. for 60 minutes. The reaction mixture was filtered. The solid was washed with methanol to afford the desired product, 1-(2-amino-7-pyridin-3-yl-[1,2,4]triazolo[1,5-a]pyridin-5-yl)-pyrrolidin-3-ol as a solid. MS (APCI$^+$) 297 (M+1).

Step 2:

The product of Step 1 (0.53 g, 1.65 mmol) was split into three batches. Each batch was suspended in anhydrous DMF and TsNCO (0.25 ml, 1.65 mmol) was added. A clear yellow solution was obtained which was stirred at room temperature overnight. EtNH$_2$ (3 ml of a 2 M solution in THF, 6 mmol) was added and the resulting mixture was irradiated with microwaves at 140° C. for 30 minutes. The three batches were combined, filtered and washed with THF. This material was triturated in EtOH, to afford 1-ethyl-3-[5-(3-hydroxy-pyrrolidin-1-yl)-7-pyridin-3-yl-[1,2,4]triazolo[1,5-a]pyridin-2-yl]-urea as a solid. mp 296-298° C. MS (APCI$^+$) 368 (M+1).

Example 135

N-[5-(1,2-Dimethyl-1H-imidazol-5-yl)-7-pyridin-3-yl[1,2,4]triazolo[1,5-a]pyridin-2-yl]-N'-ethylurea Step 1:

A mixture of 5-chloro-7-pyridin-3-yl-[1,2,4]triazolo[1,5-a]pyridin-2-ylamine, which may be produced by the method of Example 1A, (0.40 g, 1.63 mmol), 1,2-dimethyl-1H-imidazole (0.78 g, 8.15 mmol), Pd (PPh$_3$)$_4$ (80 mg, 5 mol %), and KOAc (0.80 g, 8.15 mmol) in DMA (5 mL) in a tube was irradiated with microwaves at 200° C. for 15 min. The reaction mixture was then filtered through a pad of Celite, washed repeatedly with MeOH and CHCl$_3$. The filtrate was evaporated and the resulting residue was triturated with CHCl$_3$ (100 mL). The filtrate was evaporated and the resulting residue was triturated with 50 mL of chloroform and 500 mL of hexanes, the solid obtained was filtered, washed with hexanes and dried. This crude product was taken up into MeOH/CHCl$_3$, and dried onto silica gel. This material was then purified by column chromatography on silica gel (2-10% MeOH/CHCl$_3$ as eluant) to afford 5-(2,3-dimethyl-3H-imidazol-4-yl)-7-pyridin-3-yl-[1,2,4]triazolo[1,5-a]pyridin-2-ylamine as a solid. LCMS (APCI$^+$) 306.

Step 2:

A mixture of the product of Step 1 (0.37 g, 1.21 mmol), ethylisocyanate (0.43 g, 6.05 mmol) and a catalytic quantity of dibutyltin diacetate (5 drops) in THF/toluene (1:1, 10 mL) was heated in a sealed tube at 100° C. for 15 h. This mixture was cooled to 0° C., the solid obtained was filtered and washed with 10% CHCl$_3$/hexanes to isolate crude product. The solid was taken up into MeOH/CHCl$_3$, and dried onto silica gel. This material was then purified by column chromatography on silica gel (1-8% MeOH/CHCl$_3$ as eluant) followed by trituration with chloroform (10 mL) and hexanes (500 mL) to isolate the title compound as a solid. LCMS (APCI$^+$) 377.

Example 136

N-ethyl-N'-[5-(1-methyl-1H-imidazol-5-yl]-7-pyridin-3-yl[1,2,4]triazolo[1,5-a]pyridin-2-yl]urea Step 1:

Using the general procedure of Example 135, Step 1, but substituting 1-methyl-1H-imidazole for 1,2-dimethyl-1H-imidazole, 5-(3-methyl-3H-imidazol-4-yl)-7-pyridin-3-yl-[1,2,4]triazolo[1,5-a]pyridin-2-ylamine was obtained. The resulting filtrate was evaporated and the resulting residue was triturated with 300 mL of CHCl$_3$. The solid obtained was filtered, washed with CHCl$_3$ and discarded. The filtrate was evaporated and the resulting residue was triturated with 50 mL of chloroform and 400 mL of hexanes, the solid obtained was filtered, washed with hexanes and dried. This crude product was taken up into MeOH/CHCl3, and dried onto silica gel. This material was then purified by column chromatography on silica gel (2-10% MeOH/CHCl3 as eluant) to afford 5-(3-Methyl-3H-imidazol-4-yl)-7-pyridin-3-yl-[1,2,4]triazolo[1,5-a]pyridin-2-ylamine as a solid. LCMS (APCI$^+$) 292.

Step 2:

Using the general procedure of Example 135, Step 2, but substituting the product of Step 1 produced immediately above, the title compound was obtained as a solid. LCMS (APCI$^+$) 363.

Example 137

N-[5-[Cyclohexyl(methyl)amino]-7-pyridin-3-yl[1,2,4]triazolo[1,5-a]pyridin-2-yl]-N'-ethylurea Step 1:

A mixture of N-methyl-cyclohexylamine (4 mL) and 5-chloro-7-pyridin-3-yl-[1,2,4]triazolo[1,5-a]pyridin-2-ylamine, which may be produced as in Example 1A, (300 mg, 1.22 mmol) was microwaved at 200° C. for 3 h. On cooling, the product was triturated with toluene/cyclohexane then taken up in $CH_2Cl_2$ and washed with aqueous $Na_2CO_3$. The organic layer was separated, dried ($MgSO_4$), and concentrated to produce $N^5$-cyclohexyl-$N^5$-methyl-7-pyridin-3-yl-[1,2,4]triazolo[1,5-a]pyridine-2,5-diamine. MS m/z 323 (M+H$^+$).

Step 2:

The product of Step 1 (290 mg, 0.90 mmol) was taken up in DMF (1 mL). TosNCO (0.44 g, 2.3 mmol) was added all at once. The solution became warm and was allowed to cool to room temperature over 1 h. Ethylamine (6 mL of a 2 M solution in THF) was added and the resulting mixture was microwaved at 100° C. for 10 min then at 120° C. for 30 min. The resulting solid was collected by filtration and triturated with $CH_2Cl_2$/MeOH to afford 1-[5-(cyclohexyl-methyl-amino)-7-pyridin-3-yl-[1,2,4]triazolo[1,5-a]pyridin-2-yl]-3-ethyl-urea. MS m/z 394 (M+H$^+$).

Example 138

1-(5-Cyclohexylamino-7-pyridin-3-yl-[1,2,4]triazolo[1,5-a]pyridin-2-yl)-3-ethyl-urea Step 1:

A mixture of cyclohexylamine (4 mL) and 5-chloro-7-pyridin-3-yl-[1,2,4]triazolo[1,5-a]pyridin-2-ylamine, which may be produced as in Example 1A, (280 mg, 1.14 mmol) was microwaved at 155° C. for 1 h. On cooling, the product was triturated with toluene/cyclohexane, then taken up in $CH_2Cl_2$ and washed with aqueous $Na_2CO_3$. The organic layer was separated, dried ($MgSO_4$), then concentrated to provide $N^5$-cyclohexyl-7-(pyridin-3-yl)-[1,2,4]triazolo[1,5-a]pyridine-2,5-diamine. MS m/z 309 (M+H$^+$).

Step 2:

The product of Step 1 (256 mg, 0.83 mmol) was taken up in DMF (2 mL) and cooled on an ice/water bath. TosNCO (0.18 g, 0.91 mmol) was added all at once. The solution was allowed to stir at room temperature for 1.5 h. Ethylamine (3 mL of a 2 M solution in THF) was added and the resulting solution was microwaved at 120° C. for 10 min. The solution was cooled in the refrigerator overnight and the resulting precipitate was collected by filtration yielding 1-(5-cyclohexylamino-7-pyridin-3-yl-[1,2,4]triazolo[1,5-a]pyridin-2-yl)-3-ethyl-urea. MS m/z 380 (M+H$^+$).

Example 139

N-Ethyl-N'-[5-(2-ethyl-1,3-oxazol-5-yl)-7-pyridin-3-yl[1,2,4]triazolo[1,5-a]pyridin-2-yl]urea Step 1:

Using the general procedure of Example 129, Step 2, but substituting 2-ethyl-isoxazole (Tetrahedron Letters 1983, 24, 4391) for 2-methyl-oxazole, 5-(2-Ethyl-oxazol-5-yl)-7-pyridin-3-yl-[1,2,4]triazolo[1,5-a]pyridin-2-ylamineis obtained as a solid. LCMS (APCI$^+$) 307.

Step 2:

Using the general procedure of Example 143, Step 3, but substituting the product of Step 1 produced immediately above as the relevant starting material, the title compound was obtained which was purified by flash chromatography using 2-8% MeOH/CHCl$_3$ as eluant to isolate a solid. LCMS (APCI$^+$) 378.

Example 140

1-Ethyl-3-[5-(2-i-propyl-thiazol-5-yl)-7-pyridin-3-yl-[1,2,4]triazolo[1,5-a]pyridin-2-yl]-urea Step 1:

Using the general procedure of Example 124, Step 1, but substituting 2-isopropyl-thiazole for 2-ethyl-thiazole, 5-(2-isopropyl-thiazol-5-yl)-7pyridin-3-yl-[1,2,4]triazolo[1,5-a]pyridin-2-ylamine was produced as a solid. MS m/z 337 (M+H$^+$).

Step 2:

Using the general procedure of Example 124, Step 2, but substituting 5-(2-isopropyl-thiazol-5-yl)-7-pyridin-3-yl-[1,2,4]triazolo[1,5-a]pyridin-2-ylamine for 5-(2-ethyl-thiazol-5-yl)-7-pyridin-3-yl-[1,2,4]triazolo[1,5-a]pyridin-2-ylamine, the title compound was obtained. The reaction mixture was concentrated and was purified by flash chromatography (gradient of 0-2% MeOH in chloroform) to give a solid. MS m/z 408 (M+H$^+$).

Example 141

1-[5-(2-Dimethylamino-ethoxy)-7-pyridin-3-yl-[1,2,4]triazolo[1,5-a]pyridin-2-yl]-3-ethyl-urea Step 1:

Butyllithium (1.2 ml of a 2.5 M solution in hexanes, 3 mmol) was added dropwise to a solution of 2-dimethylaminoethanol (0.4 ml, 4 mmol) in THF (4 mL). After 5 minutes 5-chloro-7-pyridin-3-yl-[1,2,4]triazolo[1,5-a]pyridin-2-ylamine, which may be produced as described in Example 1A, (0.3 g, 1.22 mmol) was added and the resulting mixture was irradiated with microwaves at 120° C. for 1 h. The product was filtered and washed with THF. The desired product, 5-(2-dimethylamino-ethoxy)-7-pyridin-3-yl-[1,2,4]triazolo[1,5-a]pyridin-2-ylamine was used directly in the next step. MS (APCI$^+$) 299 (M+1).

Step 2:

Using the generalized procedure of Example 130, Step 2, but substituting 5-(2-dimethylamino-ethoxy)-7-pyridin-3-yl-[1,2,4]triazolo[1,5-a]pyridin-2-ylamine for 5-(3-dimethylamino-pyrrolidin-1-yl)-7-pyridin-3-yl-[1,2,4]triazolo[1,5-a]pyridin-2-ylamine, the title compound was obtained as a solid. mp 200-202° C. MS (APCI$^+$) 370 (M+1).

Example 142

N-Ethyl-N'-[5-(6-methoxypyridin-3-yl)-7-pyridin-3-yl[1,2,4]triazolo[1,5-a]pyridin-2-yl]urea Step 1:

A suspension of 5-chloro-7-pyridin-3-yl-[1,2,4]triazolo[1,5-a]pyridin-2-ylamine, which may be produced as in Example 1A (210 mg, 0.86 mmol), ethylisocyanate (600 mg, 8.6 mmol), and dibutyltin diacetate (2 drops) in a mixture of toluene and THF (1:1, 10 mL) was heated at 110° C. with stirring in a sealed tube for 5 h. The homogeneous reaction mixture was cooled to RT. The solvent was removed under reduced pressure and the resulting solid was triturated with chloroform (10 mL) and hexanes (250 mL). The solid was filtered, washed with hexanes, and dried to obtain 1-(5-Chloro-7-pyridin-3-yl-[1,2,4]triazolo[1,5-a]pyridin-2-yl)-3-ethyl-urea LCMS (APCI+) 317.

Step 2:

To a mixture of 1-(5-chloro-7-pyridin-3-yl-[1,2,4]triazolo[1,5-a]pyridin-2-yl)-3-ethyl-urea (0.2 g, 0.63 mmol) obtained in step 1, 6-Methoxy-pyridine-3-boronic acid (0.12 g, 0.78 mmol), and sodium carbonate (0.71 mL of a 2 M aqueous solution) in dioxane (6 mL) was added the catalyst Pd(dppf)Cl$_2$ (30 mg, 5 mol %) and the resulting mixture was heated to reflux for 36 hours. The solvent was removed under reduced pressure. Purification using silica gel chromatography (2-10% MeOH/CHCl$_3$) gave the title compound as a solid LCMS (APC$^+$) 390.

Example 143

N-Ethyl-N'-[7-pyridin-3-yl-5-(2-pyrrolidin-1-ylethoxy)[1,2,4]triazolo[1,5-a]pyridin-2-yl]urea Butyllithium (0.8 ml of a 2.5 M solution in hexanes, 2 mmol) was added dropwise to a solution of 2-pyrrolidin-1-yl-ethanol (0.3 ml, 2.6 mmol) in THF (5 mL). After 5 minutes, 1-(5-chloro-7-pyridin-3-yl-[1,2,4]triazolo[1,5-a]pyridin-2-yl)-3-ethyl-urea, which may be produced as described in Example 142, step 1, (0.16 g, 0.5 mmol) was added and the resulting mixture was stirred at room temperature overnight. It was then irradiated with microwaves at 100° C. for 15 minutes. The reaction mixture was quenched with HCl (0.5 ml of a 4 M solution in dioxane). Solvent was evaporated and the resulting residue was purified by column chromatography on silica gel (1% NEt$_3$, 0-10% MeOH in CH$_2$Cl$_2$ as eluant), followed by trituration in EtOH, to afford the desired compound as a solid. mp 189-192° C. (dec.). MS (APCI$^+$) 396 (M+1).

Example 144

1-Ethyl-3-[5-(2-piperidin-1-yl-ethoxy)-7-pyridin-3-yl-[1,2,4]triazolo[1,5-a]pyridin-2-yl]-urea Using the general procedure of Example 144 but substituting 2-piperidin-1-yl-ethanol for 2-pyrrolidin-1-yl-ethanol, the target compound was obtained as a white solid. MS (APCI$^+$) 410 (M+1).

Example 145

N-Methyl-N'-[5-(3-methylpyridin-2-yl)-7-pyridin-3-yl[1,2,4]triazolo[1,5-a]pyridin-2-yl]urea Step 1:

2-(3-Methyl-pyridin-2-yl)-6-phenyl-[1,3,6,2]dioxazaborocane (2.76 g, 9.8 mmol), 5-chloro-7-pyridin-3-yl-[1,2,4]triazolo[1,5-a]pyridin-2-ylamine, which may be produced as described in Example 1, (0.60 g, 2.44 mmol), K$_2$CO$_3$ (0.67 g, 4.9 mmol), CuI (186 mg, 0.98 mmol) and [Pd(PPh$_3$)$_4$] (141 mg, 0.12 mmol) were taken up in dry dioxane (20 mL). The resulting mixture was subjected to microwave radiation at full power (300 W) over 4 h. The temperature attained during this time varied between 150-170° C. On cooling, methanol was added and the suspension was filtered through a Celite pad. SiO$_2$ was added to the filtrate and the solvent was removed by rotary evaporation. Column chromatography (0-10% MeOH/DCM) afforded 5-(3-methyl-pyridin-2-yl)-7-pyridin-3-yl-[1,2,4]triazolo[1,5-a]pyridin-2-ylamine.

Step 2:

The product of Step 1 (240 mg, 0.79 mmol) was taken up in DMF (2 mL) to which was added TosNCO (0.31 g, 1.6 mmol) all at once. The mixture was stirred at room temperature for 1 h whereon a 2 M solution of H$_2$NEt (3 mL, 6 mmol) in THF was added. The homogeneous solution was microwaved at 100° C. for 10 min. On cooling, SiO$_2$ was added and the solvent was removed. Column chromatography afforded the title compound. MS m/z 374 (M+H$^+$).

Example 146

1-Ethyl-3-(5-piperazin-1-yl-7-pyridin-3-yl-[1,2,4]triazolo[1,5-a]pyridin-2-yl)-urea Step 1:

A mixture of 5-chloro-7-pyridin-3-yl-[1,2,4]triazolo[1,5-a]pyridin-2-ylamine, which may be produced as in Example 1A, (0.49 g, 2.0 mmol), and piperazine-1-carboxylic acid tert-butyl ester (2 g, 10.7 mmol) was irradiated with microwaves at 130° C. for 60 minutes. The reaction mixture was purified by column chromatography on silica gel (0-10% MeOH in CH$_2$Cl$_2$ as eluant) to afford 4-(2-amino-7-pyridin-3-yl-[1,2,4]triazolo[1,5-a]pyridin-5-yl)-piperazine-1-carboxylic acid tert-butyl ester as a solid. This material was used directly in the next step. MS (APCI$^+$) 396 (M+1)

Step 2:

The material produced in Step 1 (0.78 g, 2.0 mmol) was split into three batches. Each batch was suspended in DMF (3 mL) and then TsNCO (0.3 ml, 2 mmol) was added. The reaction mixture was stirred at rt overnight. Ethylamine (3 ml of a 2 M solution in THF, 6 mmol) was added and the resulting mixture was irradiated with microwaves at 130° C. for 40 minutes. The three batches were combined, filtered, washed with THF, and dried to afford 4-[2-(3-ethyl-ureido)-7-pyridin-3-yl-[1,2,4]triazolo[1,5-a]pyridin-5-yl]-piperazine-1-carboxylic acid tert-butyl ester as a solid. MS (APCI$^+$) 467 (M+1).

Step 3:

The product of Step 2, 4-[2-(3-ethyl-ureido)-7-pyridin-3-yl-[1,2,4]triazolo[1,5-a]pyridin-5-yl]-piperazine-1-carboxylic acid tert-butyl ester (0.52 g, 1.1 mmol) was suspended in CH$_2$Cl$_2$ (10 mL) Trifluoroacetic acid (5 ml) was added and the resulting solution was stirred at rt for 30 minutes. The reaction mixture was diluted with toluene and solvent was evaporated. The residue was purified by column chromatography on silica gel (0-10% MeOH in CH$_2$Cl$_2$ containing 1% NEt$_3$ as eluant) to afford the target compound as a solid. MS (APCI$^+$) 366 (M+1).

Example 147

2-N-Methylsulfonylamino-7-pyridin-3-yl-[1,2,4]triazolo[1,5-a]pyridin-5-carboxylic acid ethyl amide Step 1:

Nitrogen gas was purged through a suspension of 2-amino-7-bromo-[1,2,4]triazolo[1,5-a]pyridine-5-carboxylic acid ethyl ester, which may be produced as in Example 6, (2.85 g, 10.0 mmol), NaOAc (4.10 g, 50.0 mmol), and pyridin-3-boronic acid (1.48 g, 12.0 mmol) in toluene:EtOH:water (2:1:1, 100 mL) for 5 min. Tetrakis(triphenylphosphine)palladium (0.23 g, 0.2 mmol) was added, and the mixture was refluxed for 7 h. The reaction mixture was concentrated, and was purified by silica gel chromatography (gradient of 0-2% MeOH in chloroform) to give 2-amino-7-pyridin-3-yl-[1,2,4]triazolo[1,5-a]pyridine-5-carboxylic acid ethyl ester as a solid. MS m/z 284 (M+H$^+$).

Step 2:

A suspension of the product of Step 1 (0.69 g, 2.45 mmol) in 2 M solution of ethylamine in THF (15 mL) was allowed to stir at room temperature for 2 days. The solid precipitate was filtered to give 2-amino-7-pyridin-3-yl-[1,2,4]triazolo[1,5-a]pyridine-5-carboxylic acid ethyl amide as a solid. MS m/z 283 (M+H$^+$).

Step 3:

N-methyl sulfamoyl chloride (116 mg, 0.90 mmol) was added dropwise to an ice cold suspension of the product of Step 2 (126 mg, 0.45 mmol), triethylamine (0.09 mL, 1.13 mmol) in a 1:1 mixture THF:CH$_2$Cl$_2$ (16 mL). The reaction mixture was stirred at room temperature overnight. The solid precipitate was filtered, washed with chloroform, and with water. The solid obtained was triturated with 1% MeOH in chloroform (6 mL) to give 2-N-methylsulfonylamino-7-pyridin-3-yl-[1,2,4]triazolo[1,5-a]pyridine-5-carboxylic acid ethyl amide as a solid. MS m/z 376 (M+H$^+$).

Example 148

N-[5-(2,4-Dimethyl-1,3-oxazol-5-yl)-7-pyridin-3-yl[1,2,4]triazolo[1,5-a]pyridin-2-yl]-N'-ethylurea Step 1:

A mixture of 2,4-dimethyloxazole (0.54 g, 5.56 mmol), 5-chloro-7-pyridin-3-yl-[1,2,4]triazolo[1,5-a]pyridin-2-ylamine, which may be produced as in Example 1A, (0.46 g, 1.86 mmol), Pd(PPh$_3$)$_4$ (84 mg, 5 mol %), and KOAc (0.54 g, 5.56 mmol) in DMA (6 mL) in a tube was irradiated with microwaves at 200° C. for 15 min. The reaction mixture was then filtered through a pad of Celite, washed with MeOH (4×10 mL) and then CHCl$_3$ (2×10 mL). The filtrate was evaporated and the resulting residue was triturated with CHCl$_3$ (600 mL). The solid obtained was filtered, washed with CHCl$_3$ and discarded. The combined filtrates were evaporated and the resulting residue was triturated with chloroform (20 mL) and hexanes (800 mL) to yield a solid that was filtered, washed with hexanes, and dried. This crude product was taken up into MeOH/CHCl$_3$ and dried onto silica gel. This material was then purified by column chromatography on silica gel (4-8% MeOH/CHCl$_3$ as eluant) to afford the desired product 5-(2,4-dimethyl-oxazol-5-yl)-7-pyridin-3-yl-[1,2,4]triazolo[1,5-a]pyridin-2-ylamine as a solid. LCMS (APCI$^+$) 307.

Step 2:

A mixture of the product of Step 1 (0.13 g, 0.42 mmol), ethyl isocyanate (0.15 g, 1.26 mmol) and a catalytic quantity of dibutyltin diacetate (3 drops) in THF/toluene (1:1, 10 mL) was heated in a sealed tube at 100° C. for 15 h. This mixture was cooled to 0° C., the solid obtained was filtered and washed with hexanes then was purified by column chromatography (gradient: 2-6% MeOH/CHCl$_3$) to give a solid. LCMS (APCI$^+$) 378.

Example 149

1-Ethyl-3-[7-(6-methoxy-pyridin-3-yl)-5-(2-methyl-oxazol-5-yl)-[1,2,4]triazolo[1,5-a]pyridin-2-yl]-urea Step 1:

A mixture of 5-Chloro-7-(6-methoxy-pyridin-3-yl)-[1,2,4]triazolo[1,5-a]pyridin-2-ylamine, which may be produced similar to Example 1A but substituting 6-methoxy-pyridine-3-boronic acid for 3-pyridine boronic acid (300 mg, 1.09 mmol), 2-methyl-oxazole (450 mg, 5.4 mmol), [Pd(PPh$_3$)$_4$] (130 mg, 0.11 mmol), KOAc (534 mg, 5.45 mmol) and DMA (4 mL) was microwaved at 200° C. for 15 min. The cooled mixture was taken up in MeOH/CHCl$_3$, filtered through Celite, and then the filtrate was pre-adsorbed on SiO$_2$. Column chromatography (3% MeOH/CHCl$_3$) gave a solid which was triturated with a 1:1 mixture of DCM/hexane. Filtration gave 7-(6-methoxy-pyridin-3-yl)-5-(2-methyl-oxazol-5-yl)-[1,2,4]triazolo[1,5-a]pyridin-2-ylamine.

Step 2:

A mixture of the product of Step 1 (0.14 g, 0.43 mmol), EtNCO (0.15 g, 2.2 mmol) and SnBu$_2$(OAc)$_2$ in dioxane (4 mL) was microwaved at 125° C. for 1 h. The resulting solid was collected by filtration and recrystallized from DMF to give the target compound. Pre-adsorption of a MeOH/CHCl$_3$ solution of this compound onto SiO$_2$ and column chromatography (5% MeOH/DCM) gave the title compound as a solid. MS m/z 394 (M+H$^+$).

Example 150

1-Ethyl-3-(5-[methyl-(1-methyl-pyrrolidin-3-yl)-amino]-7-pyridin-3-yl-[1,2,4]triazolo[1,5-a]pyridin-2-yl)-urea A solution of methyl-(1-methyl-pyrrolidin-3-yl)-amine (0.36 g, 3.2 mmol) in THF (4 mL) was treated rapidly with butyllithium (1 mL of a 2.5 M solution in hexanes, 2.5 mmol) at room temperature. After stirring for 1 h at room temperature, 1-(5-chloro-7-pyridin-3-yl-[1,2,4]triazolo[1,5-a]pyridin-2-yl)-3-ethyl-urea, which may be produced according to Example 142 (200 mg, 0.63 mmol) was added and the resulting mixture was microwaved at 100° C. for 20 min. After cooling, HCl (1.25 mL of a 2 M aqueous solution 2.5 mmol) and toluene (20 mL) were added. The solid precipitate was collected by filtration. Purification by silica gel column chromatography (5% NEt$_3$/5% MeOH/EtOAc), followed by trituration with EtOAc/hexane, and drying in vacuo gave the desired product as a solid.

Example 151

2-N-ethylsulfonylamino-7-pyridin-3-yl-[1,2,4]triazolo[1,5-a]pyridin-5-carboxylic acid ethyl amide Step 1:

Nitrogen gas was purged through a suspension of 2-amino-7-bromo-[1,2,4]triazolo[1,5-a]pyridine-5-carboxylic acid ethyl ester, which may be produced as in Example 6, (2.85 g, 10.0 mmol), NaOAc (4.10 g, 50.0 mmol), and pyridin-3-boronic acid (1.48 g, 12.0 mmol) in toluene:EtOH:water (2:1:1, 100 mL) for 5 min. Tetrakis(triphenylphosphine)palladium (0.23 g, 0.2 mmol) was added, and the mixture was refluxed for 7 h. The reaction mixture was concentrated, and was purified by silica gel chromatography (gradient 0-2% MeOH in chloroform) to give 2-amino-7-pyridin-3-yl-[1,2,4]triazolo[1,5-a]pyridin-5-carboxylic acid ethyl ester as a solid. MS m/z 284 (M+H$^+$).

Step 2:

The product of Step 1 (0.69 g, 2.45 mmol) and ethylamine (15 mL of a 2.0 M solution in THF) was allowed to stir at room temperature for 72 h. The solid was filtered to give 2-amino-7-pyridin-3-yl-[1,2,4]triazolo[1,5-a]pyridin-5-carboxylic acid ethyl amide) as a solid.

Step 3:

N-ethyl sulfamoyl chloride (141 mg) was added dropwise to an ice cold suspension of the product of step 2 (137 mg, 0.49 mmol) and triethylamine (99 µL, 1.23 mmol) in THF:CH$_2$Cl$_2$ (16 mL). The reaction mixture was stirred at room temperature for 18 h. The solid precipitate was filtered, washed with chloroform, and washed with water. The solid obtained was triturated with 1% MeOH in chloroform (6 mL) to give the title compound as a solid. MS m/z 376 (M+H$^+$).

Example 152

1-Ethyl-3-[5-(1-methyl-piperidin-4-ylamino)-7-pyridin-3-yl[1,2,4]triazolo[1,5-a]pyridin-2-yl]-urea Step 1:

A mixture of 5-chloro-7-pyridin-3-yl-[1,2,4]triazolo[1,5-a]pyridin-2-ylamine, which may be produced as in Example 1A, (400 mg, 1.6 mmol), 1-methyl-piperidin-4-ylamine (500 mg, 4.4 mmol) and K$_2$CO$_3$ (220 mg, 1.6 mmol) in dioxane (1 mL) was microwaved at 180° C. for 4 h. After removal of solvent, silica gel chromatography (5% NEt$_3$/10% MeOH/EtOAc) gave a solid N$^5$-(1-methyl-piperidin-4-yl)-7-pyridin-3-yl-[1,2,4]triazolo[1,5-a]pyridine-2,5-diamine as a solid.

Step 2:

A suspension of the product of Step 1 (376 mg, 1.16 mmol) in DMF (4 mL) was treated with TosNCO (0.25 g, 1.3 mmol), then microwaved at 60° C. for 5 min. After stirring at room temperature for 18 h, MeOH (5 mL) was added and the resulting precipitate was collected by filtration and dried in vacuo to yield 1-tosyl-3-[5-(1-methyl-piperidin-4-ylamino)-7-pyridin-3-yl-[1,2,4]triazolo[1,5-a]pyridin-2-yl]-urea.

Step 3:

The product of Step 2 (312 mg, 0.60 mol) and ethyl amine (3 mL of a 2 M solution in THF) in DMF (2 mL) was microwaved at 100° C. for 1 h. The homogeneous solution was pre-adsorbed onto SiO$_2$. Silica gel chromatography (5% NEt$_3$/0-5% MeOH/EtOAc) gave an oil which was triturated with EtOAc/hexane to afford the target compound 1-ethyl-3-[5-(1-methyl-piperidin-4-ylamino)-7-pyridin-3-yl[1,2,4]triazolo[1,5-a]pyridin-2-yl]-urea. MS m/z 395 (M+H$^+$).

Example 153

1-Ethyl-3-(5-[methyl-(1-methyl-piperidin-4-yl)-amino]-7-pyridin-3-yl-[1,2,4]triazolo[1,5-a]pyridin-2-yl]-urea Step 1:

A mixture of 5-chloro-7-pyridin-3-yl-[1,2,4]triazolo[1,5-a]pyridin-2-ylamine, which may be produced as in Example 1A, (400 mg, 1.6 mmol), 1-methyl-4-(methylamino)piperidine (250 mg, 1.95 mmol) and K$_2$CO$_3$ (220 mg, 1.6 mmol) in dioxane (1 mL) were microwaved at 180° C. for 12 h. The crude reaction mixture was taken up in MeOH/DCM and pre-adsorbed onto SiO$_2$. Silica gel chromatography (10% 1% MeOH/DCM gradient to 5% NEt$_3$/10% MeOH/EtOAc) gave N$^5$-methyl-N$^5$-(1-methyl-piperidin-4-yl)-7-pyridin-3-yl-[1,2,4]triazolo[1,5-a]pyridine-2,5-diamine.

Step 2:

TosNCO (0.38 g, 1.93 mmol) was added to a solution of the product of Step 1 (0.26 g, 0.77 mmol) in DMF (2.5 mL). After stirring at room temperature for 24 h, ethylamine (3.5 mL of a 2 M solution in THF, 7 mmol) was added to the homogeneous solution, from which a solid precipitated immediately. The mixture was microwaved at 120° C. for 10 min. After cooling to 5° C. for 1 h, a precipitate was collected by filtration, washed with a small volume of MeOH and dried in vacuo at 60° C. to yield 1-ethyl-3-(5-[methyl-(1-methyl-piperidin-4-yl)-amino]-7-pyridin-3-yl-[1,2,4]triazolo[1,5-a]pyridin-2-yl]-urea. MS m/z 409 (M+H$^+$).

Example 154

The in-vitro antibacterial activity of selected compounds was determined against a stain of *Neisseria gonorrhoeae*, GC525 (NG-2888), which is described by Rouquette-Loughlin et al, in *Journal of Bacteriology*, February 2003, p. 1101-1106, at p. 1103. In general, minimum inhibitory concentration (MIC) susceptibility testing followed procedures recommended by the National Committee for Clinical Laboratory Standards (NCCLS[1-2]) or followed the descriptions described below:

Bacterial Cultures

*Neisseria gonorrhoeae* strains were grown on Chocolate Agar II plates (BBL—Becton Dickinson Microbiology Systems, Cockeysville, Md.) and incubated at 35° C. in a humidified 5% CO$_2$ incubator (Form a Scientific, Marietta Ohio). For microbroth dilution MIC testing, *N. gonorrhoeae* were tested in gonococcal broth (GCB):

| Gonococcal Broth (GCB)[3] | |
|---|---|
| Proteose Peptone (BBL) | 15 g |
| Sodium Chloride | 5 g |
| Dipotassium Phosphate | 4 g |
| Potassium Dihydrogen Phosphate | 1 g |
| Soluble Starch (BBL) | 1 g |
| Sodium Bicarbonate | 420 mg |
| Distilled Water | 1000 mL |
| Isovitalex (BBL) | 10 mL |

Bacterial culture identifications were confirmed by standard microbiological methods.[4] *N. gonorrhoeae* strains were streaked onto appropriate agar plates for visualization of purity and expected colony morphology. Gram stains were also utilized.

Permanent Stock Culture Collection

Bacterial stock cultures are stored as frozen suspensions at −70 C. *N. gonorrhoeae* cultures are suspended in inactivated Horse Serum (Colorado Serum Company, Denver, Colo.) containing 7.5% glucose prior to snap freezing in a dry ice/ethanol bath.

Preparation of Standardized Test Inocula and Plate Inoculation

Frozen stock cultures were used as the initial source of organisms for performing microbroth dilution MIC testing. Stock cultures were passed on their respective growth medium at least one growth cycle (18-24 hours) prior to their use. Bacterial culture suspensions were prepared directly from Chocolate Agar II plates into 10 mL cation-adjusted Mueller-Hinton Broth (CAMHB, BBL, # BB215069). Before use, cultures were adjusted to an optical density value of 1.6-2 on a Perkin-Elmer Lambda EZ150 Spectrophotometer (Wellesley, Mass.) set at a wavelength of 600 nm. Random cultures were plated for validation of actual colony counts. The adjusted cultures were diluted 400-fold (0.25 mL inoculum+100 mL GCB) into gonococcal broth producing a starting inoculum of approximately 5×10$^5$ cfu/mL. These cultures were inoculated into test plates (100 uL/well) using a Biomek® FX workstation (Beckman Coulter Inc., Fullerton, Calif.). The inoculated plates were placed in stacks of no more than 4 and covered with an empty plate. Plates were incubated for 20-24 hours at 35 C in a humidified CO$_2$ incubator.

Test Compound ("Drug") Preparation

Drug stock solutions (2 mg/mL in DMSO) were prepared on the day of testing. Drugs were weight corrected for assay content where necessary.

Drug Dilution Tray Preparation

Microbroth dilution stock plates were prepared in two dilution series, 64-0.06 ug drug/mL and 1-0.001 ug drug/mL. For the high concentration series, 200 uL of stock solution (2 mg/mL) was added to duplicate rows of a 96-well plate. This was used as the first well in the dilution series. Serial two-fold decremental dilutions were made using a BioMek FX robot (Beckman Coulter Inc., Fullerton, Calif.) with 10 of the remaining 11 wells, each of which contained 100 uL of the appropriate solvent/diluent. Row 12 contained solvent/diluent only and served as the control. For tube one of the low concentration series, 200 uL of a 31.25 ug/mL stock was added to duplicate rows of a 96-well plate. Serial two-fold dilutions were made as described above.

Daughter plates were spotted (3.2 uL/well) from the stock plates listed above using the BioMek FX robot and were inoculated with organism (100 uL/well) as described previously.

Reading the Test

After incubation, the degree of growth in each well was read visually with the aid of a Test Reading Mirror (Dynatech Lab 220-16, Dynex Technologies, Chantilly, Va.). 96-well test plates are read in a darkened room with a single light shining from above. The MIC is the lowest concentration of drug that prevents macroscopically visible growth under the conditions of the test. Each drug dilution series was tested in duplicate; identical results are not always obtained. If MIC values in duplicate tests differ by 1 well (two-fold), the lower value is reported. If duplicate tests vary by 2 dilutions (four-fold), the middle value is reported. Greater than a 4-fold MIC variance between duplicate tests invalidates the result and leads to a repeat of the organism/drug combination.

REFERENCES

[1] National Committee for Clinical Laboratory Standards. Performance Standards for Antimicrobial Susceptibility Testing; Fourteenth Informational Supplement. NCCLS document M100-S14 {ISBN 1-56238-516-X}, NCCLS, 940 West Valley Road, Suite 1400, Wayne, Pa. 19087-1898 USA, 2004.

[2] National Committee for Clinical Laboratory Standards. Methods for Dilution Antimicrobial Tests for Bacteria That Grow Aerobically; Approved Standard-Sixth Edition. NCCLS document M7-A6 {ISBN 1-56238-486-4}, NCCLS, 940 West Valley Road, Suite 1400, Wayne, Pa. 19087-1898 USA, 2003.

[3] Shapiro M A, Heifetz C L, Sesnie J C. Comparison of microdilution and agar dilution procedures for testing antibiotic susceptibility of *Neisseria gonorrhoeae*. J Clin Microbiol 1984; 20:828-30.

[4] Murray P R, Baron E J, Jorgensen J H, Pfaller M A, Yolken R H. Manual of Clinical Microbiology, Eighth Edition. ASM Press {ISBN 1-55581-255-4}, American Society for Microbiology, 1752 N Street NW, Washington, D.C. 20036-2904 USA, 2003.

Using this protocol, the following results were generated:

| EXAMPLE NO. | MIC |
| --- | --- |
| 1 | 32.0 ug/mL |
| 2 | >64.0 ug/mL |
| 3 | >64.0 ug/mL |
| 4 | >64.0 ug/mL |
| 5 | 64.0 ug/mL |
| 6 | 16.0 ug/mL |
| 7 | 2.00 ug/mL |
| 8 | 1.00 ug/mL |
| 9 | 4.00 ug/mL |
| 10 | 8.00 ug/mL |
| 11 | >64.0 ug/mL |
| 12 | 2.00 ug/mL |
| 13 | 4.00 ug/mL |
| 14 | 16 ug/mL |
| 15 | 64.0 ug/mL |
| 16[1] | 1.00 ug/mL |
| 16[2] | 32 ug/mL |
| 17 | NT |
| 18 | NT |
| 19 | 1.00 ug/mL |
| 20 | 1.00 ug/mL |
| 21 | >64.0 ug/mL |
| 22 | 0.5 ug/mL |
| 23 | >64.0 ug/mL |
| 24 | >64.0 ug/mL |
| 25 | 1.00 ug/mL |
| 26 | 1.00 ug/mL |
| 27 | 2.00 ug/mL |
| 28 | >64.0 ug/mL |
| 29 | >64.0 ug/mL |
| 30 | >64.0 ug/mL |
| 31 | 8.00 ug/mL |
| 32 | 1.00 ug/mL |
| 33 | >64.0 ug/mL |
| 34 | 1.00 ug/mL |
| 35 | 8.00 ug/mL |
| 36 | >64.0 ug/mL |
| 37 | NT |
| 38 | NT |
| 39 | 32.0 ug/mL |
| 40 | 2.0 ug/mL |
| 41 | 16.0 ug/mL |

-continued

| EXAMPLE NO. | MIC |
|---|---|
| 42 | 8.0 ug/mL |
| 43 | >64.0 ug/mL |
| 44 | NT |
| 45 | >64.0 ug/mL |
| 46 | 1.0 ug/mL |
| 47 | 16.0 ug/mL |
| 48 | 16.0 ug/mL |
| 49 | >64.0 ug/mL |
| 50 | 2.00 ug/mL |
| 51 | 64.0 ug/mL |
| 52 | 4.00 ug/mL |
| 53 | 16.0 ug/mL |
| 54 | >64.0 ug/mL |
| 55 | 2.00 ug/mL |
| 56 | NT |
| 57 | 2.00 ug/mL |
| 58 | 2.00 ug/mL |
| 59 | NT |
| 60 | >16.0 ug/mL |
| 61 | 2.00 ug/mL |
| 62 | 2.00 ug/mL |
| 63 | 8.00 ug/mL |
| 64 | >64.0 ug/mL |
| 65 | 32.0 ug/mL |
| 66 | 4.00 ug/mL |
| 67 | 1.00 ug/mL |
| 68 | 2.00 ug/mL |
| 69 | 8.00 ug/mL |
| 70 | 1.00 ug/mL |
| 71 | 4.00 ug/mL |
| 72 | 4.00 ug/mL |
| 73 | 16.0 ug/mL |
| 74 | NT |
| 75 | 2.00 ug/mL |
| 76 | 8.00 ug/mL |
| 77 | 1.00 ug/mL |
| 78 | 8.00 ug/mL |
| 79 | 8.00 ug/mL |
| 80 | >64.0 ug/mL |
| 81 | 2.00 ug/mL |
| 82 | >64.0 ug/mL |
| 84 | NT |
| 85 | NT |
| 86 | 16.0 ug/mL |
| 87 | 8.00 ug/mL |
| 88 | 8.00 ug/mL |
| 89 | 8.00 ug/mL |
| 90 | >64.0 ug/mL |
| 91 | 16.0 ug/mL |
| 92 | 8.00 ug/mL |
| 93 | 2.00 ug/mL |
| 94 | NT |
| 95 | 32.0 ug/mL |
| 96 | 2.00 ug/mL |
| 97 | NT |
| 98 | 2.00 ug/mL |
| 99 | 8.00 ug/mL |
| 100 | NT |
| 101 | NT |
| 102 | >64.0 ug/mL |
| 103 | >64.0 ug/mL |
| 104 | 64.0 ug/mL |
| 105 | 16.0 ug/mL |
| 106 | >64.0 ug/mL |
| 107 | >64.0 ug/mL |
| 108 | 2.00 ug/mL |
| 109 | 2.00 ug/mL |
| 110 | 4.00 ug/mL |
| 111 | 8.00 ug/mL |
| 112 | 8.00 ug/mL |
| 113 | 64.0 ug/mL |
| 114 | 32.0 ug/mL |
| 115 | 32.0 ug/mL |
| 116 | >64.0 ug/mL |
| 117 | >64.0 ug/mL |
| 118 | >64.0 ug/mL |
| 119 | 64.0 ug/mL |

-continued

| EXAMPLE NO. | MIC |
|---|---|
| 120 | >64.0 ug/mL |
| 121 | 64.0 ug/mL |
| 122 | 0.0600 ug/mL |
| 123 | >64.0 ug/mL |
| 124 | 64.0 ug/mL |
| 125 | 0.0600 ug/mL |
| 126 | 16.0 ug/mL |
| 127 | 32.0 ug/mL |
| 128 | >64.0 ug/mL |
| 129 | 1.00 ug/mL |
| 130 | 16.0 ug/mL |
| 131 | 32.0 ug/mL |
| 132 | 2.00 ug/mL |
| 133 | 0.250 ug/mL |
| 134 | 32.0 ug/mL |
| 135 | 8.00 ug/mL |
| 136 | 4.00 ug/mL |
| 137 | 32.0 ug/mL |
| 138 | 0.500 ug/mL |
| 139 | 1.00 ug/mL |
| 140 | 64.0 ug/mL |
| 141 | 32.0 ug/mL |
| 142 | 16.0 ug/mL |
| 143 | 32.0 ug/mL |
| 144 | 32.0 ug/mL |
| 145 | 16.0 ug/mL |
| 146 | 32.0 ug/mL |
| 147 | 4.00 ug/mL |
| 148 | 4.00 ug/mL |
| 149 | 16.0 ug/mL |
| 150 | 32.0 ug/mL |
| 151 | 32.0 ug/mL |
| 152 | 8.00 ug/mL |

[1]Final Product
[2]Product Step 1

What is claimed is:

1. A compound of the formula:

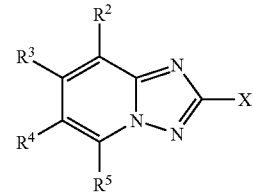

or a salt thereof, wherein:

X is represented by NH—C(J)-T-$R^1$ or NH—$SO_2$—NH—$R^1$;

J is represented by O or S;

T is represented by NH or O;

$R^1$ is represented by a substituent selected from the group consisting of:
  i) hydrogen,
  ii) ($C_1$-$C_6$)alkyl, optionally substituted,
  iii) ($C_3$-$C_6$)cycloalkyl, optionally substituted,
  iv) ($C_3$-$C_6$) cycloalkyl($C_1$-$C_6$)alkyl, in which the alkyl and cycloalkyl moieties may each be optionally substituted,
  v) phenyl, optionally substituted, and,
  vi) phenyl ($C_1$-$C_6$)alkyl, in which the alkyl and phenyl moieties may each be optionally substituted;

$R^2$, $R^3$, $R^4$, and $R^5$ are each independently represented by a substituent selected from the group consisting of:
  i) hydrogen,
  ii) halogen, iii) cyano,
iv) hydroxy,
v) $(C_1-C_{12})$alkyl, optionally substituted,
vi) $(C_2-C_{12})$alkenyl, optionally substituted,
vii) $(C_2-C_{12})$alkynyl, optionally substituted,
viii) $(C_3-C_{10})$cycloalkyl, optionally substituted,
ix) $(C_3-C_{10})$ cycloalkyl$(C_1-C_6)$alkyl, in which the alkyl and cycloalkyl moieties may each be optionally substituted,
x) $(C_6-C_{10})$aryl, optionally substituted,
xi) $(C_6-C_{10})$aryl $(C_1-C_6)$alkyl, in which the alkyl and aryl moieties may each be optionally substituted,
xii) heteroaryl, optionally substituted,
xiii) heteroaryl$(C_1-C_{12})$alkyl, in which the heteroaryl and alkyl moieties may each be optionally substituted,
xiv) heterocyclic, optionally substituted,
xv) heterocyclic$(C_1-C_{12})$alkyl, in which the alkyl and heterocyclic moieties may each be substituted,
xvi) $(CH_2)_z$—$SR^6$,
xvii) $(CH_2)_z$—$OR^6$,
xviii) $(CH_2)_z$—$NR^7R^6$,
xix) $(CH_2)_z$—$COOR^6$,
xx) $(CH_2)_z$—$CONR^6R^7$,
xxi) $(CH_2)_z$—$NR^7COR^6$,
xxii) $(CH_2)_z$—$OCOR^6$,
xxiii) $(CH_2)_z$—$C(O)R^6$,
xxiv) $(CH_2)_z$—$C(O)C(O)NR^6R^7$,
xxv) $(CH_2)_z$—$SO_xR^6$,
xxvi) $(CH_2)_z$—$SO_2NR^6R^7$,
xxvii) $(CH_2)_z$—$NR^7SO_2R^6$,
xxviii) $C(R^6)$=$NOR^7$,
xxix)

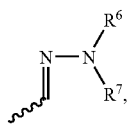

wherein " ∼ " indicates the point of attachment, and,
xxx)

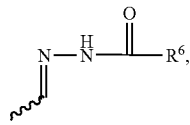

wherein " ∼ " indicates the point of attachment;
z is an integer selected from 0, 1, 2, 3, or 4;
x is an integer selected from 1 or 2;
$R^6$ is represented by a substituent selected from the group consisting of:
i) hydrogen
ii) $(C_1-C_{12})$alkyl, optionally substituted,
iii) $(C_2-C_{12})$alkenyl, optionally substituted,
iv) $(C_2-C_{12})$alkynyl, optionally substituted,
v) $(C_3-C_{10})$cycloalkyl, optionally substituted,
vi) $(C_3-C_{10})$ cycloalkyl$(C_1-C_6)$alkyl, in which the alkyl and cycloalkyl moieties may each be optionally substituted,
vii) $(C_6-C_{10})$aryl, optionally substituted,
viii) $(C_6-C_{10})$aryl $(C_1-C_6)$alkyl, in which the alkyl and aryl moieties may each be optionally substituted,
ix) heteroaryl, optionally substituted, x) heteroaryl$(C_1-C_{12})$alkyl, in which the heteroaryl and alkyl moieties may each be optionally substituted,
xi) heterocyclic, optionally substituted,
xii) heterocyclic$(C_1-C_{12})$alkyl, in which the alkyl and heterocyclic moieties may each be substituted, and;

$R^7$ is represented by a substituent selected from the group consisting of hydrogen and $(C_1-C_6)$alkyl;

with the proviso that one of $R^2$ or $R^5$ will be represented by a substituent selected from the group consisting of hydrogen, halogen, methyl, cyano, hydroxy, trifluoromethyl, trifluoromethoxy, and methoxy.

2. A compound according to claim 1 in which X is NH—C(J)-T-$R^1$.

3. A compound according to claim 2 in which J is O and T is NH.

4. A compound according to claim 1 in which $R^2$ is represented by a substituent selected from the group consisting of hydrogen, halogen, methyl, cyano, hydroxy, trifluoromethyl, trifluoromethoxy, and methoxy.

5. A compound according to claim 4 in which $R^3$ is represented by:
i) $(C_3-C_{10})$cycloalkyl, optionally substituted,
ii) $(C_3-C_{10})$ cycloalkyl$(C_1-C_6)$alkyl, in which the alkyl and cycloalkyl moieties may each be optionally substituted,
iii) $(C_6-C_{10})$aryl, optionally substituted,
iv) $(C_6-C_{10})$aryl $(C_1-C_6)$alkyl, in which the alkyl and aryl moieties may each be optionally substituted,
v) heteroaryl, optionally substituted,
vi) heteroaryl$(C_1-C_{12})$alkyl, in which the heteroaryl and alkyl moieties may each be optionally substituted,
vii) heterocyclic, optionally substituted, and
viii) heterocyclic$(C_1-C_{12})$alkyl, in which the alkyl and heterocyclic moieties may each be substituted.

6. A compound according to claim 5 in which $R^4$ is represented by hydrogen, $(C_1-C_{12})$alkyl, $(CH_2)_z$—$OR^6$, halogen, or cyano.

7. A compound according to claim 6 in which $R^5$ is represented by
i) $(C_3-C_{10})$cycloalkyl, optionally substituted,
ii) $(C_3-C_{10})$ cycloalkyl$(C_1-C_6)$alkyl, in which the alkyl and cycloalkyl moieties may each be optionally substituted,
iii) $(C_6-C_{10})$aryl, optionally substituted,
iv) $(C_6-C_{10})$aryl $(C_1-C_6)$alkyl, in which the alkyl and aryl moieties may each be optionally substituted,
v) heteroaryl, optionally substituted,
vi) heteroaryl$(C_1-C_{12})$alkyl, in which the heteroaryl and alkyl moieties may each be optionally substituted,
vii) heterocyclic, optionally substituted,
viii) heterocyclic$(C_1-C_{12})$alkyl, in which the alkyl and heterocyclic moieties may each be substituted,
ix) $CH_2)_z$—$SR^6$,
x) $(CH_2)_z$—$OR^6$,
xi) $(CH_2)_z$—$NR^7R^6$,
xii) $(CH_2)_z$—$COOR^6$,
xiii) $(CH_2)_z$—$CONR^6R^7$,
xiv) $(CH_2)_z$—$NR^7COR^6$,
xv) $(CH_2)_z$—$OCOR^6$,
xvi) $(CH_2)_z$—$C(O)R^6$,
xvii) $(CH_2)_z$—$C(O)C(O)NR^6R^7$,
xviii) $(CH_2)_z$—$SO_xR^6$,
xix) $(CH_2)_z$—$SO_2NR^6R^7$,
xx) $(CH_2)$—$NR^7$—$SO_2R^6$, or
xxi) $C(R^6)$=$NOR^7$.

8. A compound of the formula:

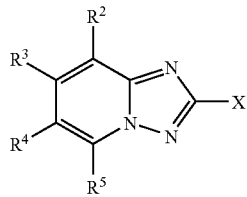

or a salt thereof, wherein:
X is represented by NH—C(J)-T-R$^1$,
J is represented by O or S;
T is represented by NH or O;
R$^1$ is represented by a substituent selected from the group consisting of:
  i) hydrogen,
  ii) (C$_1$-C$_6$)alkyl, optionally substituted,
  iii) (C$_3$-C$_6$)cycloalkyl, optionally substituted,
  iv) (C$_3$-C$_6$) cycloalkyl(C$_1$-C$_6$)alkyl, in which the alkyl and cycloalkyl moieties may each be optionally substituted,
  v) phenyl, optionally substituted, and,
  vi) phenyl (C$_1$-C$_6$)alkyl, in which the alkyl and phenyl moieties may each be optionally substituted;
R$^2$ is represented by hydrogen, halogen or cyano;
R$^3$ is represented by:
  i) (C$_3$-C$_{10}$)cycloalkyl, optionally substituted,
  ii) (C$_3$-C$_{10}$) cycloalkyl(C$_1$-C$_6$)alkyl, in which the alkyl and cycloalkyl moieties may each be optionally substituted,
  iii) (C$_6$-C$_{10}$)aryl, optionally substituted,
  iv) (C$_6$-C$_{10}$)aryl (C$_1$-C$_6$)alkyl, in which the alkyl and aryl moieties may each be optionally substituted,
  v) heteroaryl, optionally substituted,
  vi) heteroaryl(C$_1$-C$_{12}$)alkyl, in which the heteroaryl and alkyl moieties may each be optionally substituted,
  vii) heterocyclic, optionally substituted, or
  viii) heterocyclic(C$_1$-C$_{12}$)alkyl, in which the alkyl and heterocyclic moieties may each be substituted;
R$^4$ is represented by:
  i) hydrogen,
  ii) halogen,
  iii) cyano,
  iv) hydroxyl,
  v) C$_1$-C$_6$ alkyl,
  vi) phenyl, optionally substituted, or
  vii) phenyl C$_1$-C$_6$ alkyl, in which the phenyl and alkyl moieties may each be optionally substituted;
R$^5$ is represented by
  i) (C$_3$-C$_{10}$)cycloalkyl, optionally substituted,
  ii) (C$_3$-C$_{10}$) cycloalkyl(C$_1$-C$_6$)alkyl, in which the alkyl and cycloalkyl moieties may each be optionally substituted,
  iii) (C$_6$-C$_{10}$)aryl, optionally substituted,
  iv) (C$_6$-C$_{10}$)aryl (C$_1$-C$_6$)alkyl, in which the alkyl and aryl moieties may each be optionally substituted,
  v) heteroaryl, optionally substituted,
  vi) heteroaryl(C$_1$-C$_{12}$)alkyl, in which the heteroaryl and alkyl moieties may each be optionally substituted,
  vii) heterocyclic, optionally substituted,
  viii) heterocyclic(C$_1$-C$_{12}$)alkyl, in which the alkyl and heterocyclic moieties may each be substituted
  ix) (CH$_2$)$_z$—OR$^6$,
  x) (CH$_2$)$_z$—NR$^6$R$^7$,
  xi) (CH$_2$)$_z$—SR$^6$,
  xii) (CH$_2$)$_z$—COOR$^6$,
  xiii) (CH$_2$)$_z$—CONR$^6$R$^7$,
  xiv) (CH$_2$)$_z$—NR$^7$COR$^6$,
  xv) (CH$_2$)$_z$—OCOR$^6$,
  xvi) (CH$_2$)$_z$—C(O)R$^6$,
  xvii) (CH$_2$)$_z$—C(O)C(O)NR$^6$R$^7$,
  xviii) (CH$_2$)$_z$—SO$_x$R$^6$,
  xix) (CH$_2$)$_z$—SO$_2$NR$^6$R$^7$,
  xx) (CH$_2$)$_z$—NR$^7$SO$_2$R$^6$, or
  xxi) C(R$^6$)=NOR$^7$;
z is an integer selected from 0, 1, 2, 3, or 4;
x is an integer selected from 1, or 2;
R$^6$ is represented by a substituent selected from the group consisting of:
  i) hydrogen,
  ii) (C$_1$-C$_{12}$)alkyl optionally substituted,
  iii) heteroaryl, heteroaryl (C$_1$-C$_{12}$) alkyl, heterocyclic, etc.
  iii) (C$_2$-C$_{12}$)alkenyl optionally substituted,
  iv) (C$_2$-C$_{12}$)alkynyl optionally substituted,
  v) optionally substituted (C$_6$-C$_{10}$)aryl, and,
  vi) (C$_6$-C$_{10}$)aryl (C$_1$-C$_6$)alkyl, in which the alkyl and aryl moieties may each be optionally substituted and;
R$^7$ is represented by a substituent selected from the group consisting of hydrogen and (C$_1$-C$_6$)alkyl.

9. A compound of the formula:

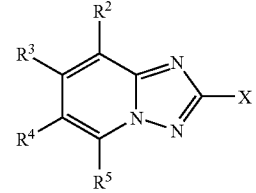

or a salt thereof, wherein:
X is represented by NH—C(J)-T-R$^1$,
J is represented by O or S;
T is represented by NH or O;
R$^1$ is represented by a substituent selected from the group consisting of:
  i) hydrogen,
  ii) (C$_1$-C$_6$)alkyl, optionally substituted,
  iii) (C$_3$-C$_6$)cycloalkyl, optionally substituted,
  iv) (C$_3$-C$_6$) cycloalkyl(C$_1$-C$_6$)alkyl, in which the alkyl and cycloalkyl moieties may each be optionally substituted,
  v) phenyl, optionally substituted, and,
  vi) phenyl (C$_1$-C$_6$)alkyl, in which the alkyl and phenyl moieties may each be optionally substituted;
R$^2$ is represented by
  i) (C$_3$-C$_{10}$)cycloalkyl, optionally substituted,
  ii) (C$_3$-C$_{10}$) cycloalkyl(C$_1$-C$_6$)alkyl, in which the alkyl and cycloalkyl moieties may each be optionally substituted,
  iii) (C$_6$-C$_{10}$)aryl, optionally substituted,
  iv) (C$_6$-C$_{10}$)aryl (C$_1$-C$_6$)alkyl, in which the alkyl and aryl moieties may each be optionally substituted,
  v) heteroaryl, optionally substituted,
  vi) heteroaryl(C$_1$-C$_{12}$)alkyl, in which the heteroaryl and alkyl moieties may each be optionally substituted,
  vii) heterocyclic, optionally substituted,
  viii) heterocyclic(C$_1$-C$_{12}$)alkyl, in which the alkyl and heterocyclic moieties may each be substituted xxii) $(CH_2)_z$—$OR^6$,
xxiii) $(CH_2)_z$—$NR^6R^7$,
ix) $(CH_2)_z$—$SR^6$,
x) $(CH_2)_z$—$COOR^6$,
xi) $(CH_2)_z$—$CONR^6R^7$,
xii) $(CH_2)_z$—$NR^7COR^6$,
xiii) $(CH_2)_z$—$OCOR^6$,
xiv) $(CH_2)_z$—$C(O)R^6$,
xv) $(CH_2)_z$—$C(O)C(O)NR^6R^7$,
xvi) $(CH_2)_z$—$SO_xR^6$,
xvii) $(CH_2)_z$—$SO_2NR^6R^7$,
xviii) $(CH_2)_z$—$NR^7$—$SO_2R^6$, or
xix) $C(R^6)$=$NOR^7$;

$R^3$ is represented by:
  i) hydrogen,
  ii) halogen,
  iii) cyano,
  iv) hydroxyl,
  v) $C_1$-$C_6$ alkyl,
  vi) phenyl, optionally substituted, or
  viii) phenyl $C_1$-$C_6$ alkyl, in which the phenyl and alkyl moieties may each be optionally substituted;

$R^4$ is represented by:
  i) $(C_3$-$C_{10})$cycloalkyl, optionally substituted,
  ii) $(C_3$-$C_{10})$ cycloalkyl$(C_1$-$C_6)$alkyl, in which the alkyl and cycloalkyl moieties may each be optionally substituted,
  iii) $(C_6$-$C_{10})$aryl, optionally substituted,
  iv) $(C_6$-$C_{10})$aryl $(C_1$-$C_6)$alkyl, in which the alkyl and aryl moieties may each be optionally substituted,
  v) heteroaryl, optionally substituted,
  vi) heteroaryl$(C_1$-$C_{12})$alkyl, in which the heteroaryl and alkyl moieties may each be optionally substituted,
  vii) heterocyclic, optionally substituted, or
  viii) heterocyclic$(C_1$-$C_{12})$alkyl, in which the alkyl and heterocyclic moieties may each be substituted;

$R^5$ is represented by hydrogen, halogen or cyano;

z is an integer selected from 0, 1, 2, 3, or 4;

x is an integer selected from 1 or 2;

$R^6$ is represented by a substituent selected from the group consisting of:
  i) hydrogen,
  ii) $(C_1$-$C_{12})$alkyl optionally substituted,
  iii) heteroaryl, heteroaryl $(C_1$-$C_{12})$ alkyl, heterocyclic, etc.
  iii) $(C_2$-$C_{12})$alkenyl optionally substituted,
  iv) $(C_2$-$C_{12})$alkynyl optionally substituted,
  v) optionally substituted $(C_6$-$C_{10})$aryl, and,
  vi) $(C_6$-$C_{10})$aryl $(C_1$-$C_6)$alkyl, in which the alkyl and aryl moieties may each be optionally substituted, and;

$R^7$ is represented by a substituent selected from the group consisting of hydrogen and $(C_1$-$C_6)$alkyl.

10. A pharmaceutical composition comprising a compound according to claim 1 in admixture with at least one pharmaceutically acceptable carrier.

11. A method for treating bacterial infections, comprising, administering a compound according to claim 1 to a patient in need thereof.

* * * * *

UNITED STATES PATENT AND TRADEMARK OFFICE
CERTIFICATE OF CORRECTION

PATENT NO. : 7,524,860 B2  
APPLICATION NO. : 11/576538  
DATED : April 28, 2009  
INVENTOR(S) : Butler et al.

Page 1 of 1

It is certified that error appears in the above-identified patent and that said Letters Patent is hereby corrected as shown below:

On the title page, item (73) should read as follows:

(73) Assignee: Warner-Lambert Company, LLC, Morris Plains, NJ (US)

Signed and Sealed this  
Twelfth Day of February, 2013

Teresa Stanek Rea  
*Acting Director of the United States Patent and Trademark Office*